United States Patent
Moon et al.

(10) Patent No.: US 10,069,087 B2
(45) Date of Patent: Sep. 4, 2018

(54) ORGANIC ELECTROLUMINESCENT COMPOUNDS AND ORGANIC ELECTROLUMINESCENT DEVICE COMPRISING THE SAME

(71) Applicant: Rohm and Haas Electronic Materials Korea Ltd., Cheonan (KR)

(72) Inventors: Doo-Hyeon Moon, Hwaseong (KR); Hee-Ryong Kang, Yongin (KR)

(73) Assignee: ROHM AND HAAS ELECTRONIC MATERIALS KOREA LTD., Cheonan (KR)

(*) Notice: Subject to any disclaimer, the term of this patent is extended or adjusted under 35 U.S.C. 154(b) by 0 days.

(21) Appl. No.: 15/570,401

(22) PCT Filed: Mar. 17, 2016

(86) PCT No.: PCT/KR2016/002694
§ 371 (c)(1),
(2) Date: Oct. 30, 2017

(87) PCT Pub. No.: WO2016/182186
PCT Pub. Date: Nov. 17, 2016

(65) Prior Publication Data
US 2018/0151809 A1    May 31, 2018

(30) Foreign Application Priority Data
May 11, 2015 (KR) .................. 10-2015-0065277

(51) Int. Cl.
C07D 471/22 (2006.01)
H01L 51/00 (2006.01)
C07D 487/16 (2006.01)
C07D 487/22 (2006.01)
C07D 491/22 (2006.01)
C07D 495/22 (2006.01)
C09K 11/06 (2006.01)
H05B 33/14 (2006.01)
H01L 51/50 (2006.01)

(52) U.S. Cl.
CPC ........ H01L 51/0072 (2013.01); C07D 471/22 (2013.01); C07D 487/16 (2013.01); C07D 487/22 (2013.01); C07D 491/22 (2013.01); C07D 495/22 (2013.01); C09K 11/06 (2013.01); H01L 51/0061 (2013.01); H01L 51/0067 (2013.01); H05B 33/14 (2013.01); C09K 2211/1018 (2013.01); H01L 51/0085 (2013.01); H01L 51/5016 (2013.01); H01L 2251/5384 (2013.01)

(58) Field of Classification Search
None
See application file for complete search history.

(56) References Cited

U.S. PATENT DOCUMENTS

| 8,795,848 | B2 | 8/2014 | Kai et al. |
| 8,835,626 | B2 | 9/2014 | Parham et al. |
| 9,356,243 | B2* | 5/2016 | Parham ............. C07D 471/16 |
| 2007/0249590 | A1 | 10/2007 | Wilson et al. |

* cited by examiner

*Primary Examiner* — Heidi Reese
(74) *Attorney, Agent, or Firm* — S. Matthew Cairns

(57) ABSTRACT

The present invention relates to an organic electroluminescent compounds and organic electroluminescent device comprising the same. The organic electroluminescent compound according to the present invention is effective to produce an organic electroluminescent device having low driving voltage, excellent luminous and power efficiencies, and significantly improved driving lifespan.

5 Claims, No Drawings

ORGANIC ELECTROLUMINESCENT COMPOUNDS AND ORGANIC ELECTROLUMINESCENT DEVICE COMPRISING THE SAME

TECHNICAL FIELD

The present disclosure relates to organic electroluminescent compounds and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

An organic EL device (OLED) is a device changing electrical energy to light by applying electricity to an organic electroluminescent material, and generally has a structure comprising an anode, a cathode, and an organic layer between the anode and the cathode. The organic layer of an organic EL device may be comprised of a hole injection layer, a hole transport layer, an electron blocking layer, a light-emitting layer (which comprises host and dopant materials), an electron buffer layer, a hole blocking layer, an electron transport layer, an electron injection layer, etc., and the materials used for the organic layer are categorized by their functions in hole injection material, hole transport material, electron blocking material, light-emitting material, electron buffer material, hole blocking material, electron transport material, electron injection material, etc. In the organic EL device, due to an application of a voltage, holes are injected from the anode to the light-emitting layer, electrons are injected from the cathode to the light-emitting layer, and excitons of high energies are formed by a recombination of the holes and the electrons. By this energy, organic luminescent compounds reach an excited state, and light emission occurs by emitting light from energy due to the excited state of the organic luminescent compounds returning to a ground state.

The most important factor determining luminous efficiency in an organic EL device is light-emitting materials. A light-emitting material must have high quantum efficiency, high electron and hole mobility, and the formed light-emitting material layer must be uniform and stable. Light-emitting materials are categorized into blue, green, and red light-emitting materials dependent on the color of the light emission, and additionally yellow or orange light-emitting materials. In addition, light-emitting materials can also be categorized into host and dopant materials according to their functions. Recently, the development of an organic EL device providing high efficiency and long lifespan is an urgent issue. In particular, considering EL characteristic requirements for a middle or large-sized panel of OLED, materials showing better characteristics than conventional ones must be urgently developed. The host material, which acts as a solvent in a solid state and transfers energy, needs to have high purity and a molecular weight appropriate for vacuum deposition. Furthermore, the host material needs to have high glass transition temperature and high thermal degradation temperature to achieve thermal stability, high electro-chemical stability to achieve a long lifespan, ease of forming an amorphous thin film, good adhesion to materials of adjacent layers, and non-migration to other layers.

Korean Patent No. 10-1082144 discloses an indolocarbazole derivative bonding an (C6-C20) aromatic heterocyclic group of a fused-ring structure with a valence of (n+1) as a host of the light-emitting layer. However, necessity of new organic electroluminescent compounds having superior luminous efficiency and improved driving stability is continuously to the fore.

In this regard, the present inventors have tried to invent new organic electroluminescent compounds that can provide excellent performance compared to the conventional ones, and have found that the compounds of the present disclosure provide a device having high luminous and power efficiencies and superior device performance.

DISCLOSURE OF THE INVENTION

Problems to be Solved

The object of the present disclosure is to provide organic electroluminescent compounds having low driving voltage, excellent luminous and power efficiencies, and significantly improved driving lifespan.

Solution to Problems

The present inventors found that the above objective can be achieved by an organic electroluminescent compound represented by the following formula 1:

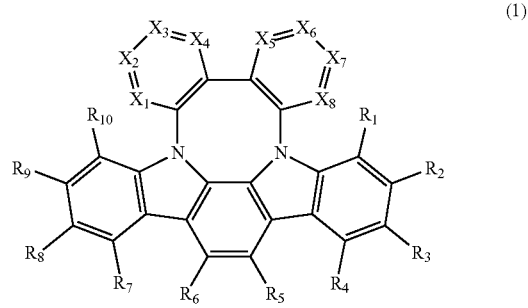

Wherein $X_1$ to $X_8$ represent N or $CR_{11}$;

$R_1$ to $R_{11}$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_{12}R_{13}$, or $-SiR_{14}R_{15}R_{16}$; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur;

$R_{12}$ to $R_{16}$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl;

the heterocycloalkyl or the heteroaryl contains at least one hetero atom selected from B, N, O, S, Si, and P.

Effects of the Invention

By using the organic electroluminescent compound of the present invention as a host of the light-emitting layer, efficiency and lifespan of the organic electroluminescent device are significantly improved compared to the conventional organic electroluminescent compounds. Specifically, the organic electroluminescent compound of the present invention can provide an organic electroluminescent device having high luminous and power efficiencies, and significantly improved lifespan.

EMBODIMENTS OF THE INVENTION

Hereinafter, the present disclosure will be described in detail. However, the following description is intended to explain the disclosure, and is not meant in any way to restrict the scope of the disclosure.

The present disclosure relates to an organic electroluminescent compound represented by formula 1, an organic electroluminescent material comprising the organic electroluminescent compound, and an organic electroluminescent device comprising the organic electroluminescent material.

In formula 1, preferably, $R_1$ to $R_{11}$, each independently, represent hydrogen, deuterium, a substituted or unsubstituted (C1-C20)alkyl, a substituted or unsubstituted (C3-C20)cycloalkyl, a substituted or unsubstituted (C3-C20)cycloalkenyl, a substituted or unsubstituted (C6-C20)aryl, a substituted or unsubstituted (3- to 20-membered)heteroaryl, or —$NR_{12}R_{13}$; or are linked to an adjacent substituent(s) to form a substituted or unsubstituted, mono- or polycyclic, (C3-C20) alicyclic or aromatic ring, whose carbon atom(s) may be replaced with at least one hetero atom selected from nitrogen, oxygen, and sulfur; and $R_{12}$ to $R_{16}$, each independently, represent a substituted or unsubstituted (C1-C20) alkyl, a substituted or unsubstituted (C3-C20)cycloalkyl, a substituted or unsubstituted (C3-C20)cycloalkenyl, a substituted or unsubstituted (C6-C20)aryl, or a substituted or unsubstituted (3- to 20-membered)heteroaryl.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc.; "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C1-C30)alkoxy" is meant to be a linear or branched alkoxy having 1 to 30 carbon atoms constituting the chain, in which the number of carbon atoms is preferably 1 to 20, more preferably 1 to 10, and includes methoxy, ethoxy, propoxy, isopropoxy, 1-ethylpropoxy, etc.; "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc.; "(3- to 7-membered)heterocycloalkyl" is a cycloalkyl having 3 to 7 ring backbone atoms, including at least one heteroatom selected from B, N, O, S, Si, and P, preferably O, S, and N, and includes pyrrolidine, thiolan, tetrahydropyran, etc.; "(C6-C30)aryl" is a monocyclic or fused ring derived from an aromatic hydrocarbon having 6 to 30 ring backbone carbon atoms, in which the number of carbon atoms is preferably 6 to 20, more preferably 6 to 15, and includes phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, etc.; "3- to 30-membered heteroaryl" is an aryl having 3 to 30 ring backbone atoms, preferably 3 to 20 ring backbone atoms, and more preferably 3 to 15 ring backbone atoms, including at least one, preferably 1 to 4 heteroatoms selected from the group consisting of B, N, O, S, Si, and P; may a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. Further, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted (C1-C30) alkyl, the substituted (C3-C30)cycloalkyl, the substituted (C3-C30)cycloalkenyl, the substituted (3- to 7-membered) heterocycloalkyl, the substituted (C6-C30)aryl, the substituted (3- to 30-membered)heteroaryl, and the substituted mono- or polycyclic, (C3-C30) alicyclic or aromatic ring in formula 1, each independently, are at least one selected from the group consisting of deuterium, a halogen, a cyano, a carboxyl, a nitro, a hydroxyl, a (C1-C30)alkyl, a halo(C1-C30)alkyl, a (C2-C30) alkenyl, a (C2-C30) alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (5- to 30-membered)heteroaryl unsubstituted or substituted with a (C6-C30)aryl, a (C6-C30)aryl unsubstituted or substituted with a (5- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30) arylamino, a (C1-C30)alkyl(C6-C30)arylamino, a (C1-C30) alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

The organic electroluminescent compound represented by formula 1 includes the following compounds, but is not limited thereto:

C-1
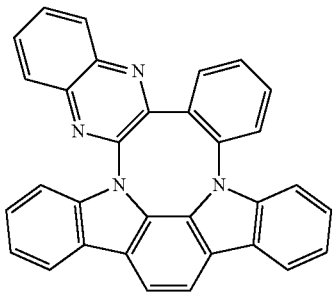
C-2
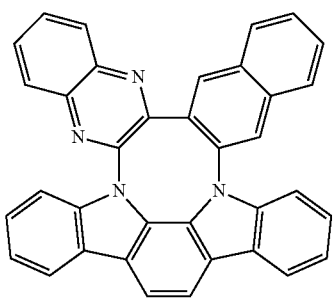
C-3
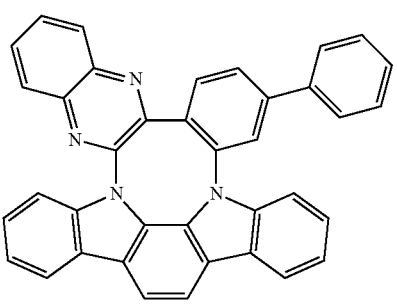
C-4
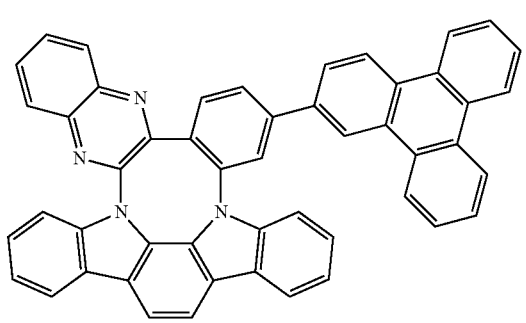
C-5
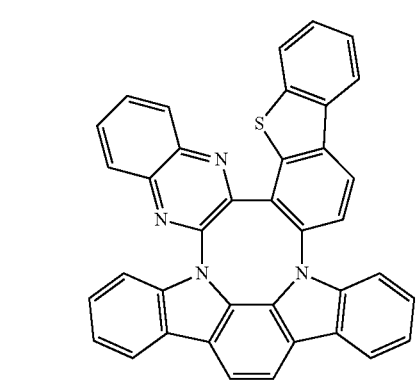
C-6
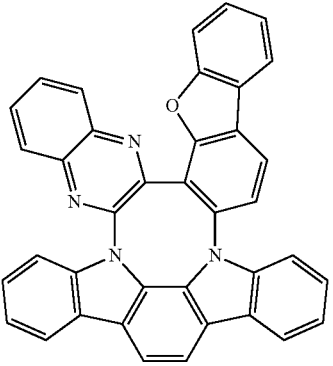
C-7
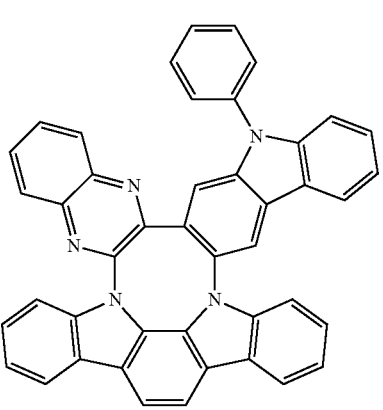
C-8
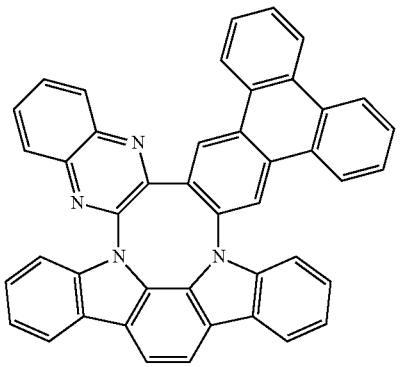
C-9
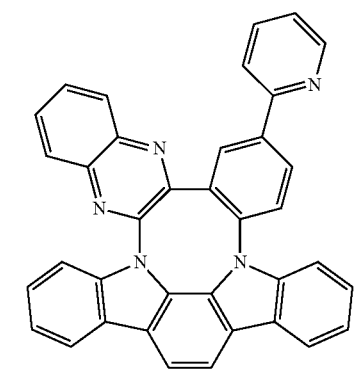

C-10
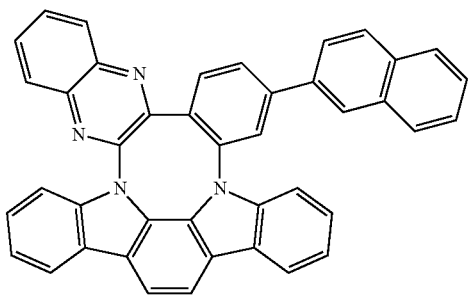
C-11
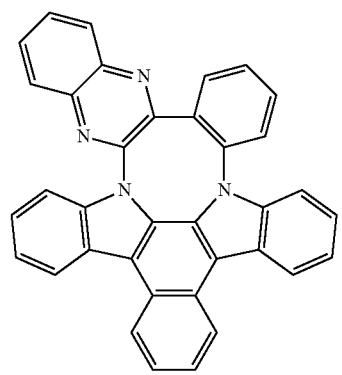
C-12
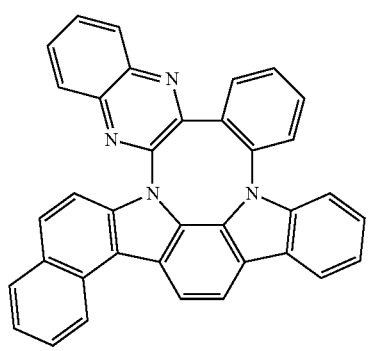
C-13
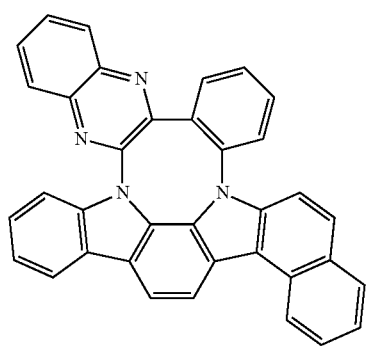
C-14
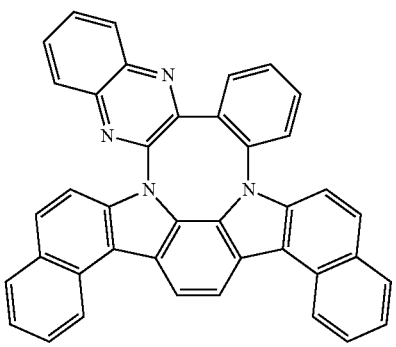
C-15
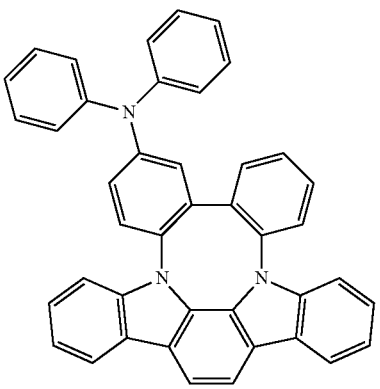
C-16
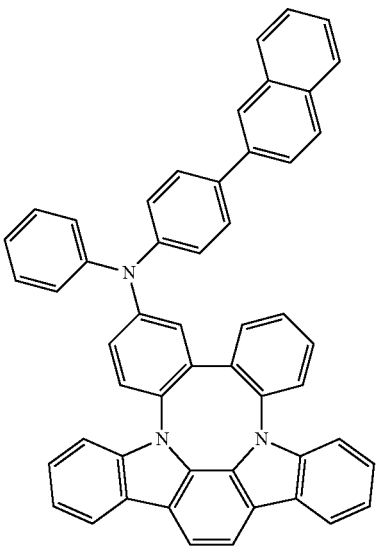

C-17
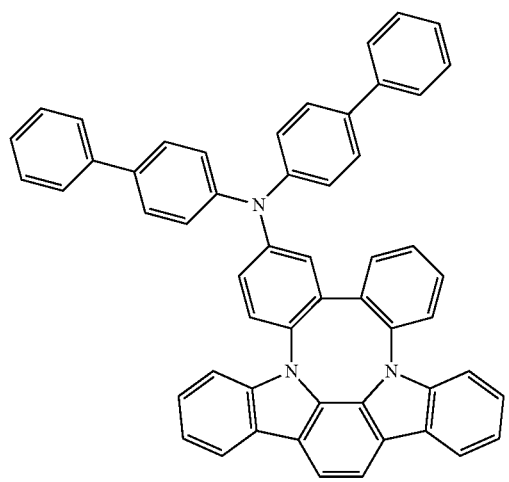
C-18
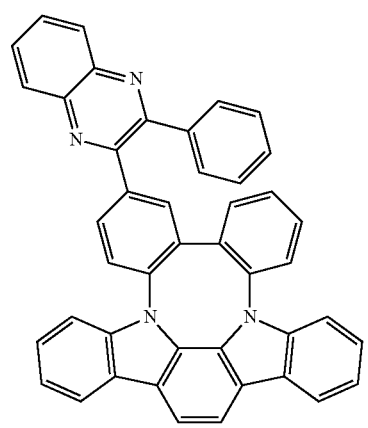
C-19
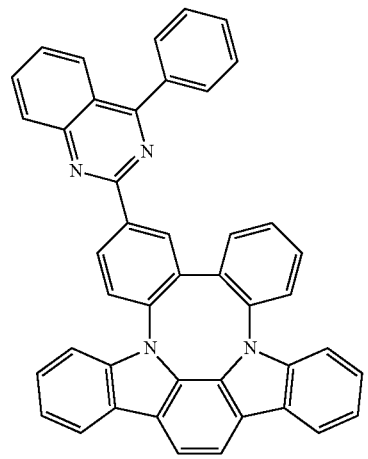
C-20
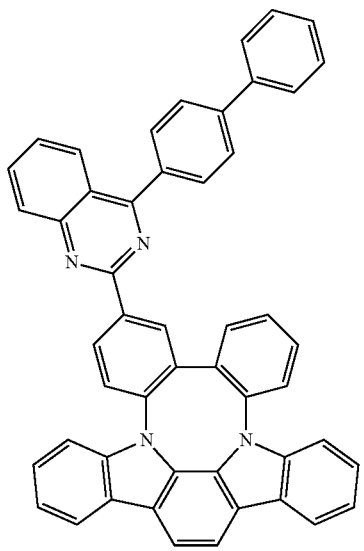
C-21
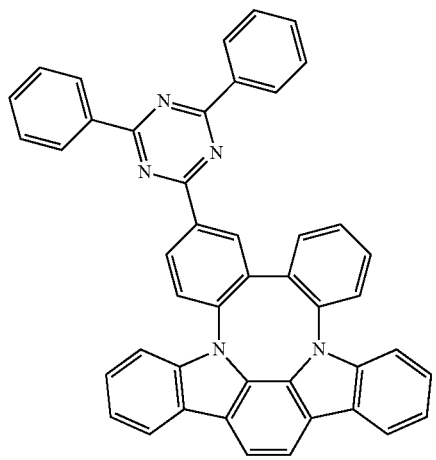
C-22
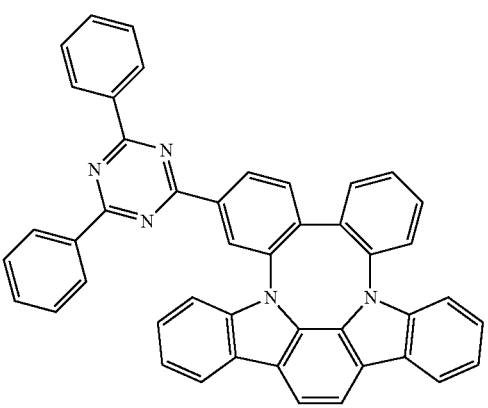

C-23
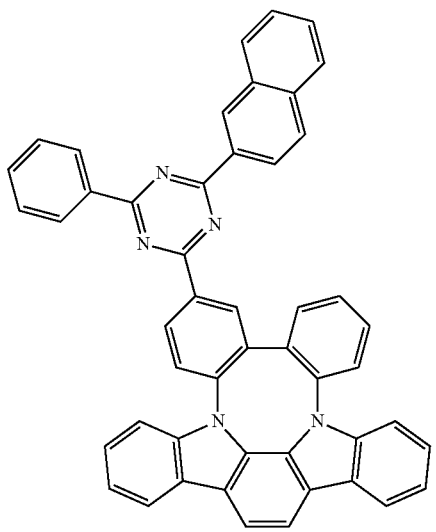
C-24
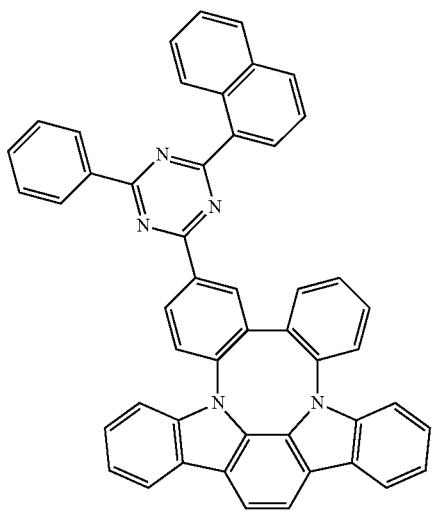
C-25
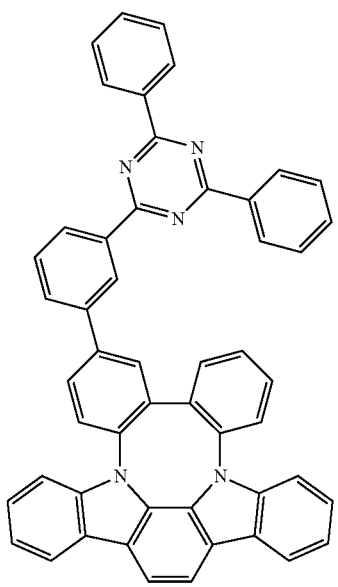
C-26
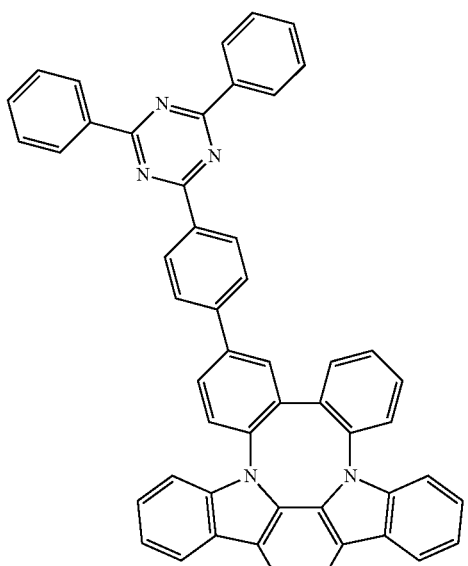
C-27
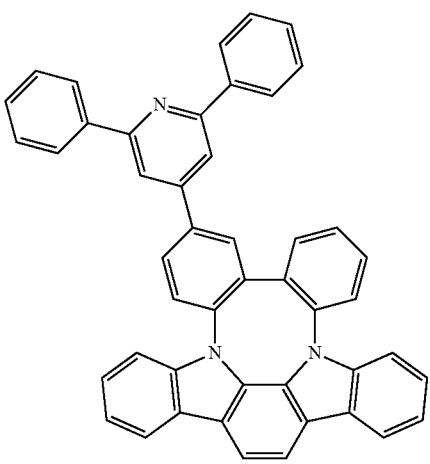
C-28
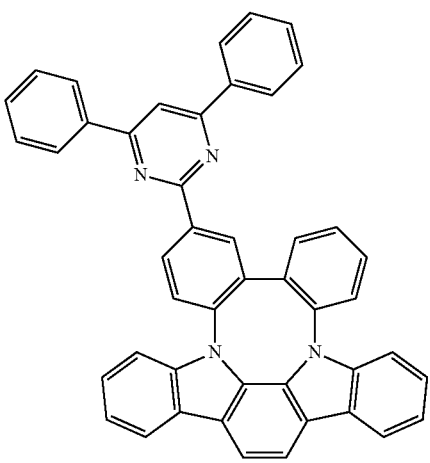

C-29
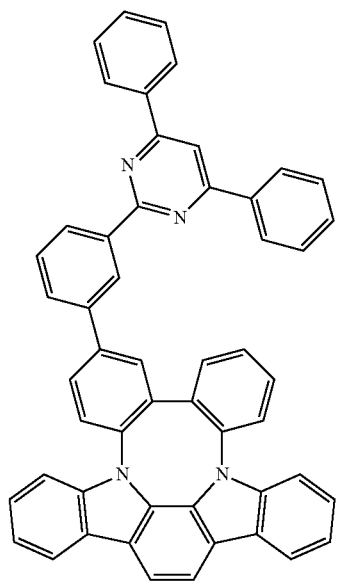
C-30
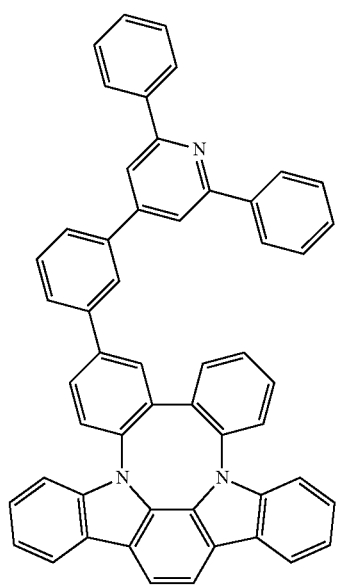
C-31
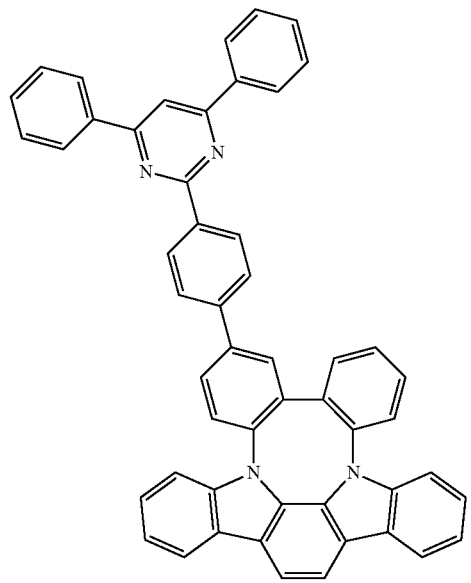
C-32
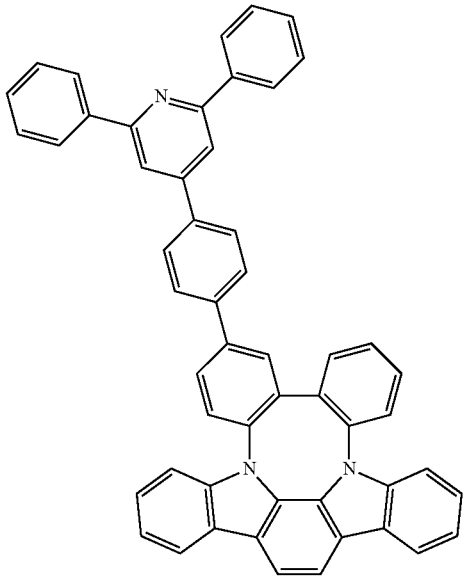

C-33
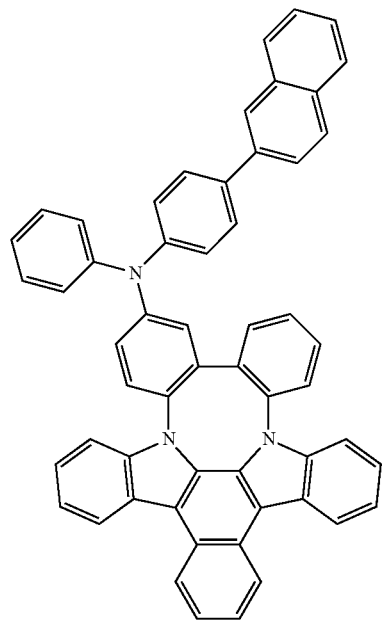
C-34
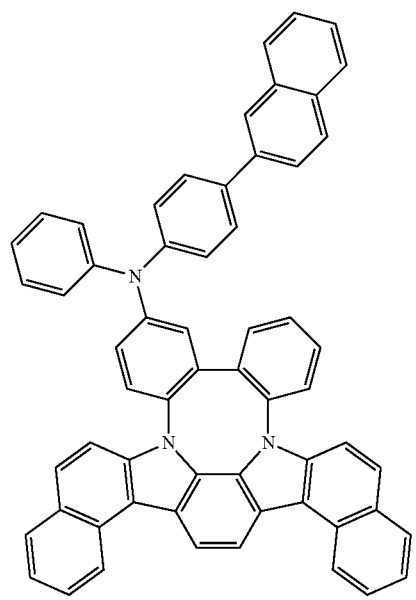
C-35
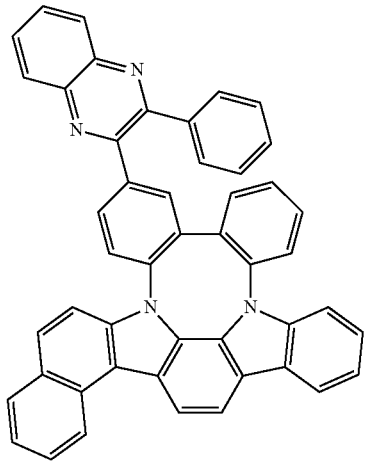
C-36
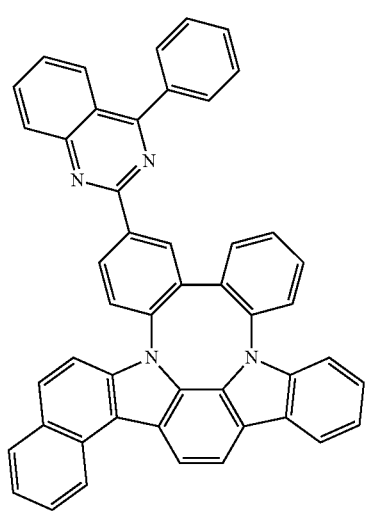
C-37
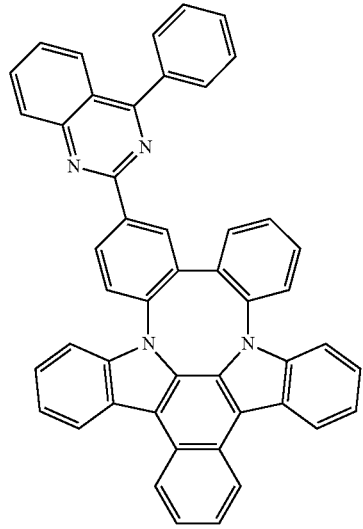

C-38
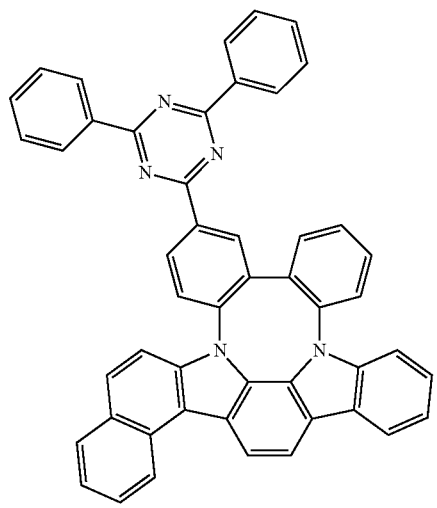
C-39
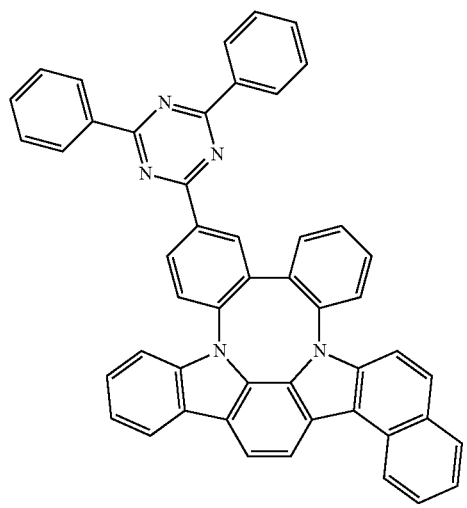
C-40
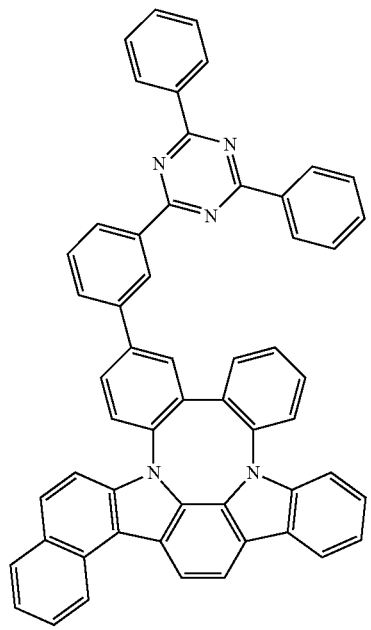
C-41
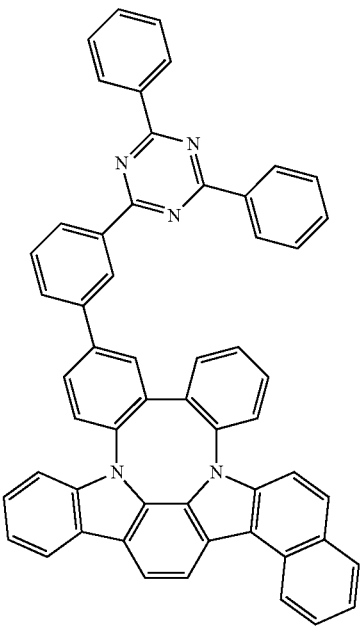
C-42
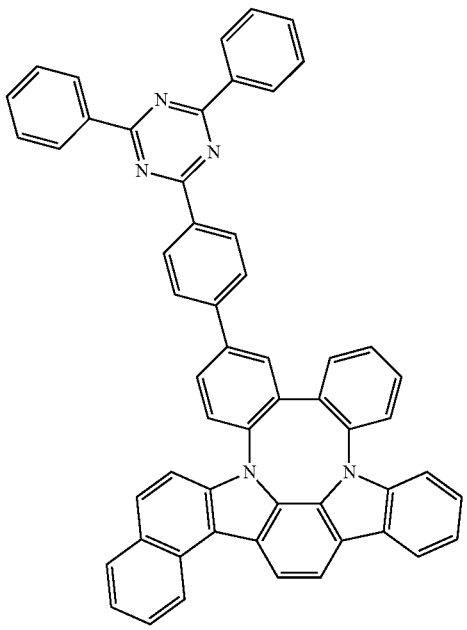

C-43
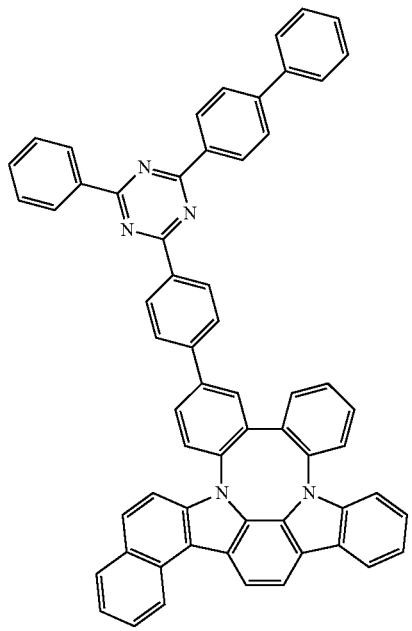
C-44
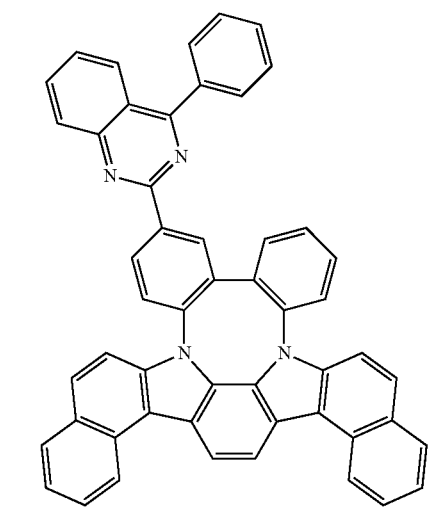
C-45
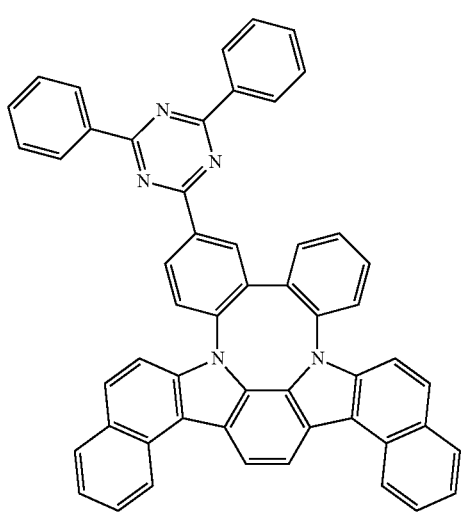
C-46
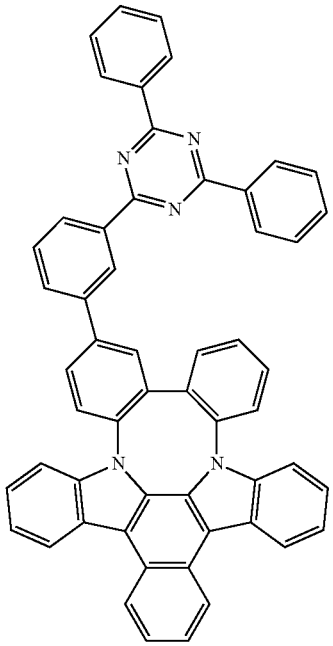
C-47
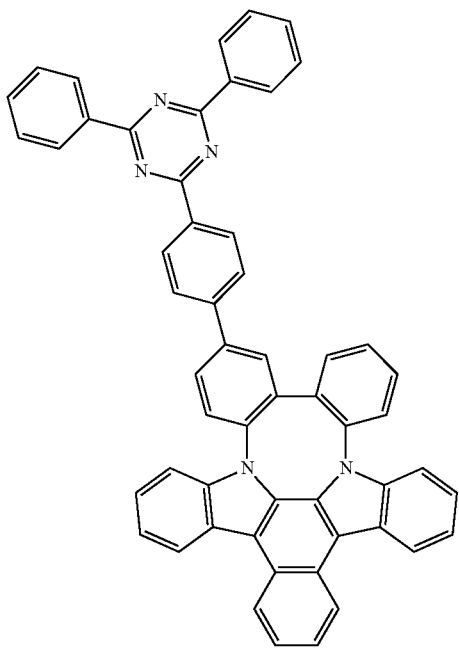
C-48
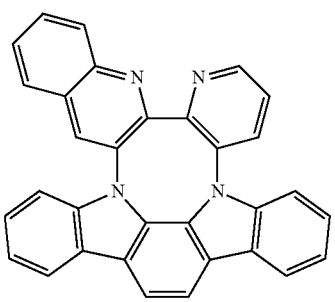

-continued
C-49
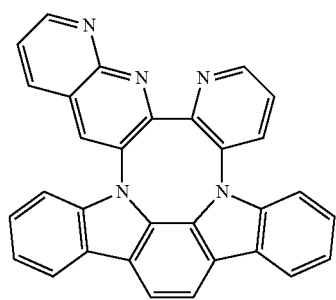
C-50
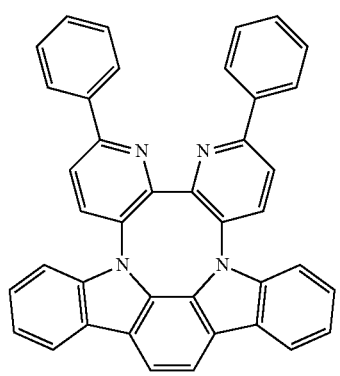
C-51
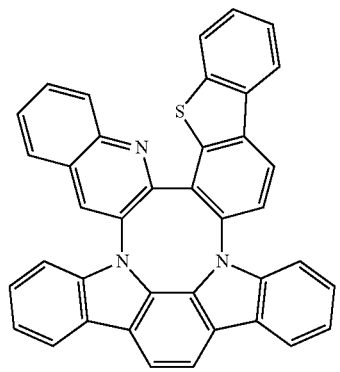
C-52
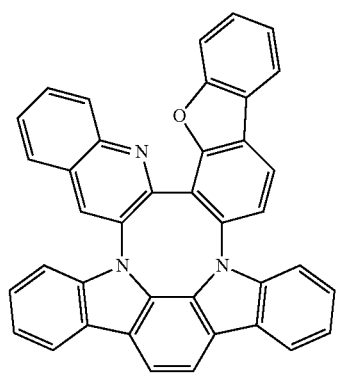
-continued
C-53
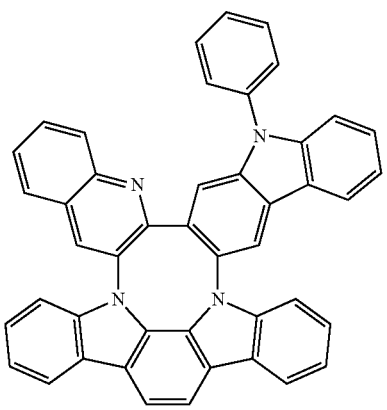
C-54
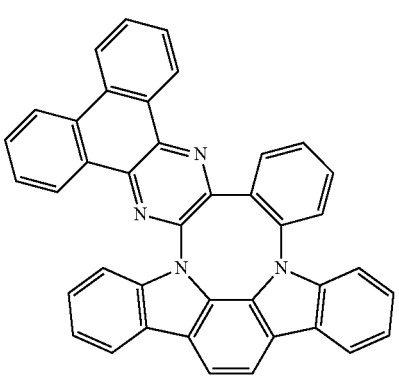
C-55
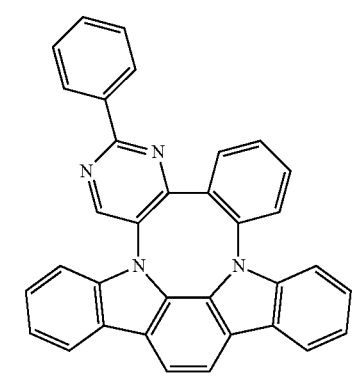
C-56
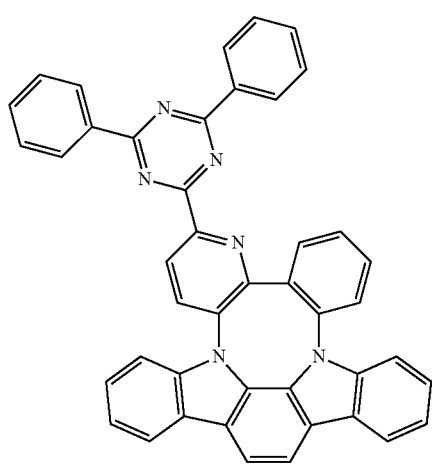

C-57
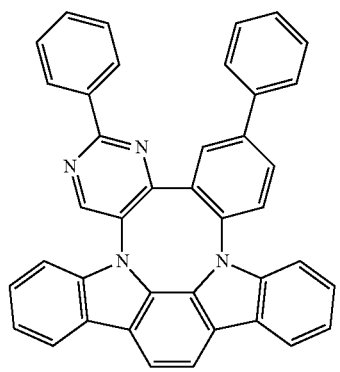
C-60
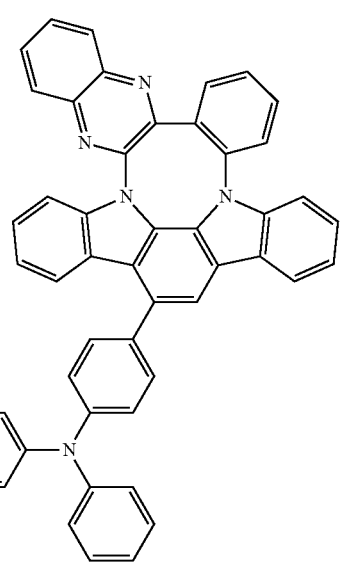
C-58
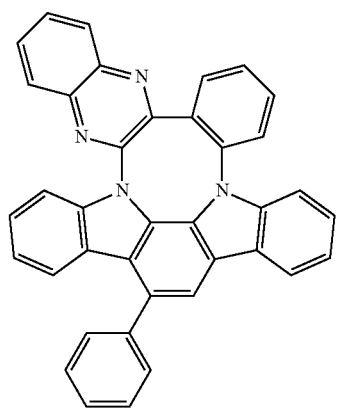
C-61
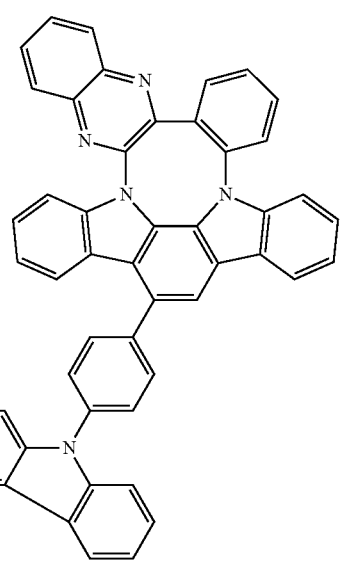
C-59
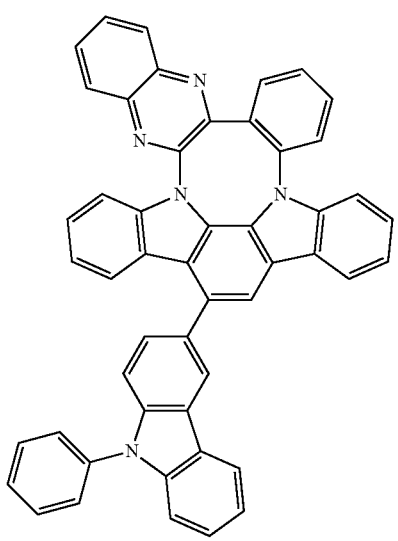
C-62
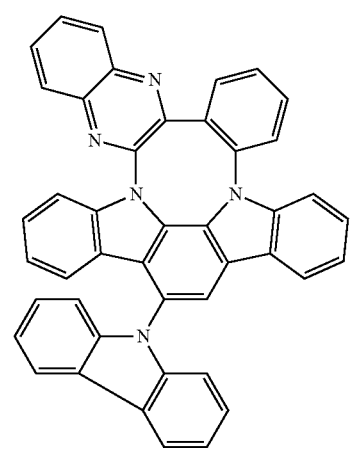

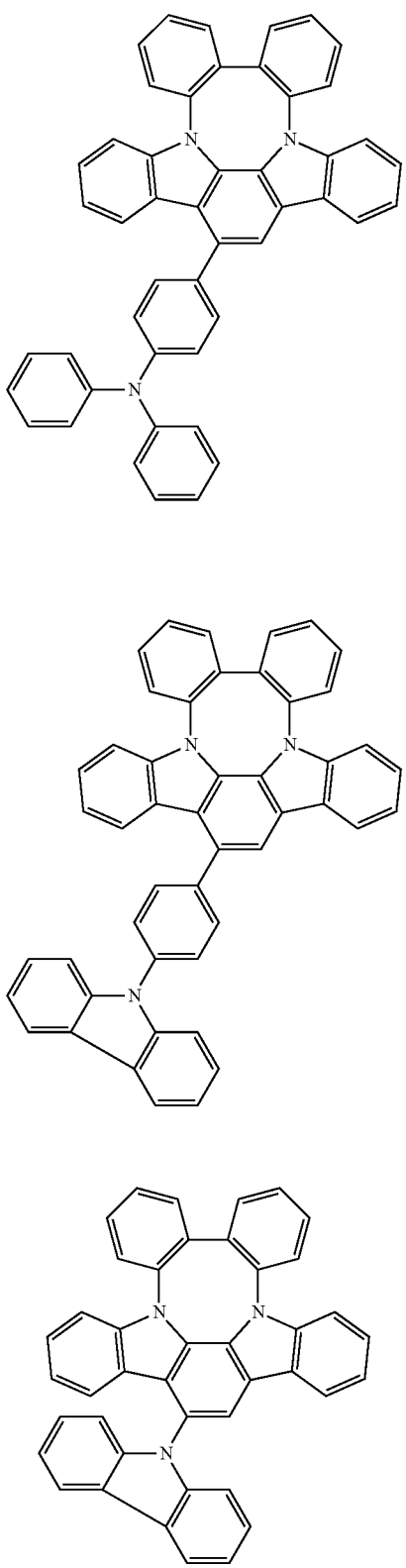

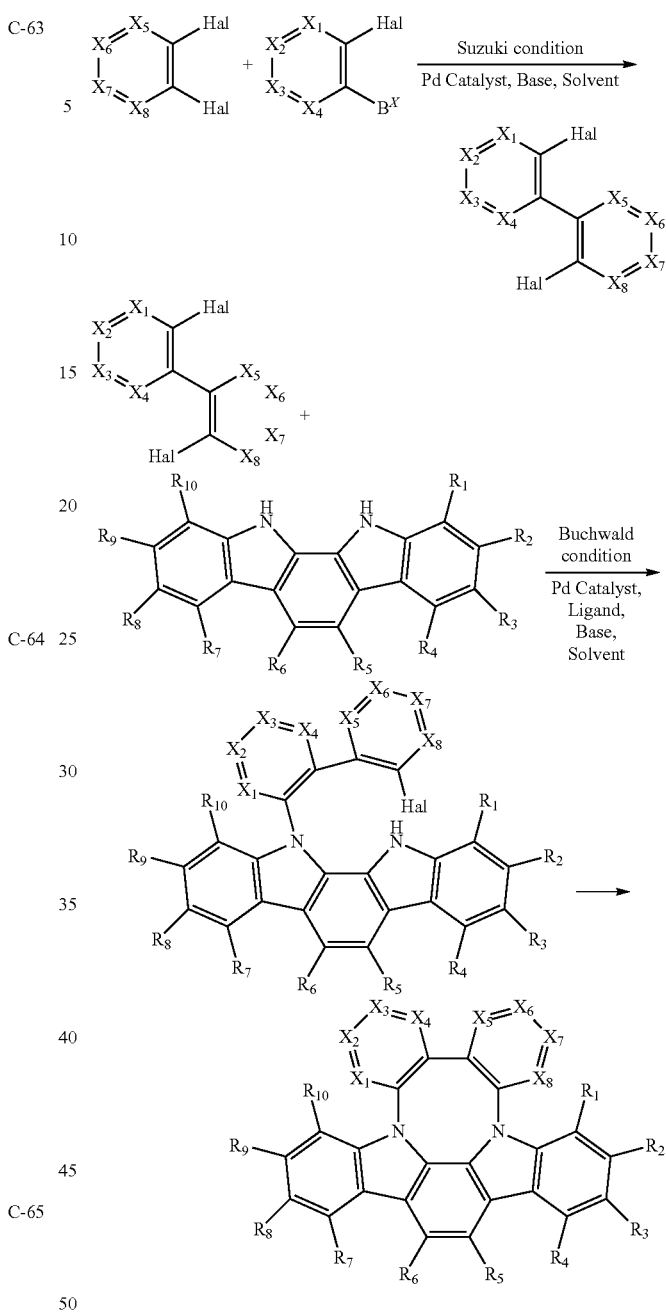

The organic electroluminescent compound according to the present disclosure can be prepared by known methods to one skilled in the art, and can be prepared, for example, according to the following reaction scheme 1:

The present disclosure further provides an organic electroluminescent material comprising the organic electroluminescent compound of formula 1, and an organic electroluminescent device comprising the organic electroluminescent material.

The organic electroluminescent material can be comprised of the organic electroluminescent compound of the present disclosure alone, or can further include conventional materials generally used in organic electroluminescent materials.

The organic electroluminescent device of the present disclosure may comprise a first electrode, a second electrode, and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, an electron transport layer, an electron buffer layer, an electron injection layer, an interlayer, a hole blocking layer, and an electron blocking layer.

The organic electroluminescent compound of formula 1 of the present invention can be comprised in the light-emitting layer as a host material. Preferably, the light-emitting layer may comprise at least one dopant. If necessary, another compound besides the organic electroluminescent compound of formula 1 may be comprised as a second host material.

Another embodiment of the present invention provides a material for producing an organic electroluminescent device. The material comprises the first host material and the second host material, and the first host material comprises the organic electroluminescent compound of the present invention. Herein, the weight ratio of the first host material to the second host material is in the range of 1:99 to 99:1.

The second host material can be any of the known phosphorescent hosts. Preferably, the second host material may be selected from the group consisting of the compounds of formulae 2 to 6 below.

$$H-(Cz-L_4)_i-M \quad (2)$$

$$H-(Cz)_j-L_4-M \quad (3)$$

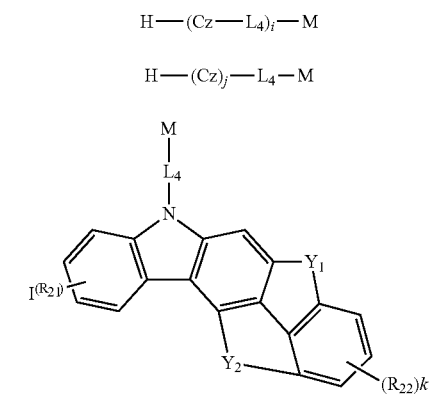

(4)

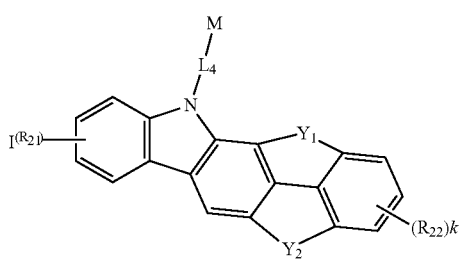

(5)

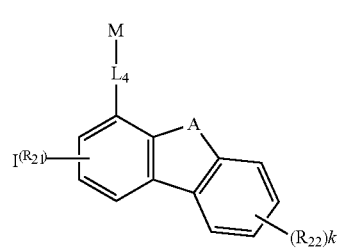

(6)

wherein Cz represents the following structure:

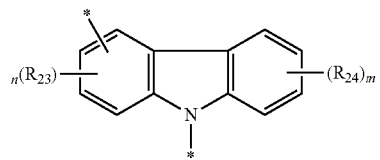

A represents —O— or —S—;

$R_{21}$ to $R_{24}$, each independently, represent hydrogen, deuterium, a halogen, a substituted or unsubstituted (C1-C30) alkyl, a substituted of unsubstituted (C6-C30)aryl, a substituted or unsubstituted (5- to 30-membered)heteroaryl, or —SiR$_{25}$R$_{26}$R$_{27}$;

$R_{25}$ to $R_{27}$, each independently, represent a substituted or unsubstituted (C1-C30)alkyl, or a substituted or unsubstituted (C6-C30)aryl;

La represents a single bond, a substituted or unsubstituted (C6-C30)arylene, or a substituted or unsubstituted (5- to 30-membered)heteroarylene;

M represents a substituted or unsubstituted (C6-C30)aryl, or a substituted or unsubstituted (5- to 30-membered)heteroaryl;

$Y_1$ and $Y_2$, each independently, represent —O—, —S—, —N(R$_{41}$)—, or —C(R$_{42}$)(R$_{43}$)—, provided that $Y_1$ and $Y_2$ do not simultaneously exist;

$R_{41}$ to $R_{43}$, each independently, represent a substituted or unsubstituted (C1-C30)alkyl, a substituted or unsubstituted (C6-C30)aryl, or a substituted or unsubstituted (5- to 30-membered)heteroaryl, and $R_{42}$ and $R_{43}$ may be the same or different;

i and j, each independently, represent an integer of 1 to 3;

k, l, m, and n, each independently, represent an integer of 0 to 4; and where i, j, k, l, m, or n is an integer of 2 or more, each of (Cz-L$_4$), each of (Cz), each of R$_{21}$, each of R$_{22}$, each of R$_{23}$, or each of R$_{24}$ may be the same or different.

Specifically, preferable examples of the second host material are as follows:

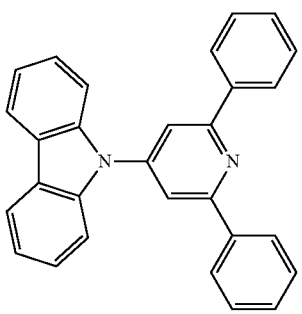

-continued
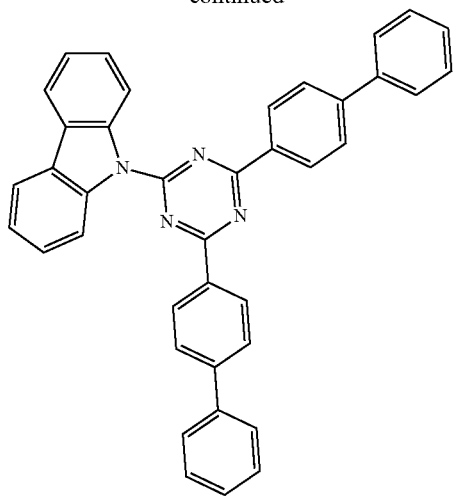
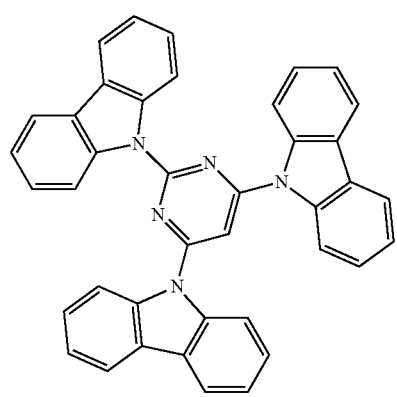
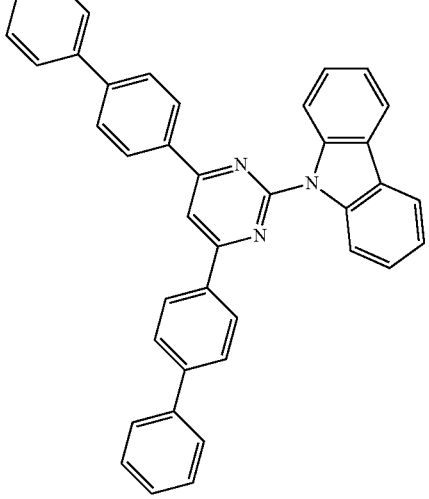
-continued
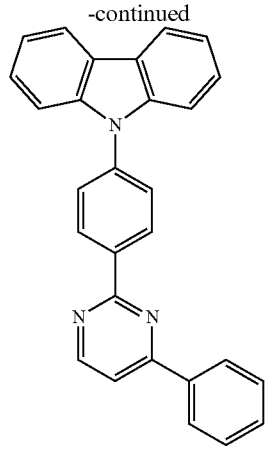
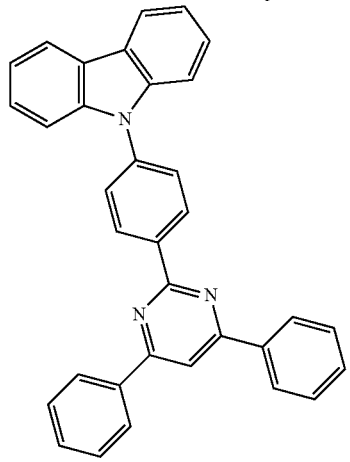
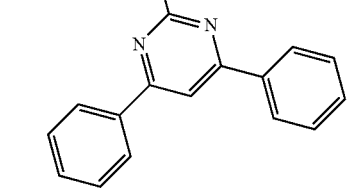
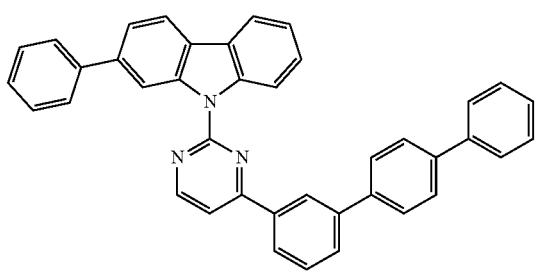
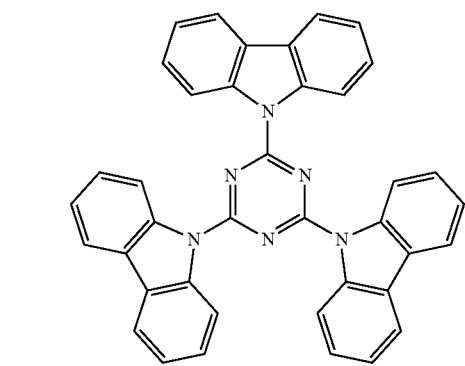

31
-continued
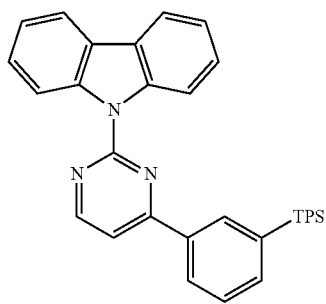
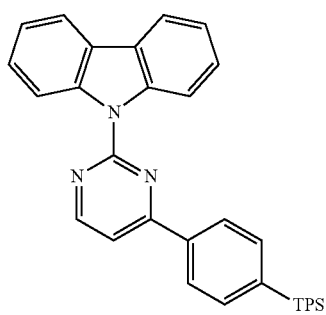
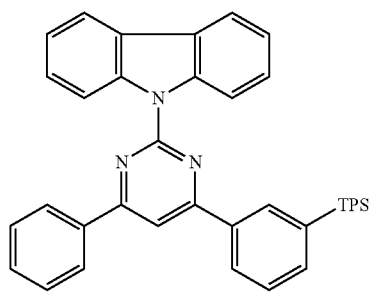
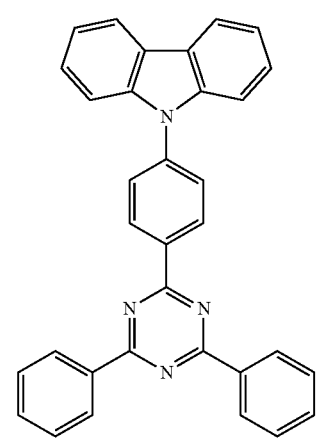
32
-continued
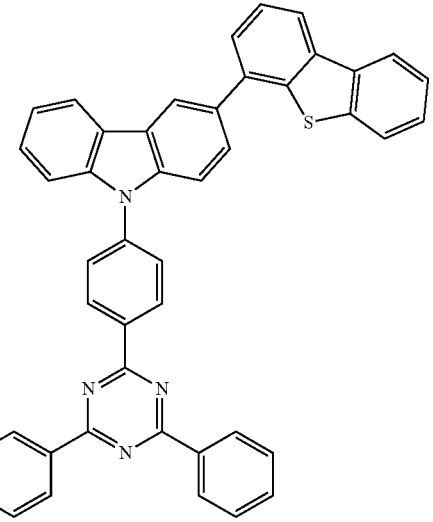
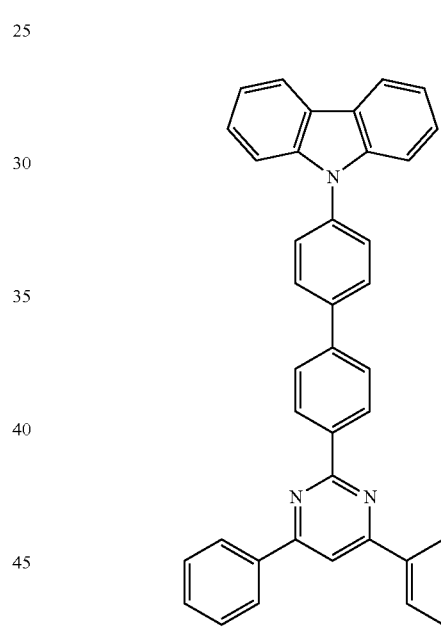
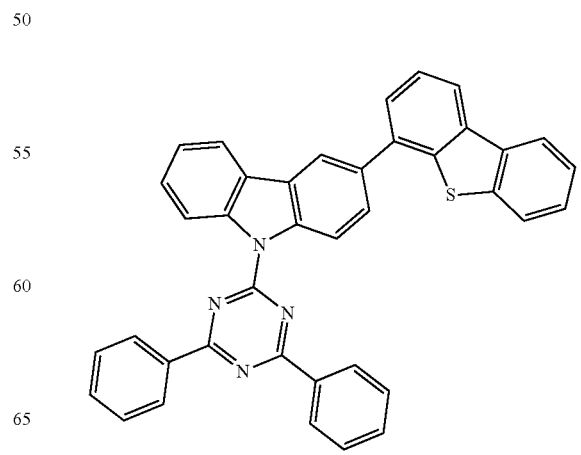

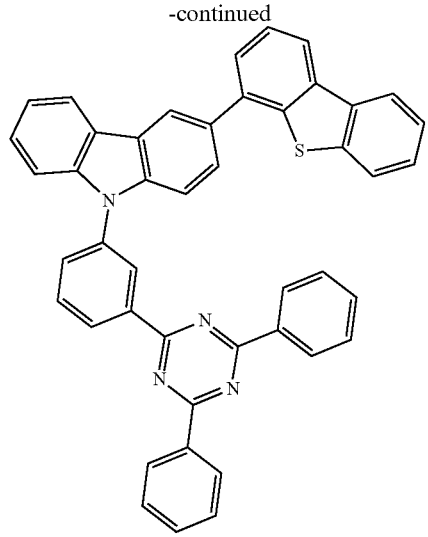
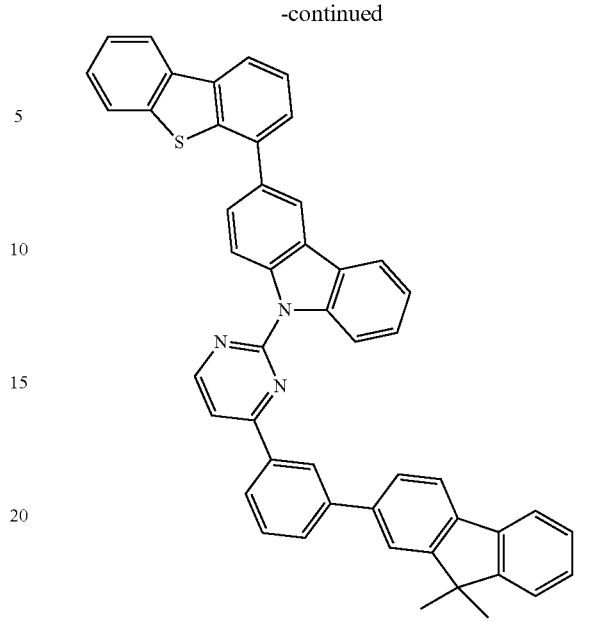
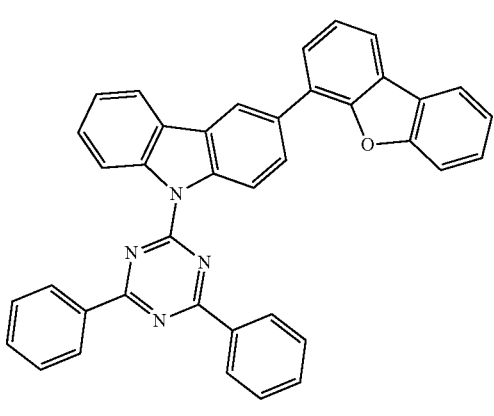
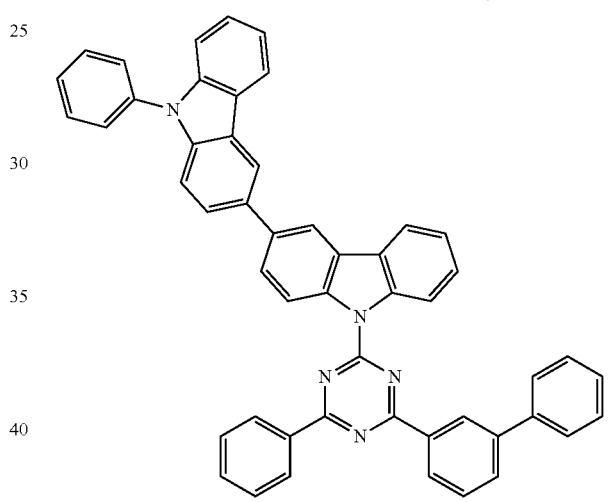
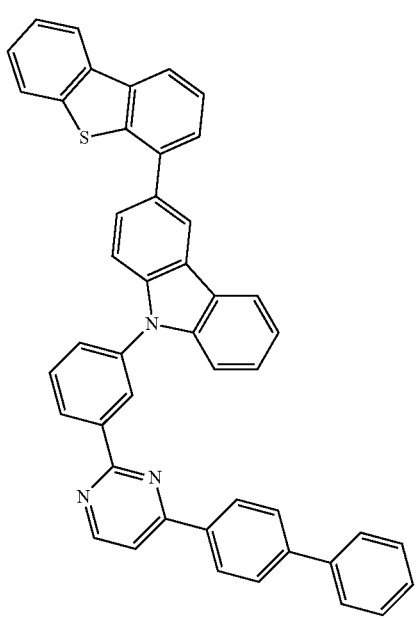
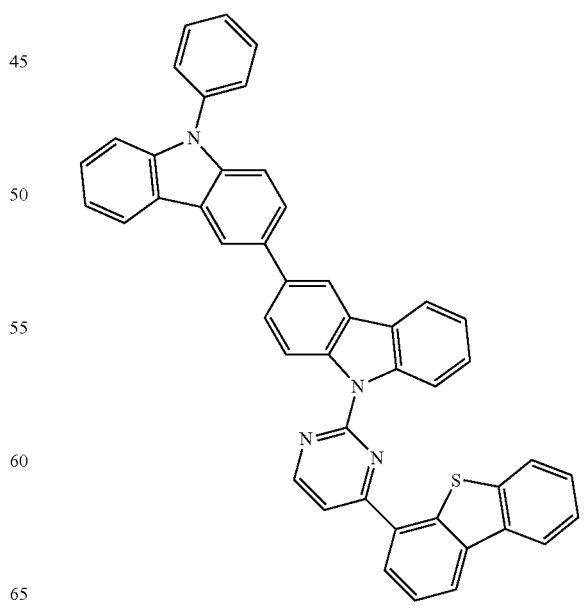

-continued
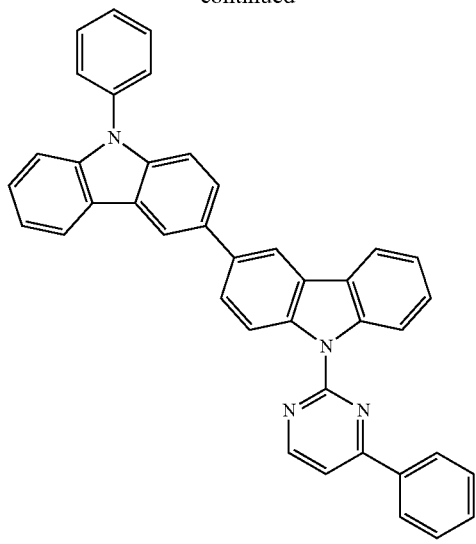
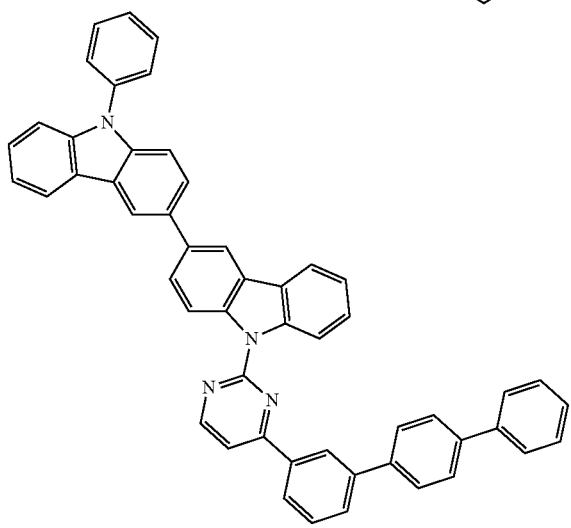
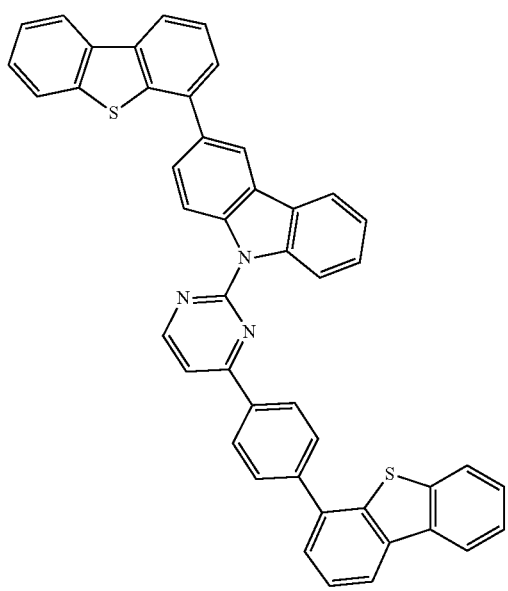
-continued
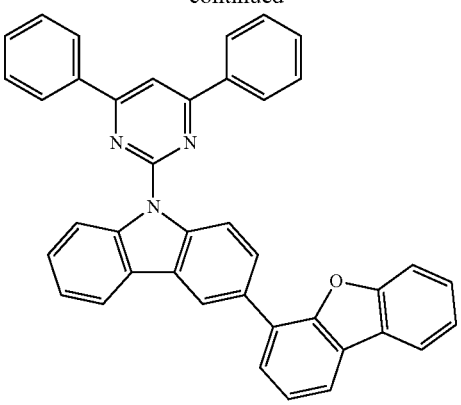
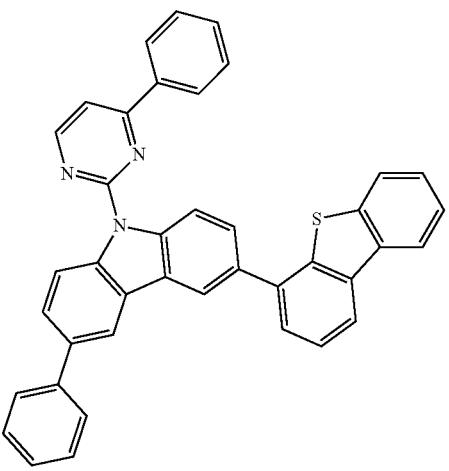
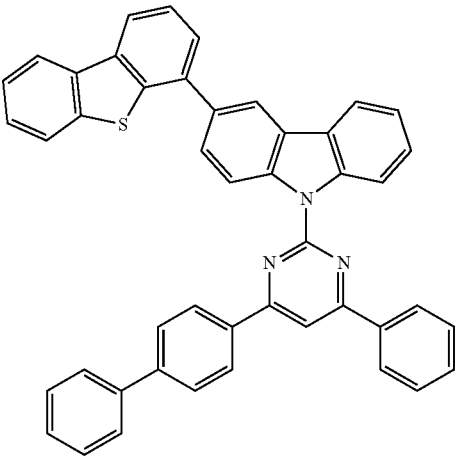

37
-continued
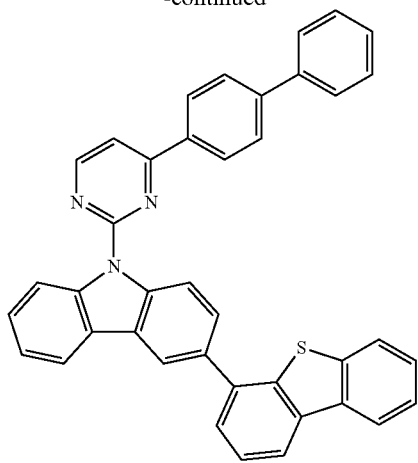
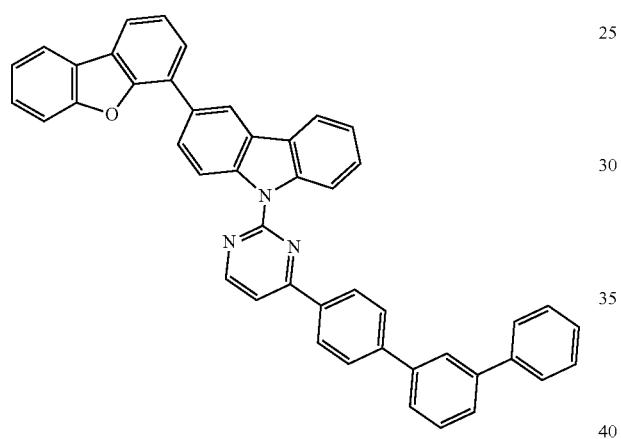
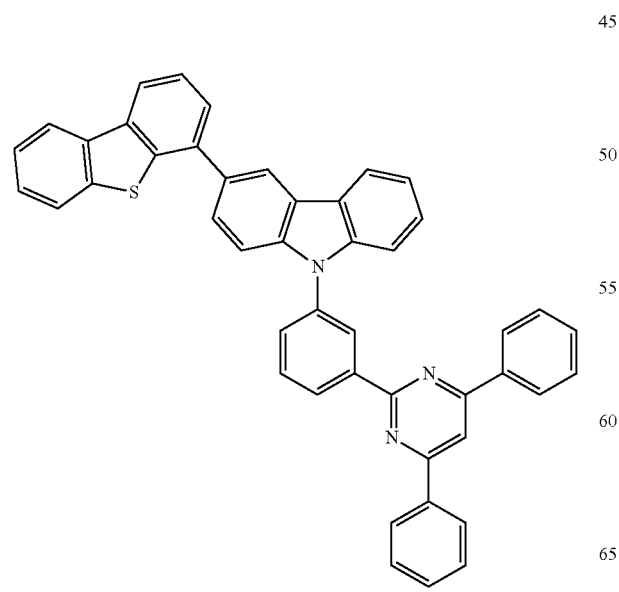
38
-continued
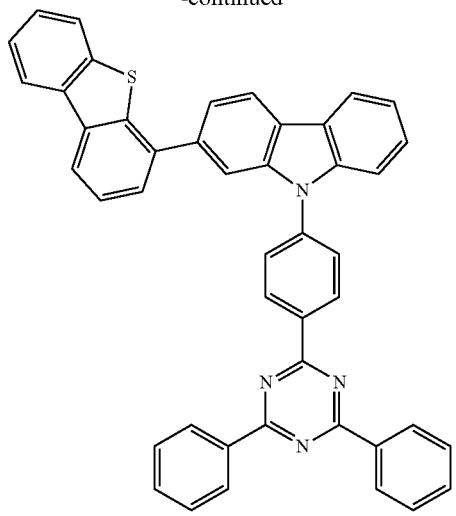
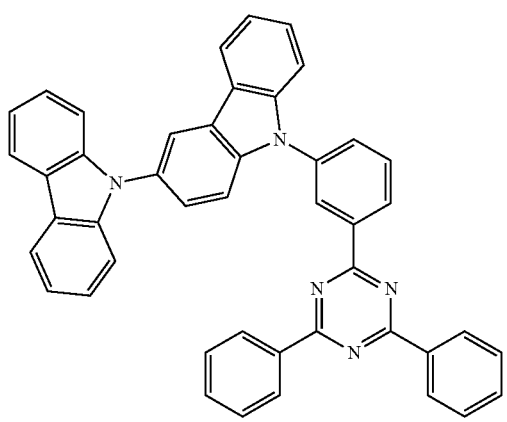
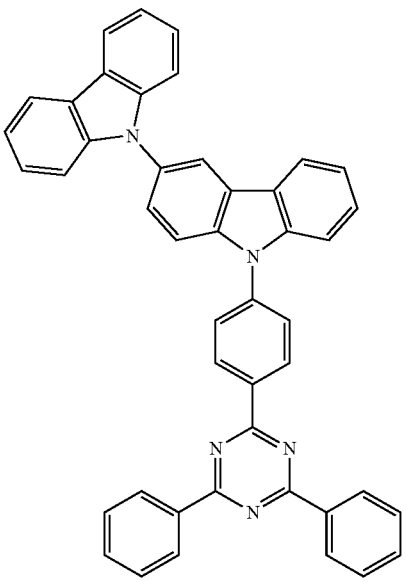

39
-continued
40
-continued
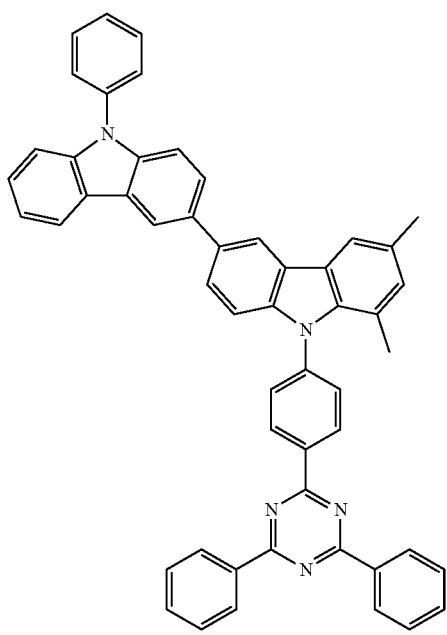
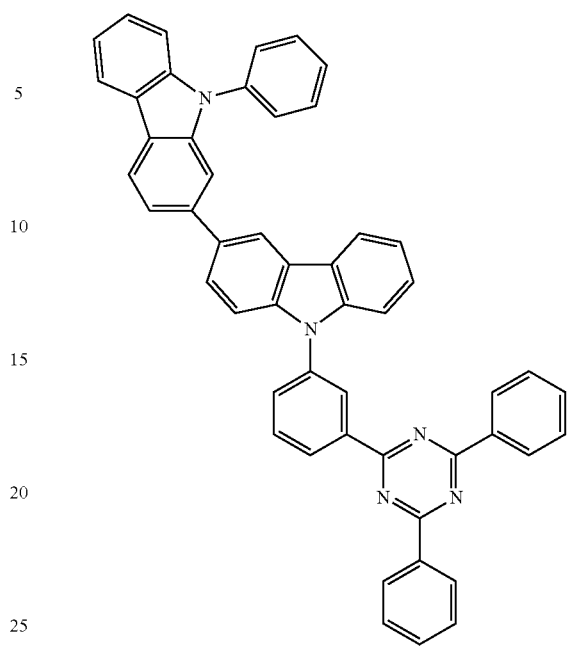
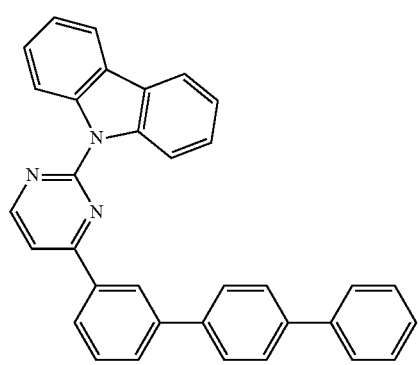
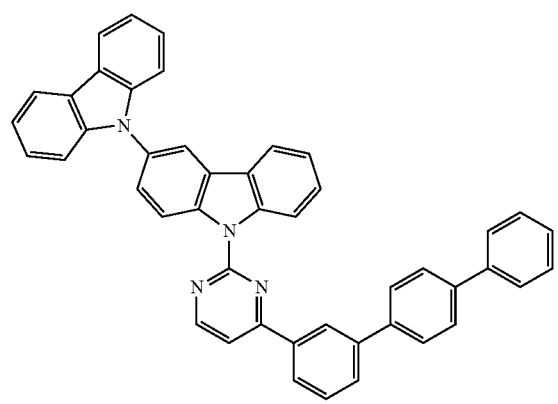
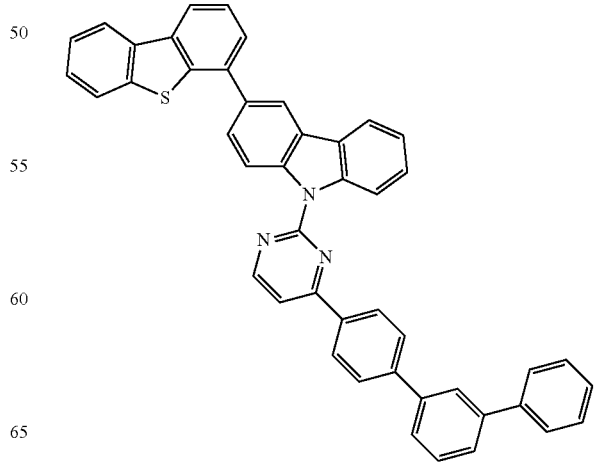

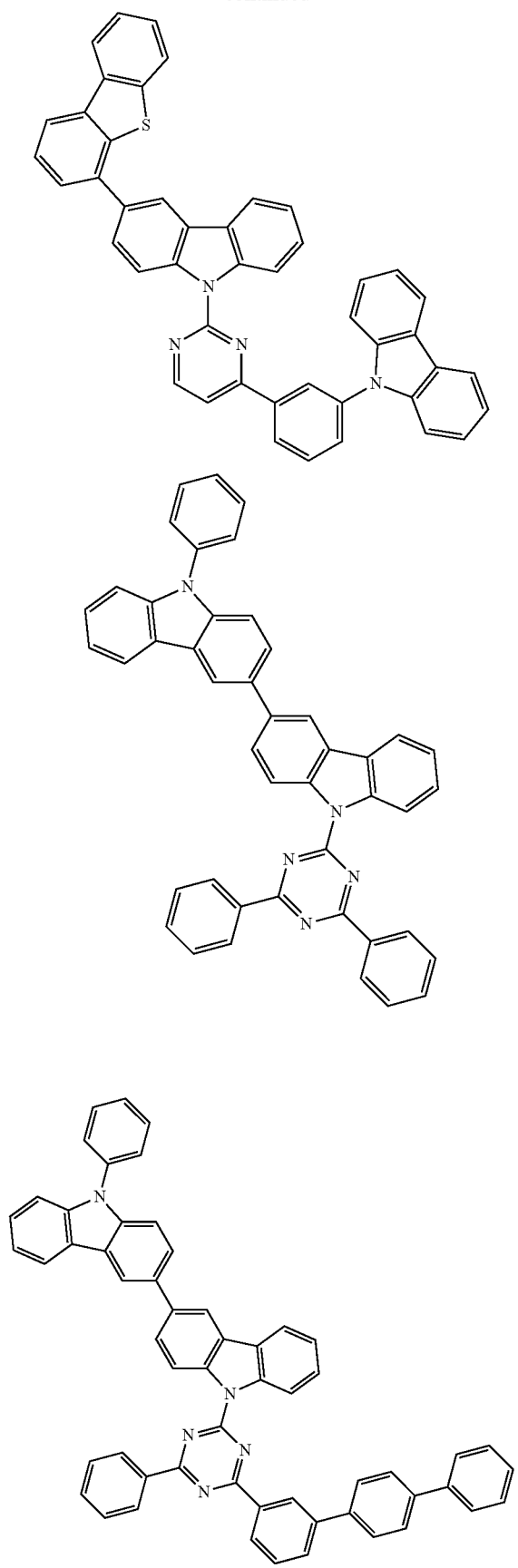
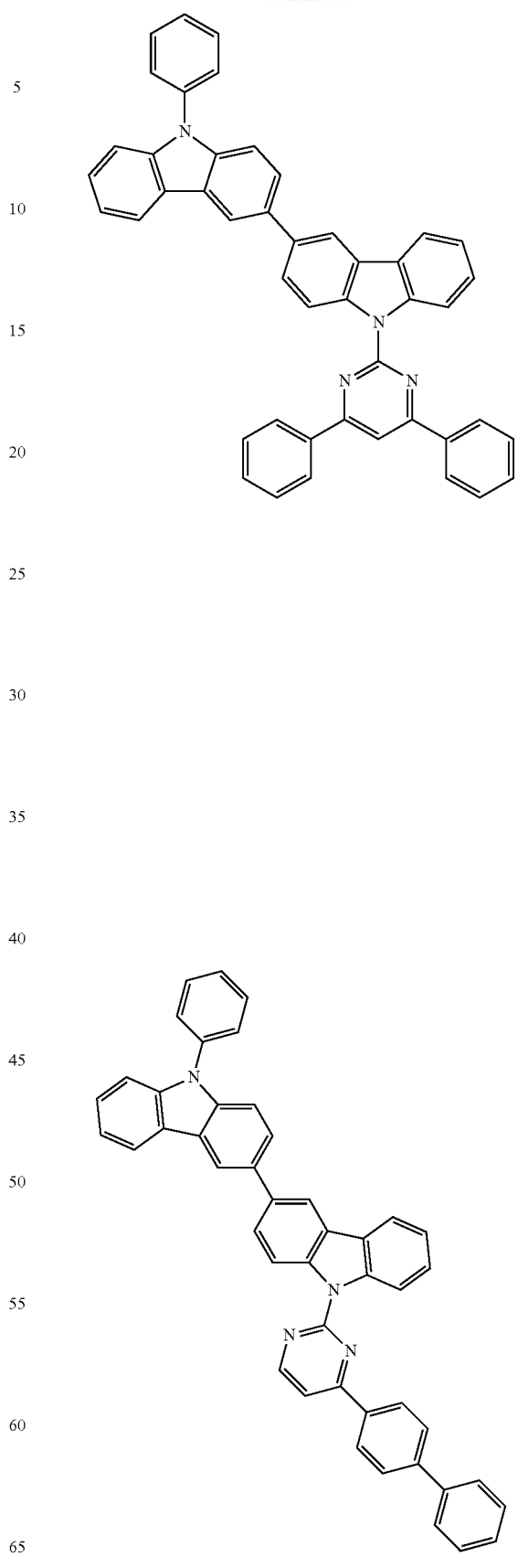

43
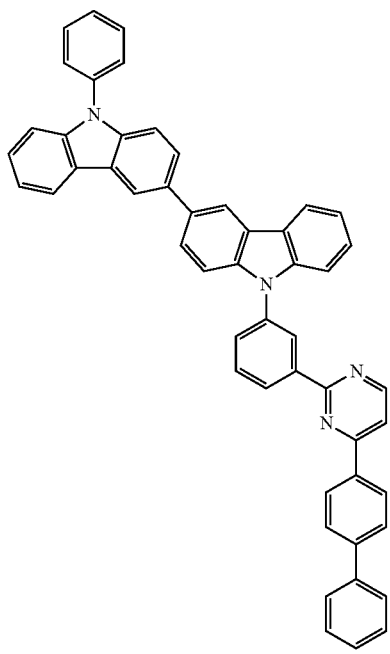
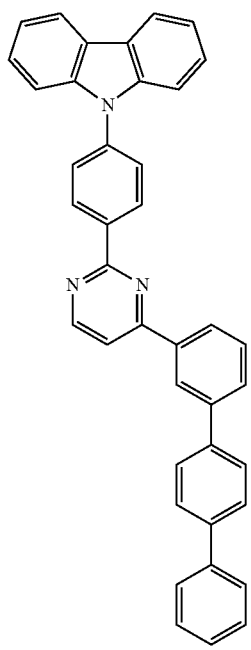
44
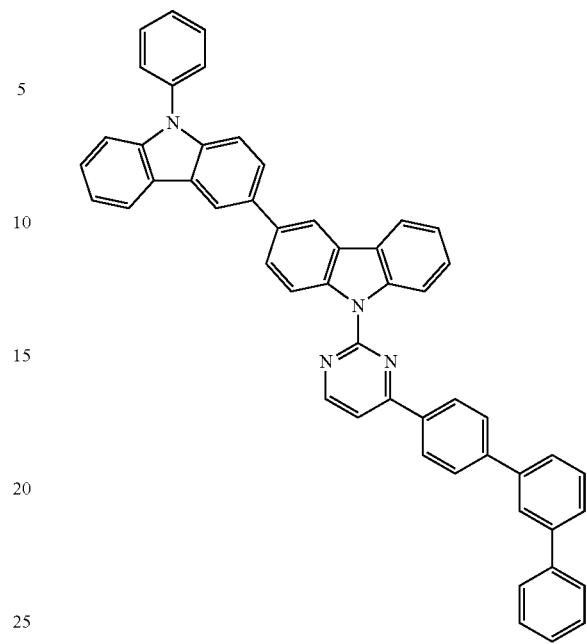
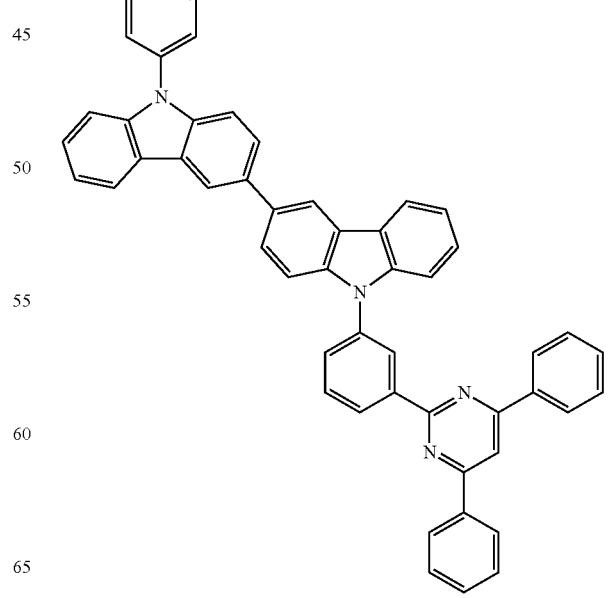

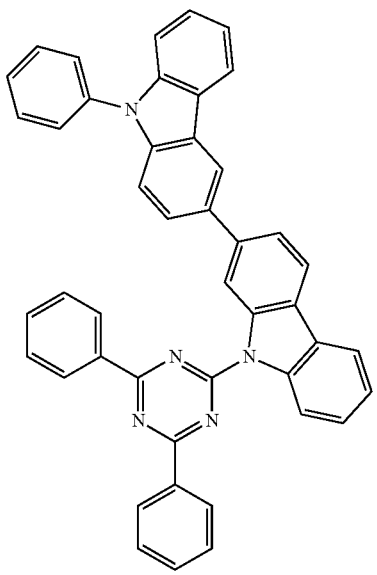
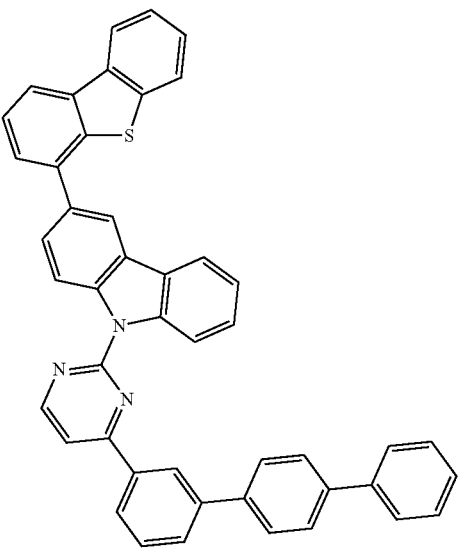
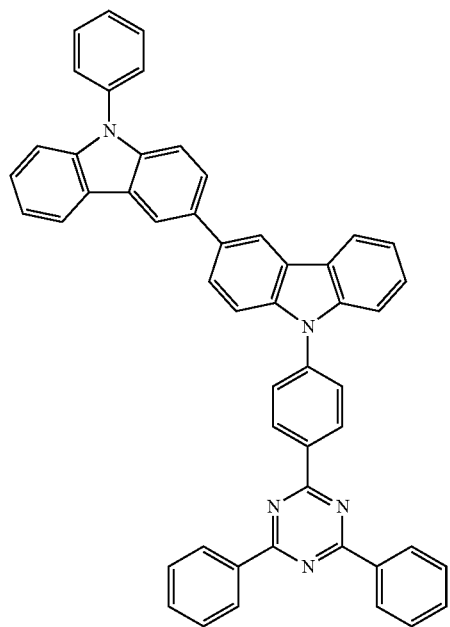
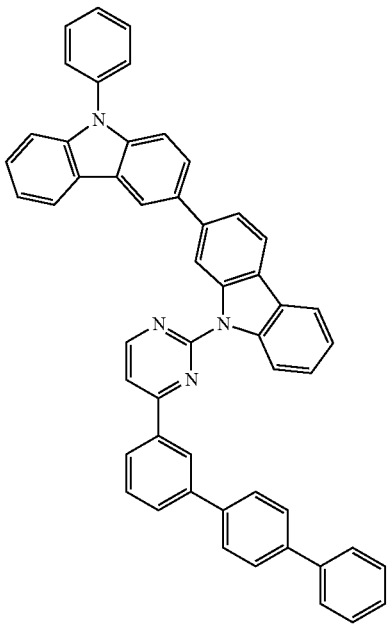

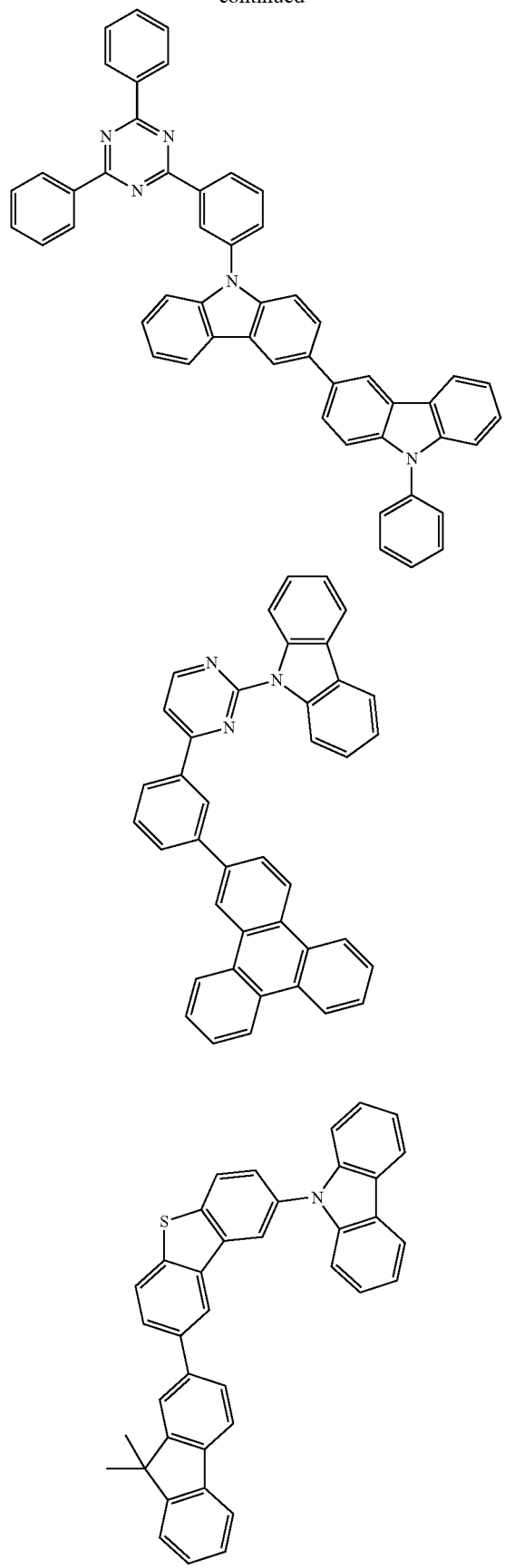
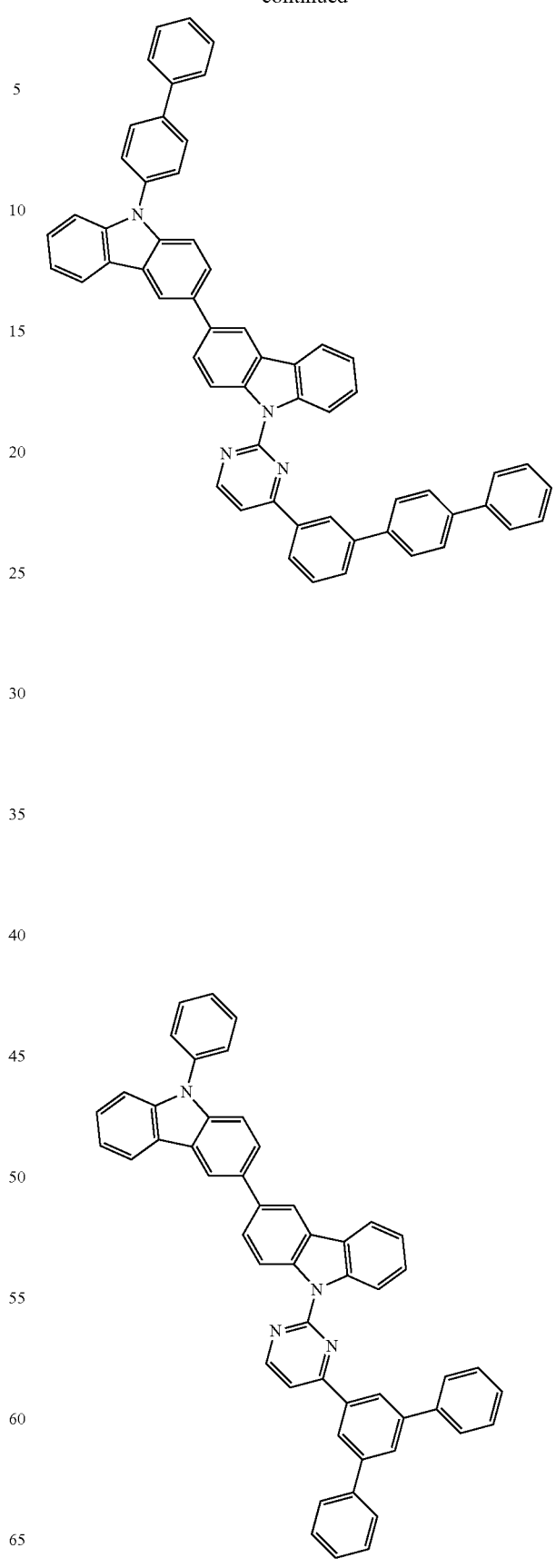

-continued
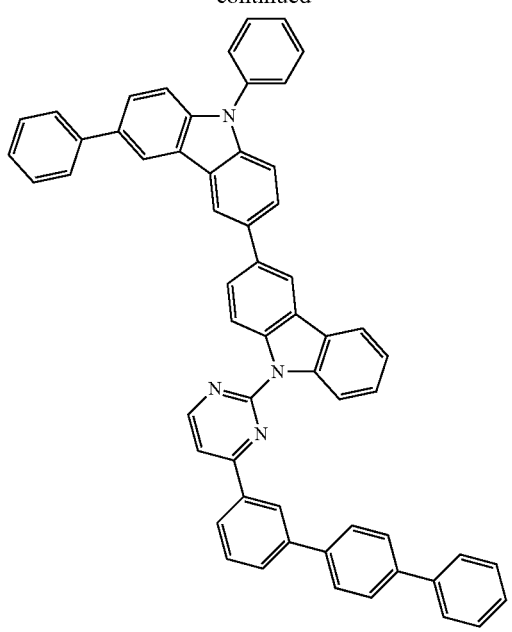
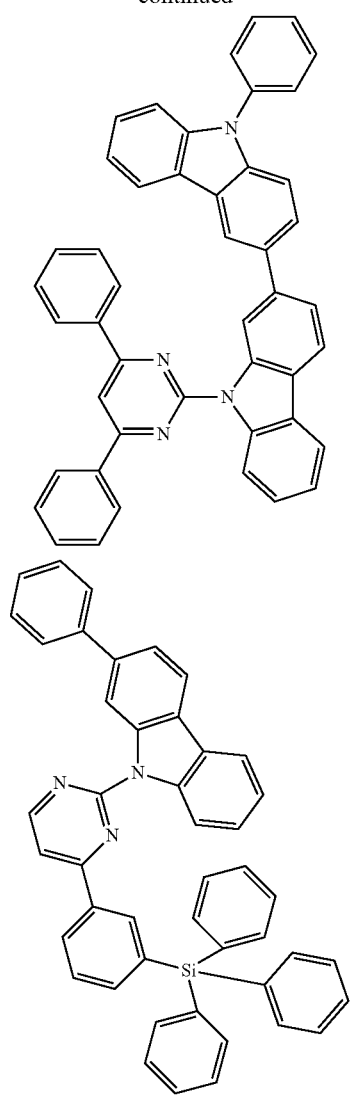
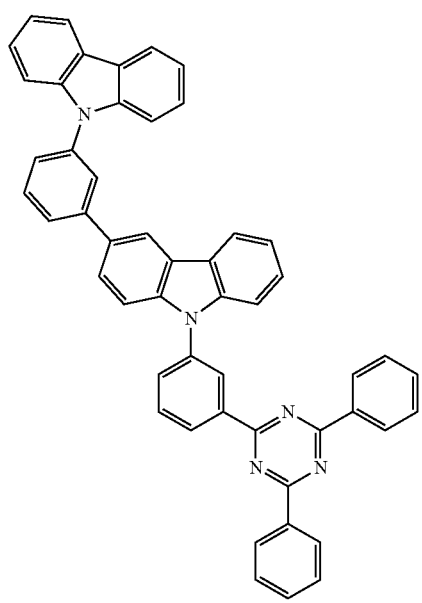

51
-continued
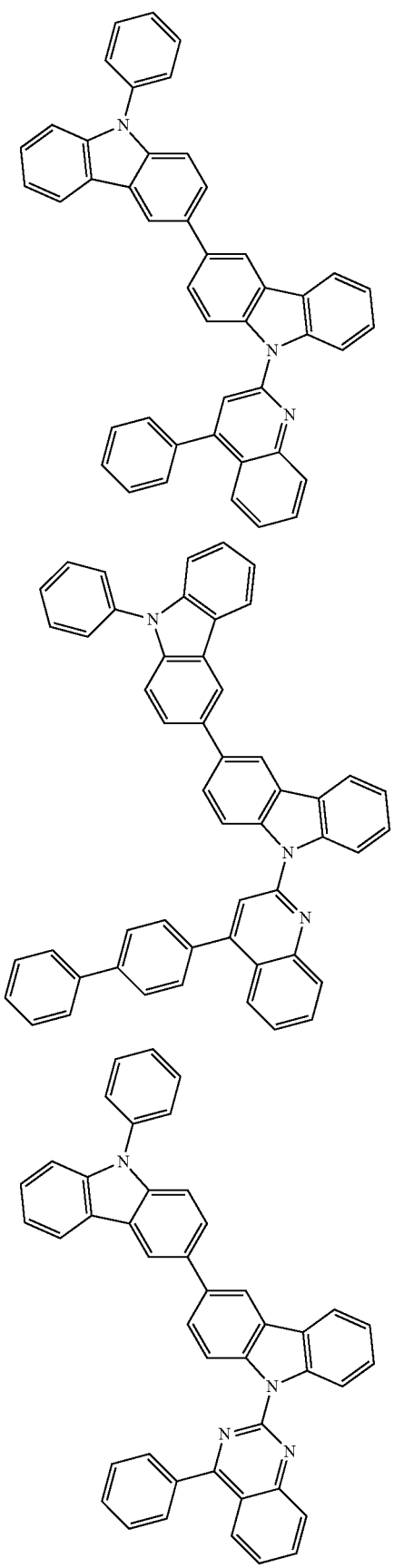
52
-continued
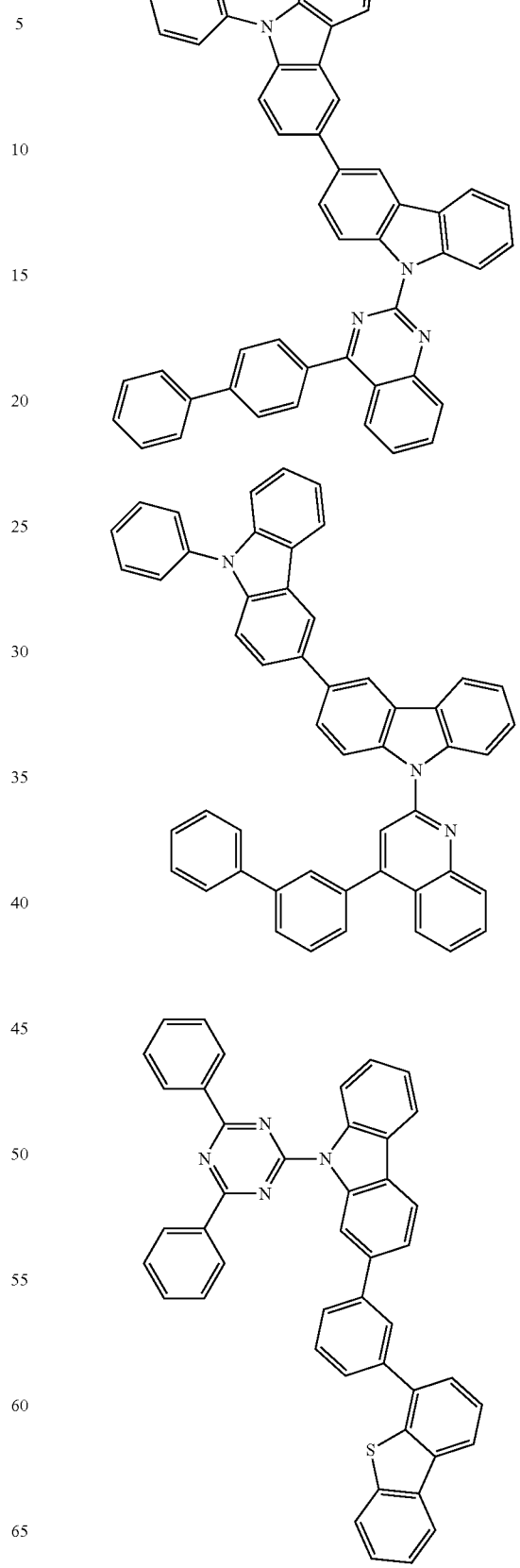

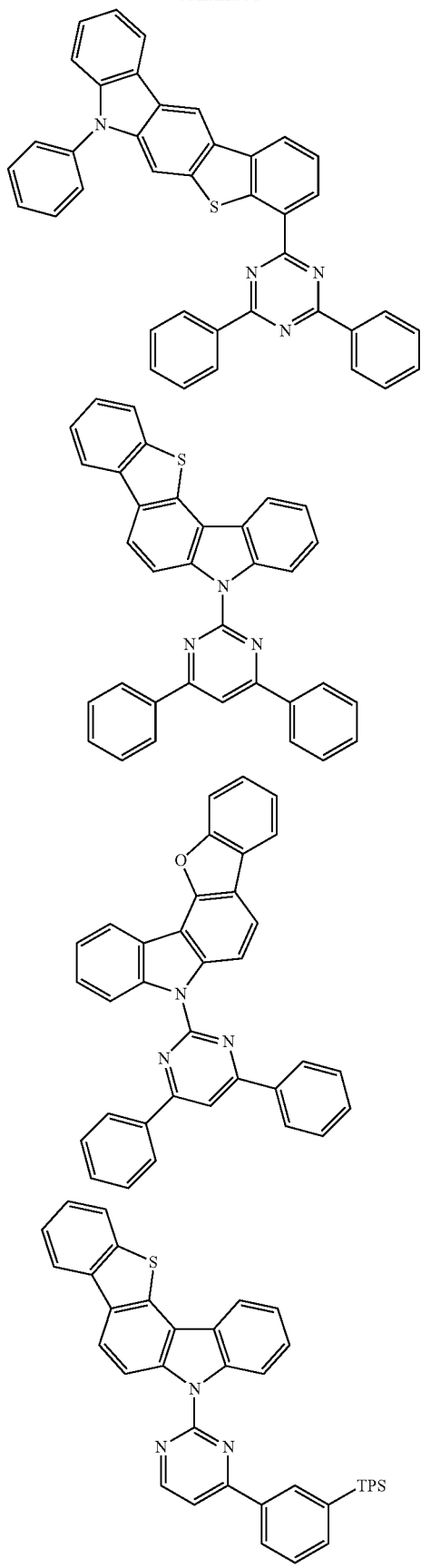
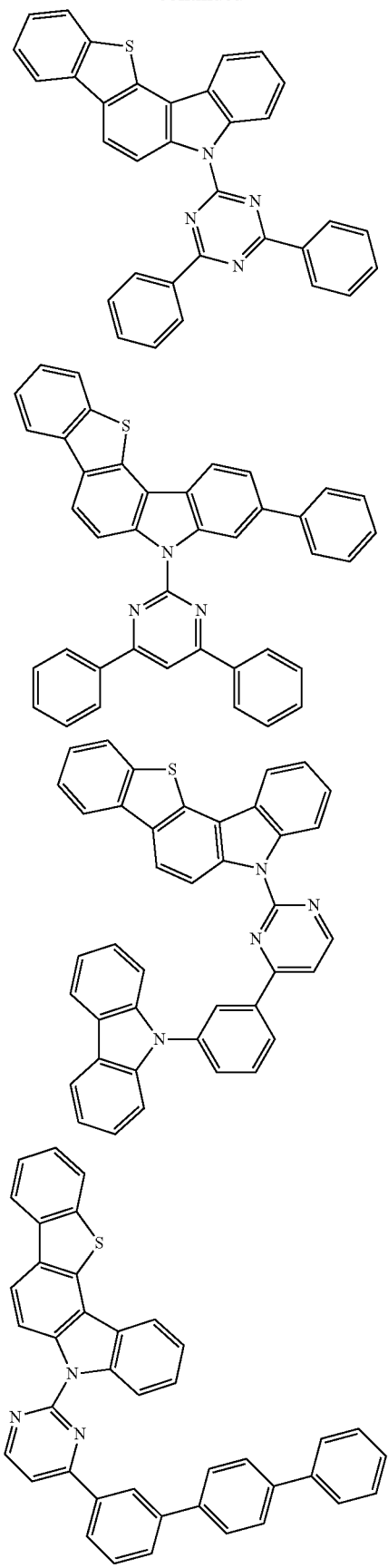

55
-continued
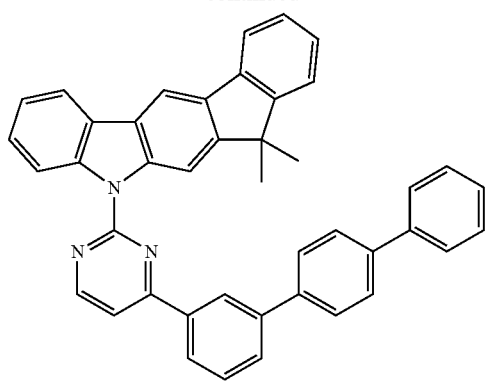
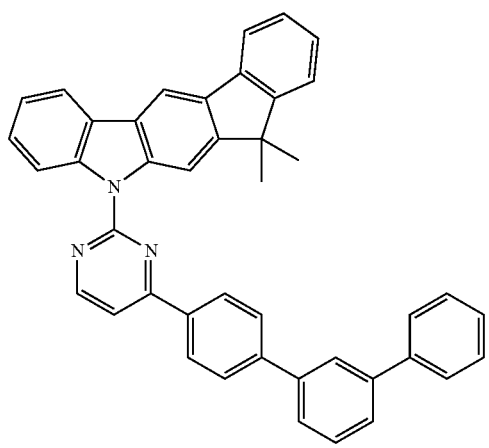
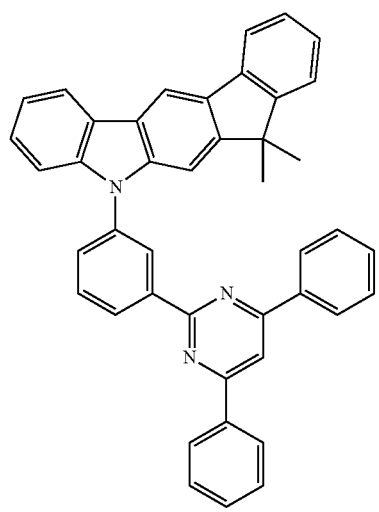
56
-continued
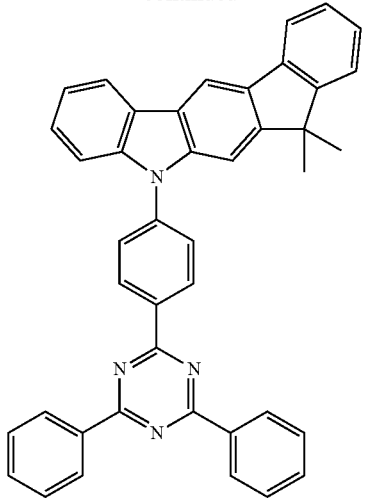
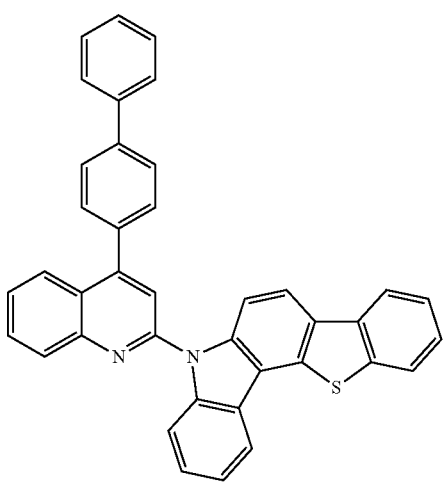
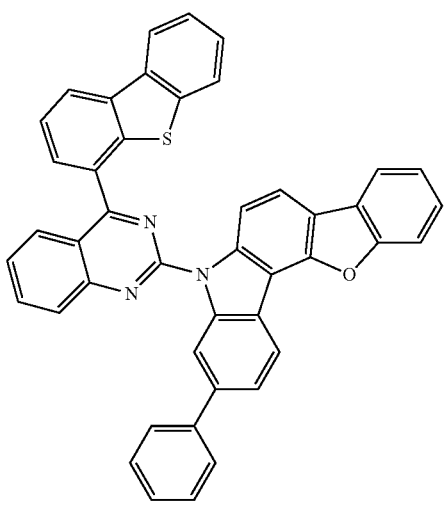

57
-continued
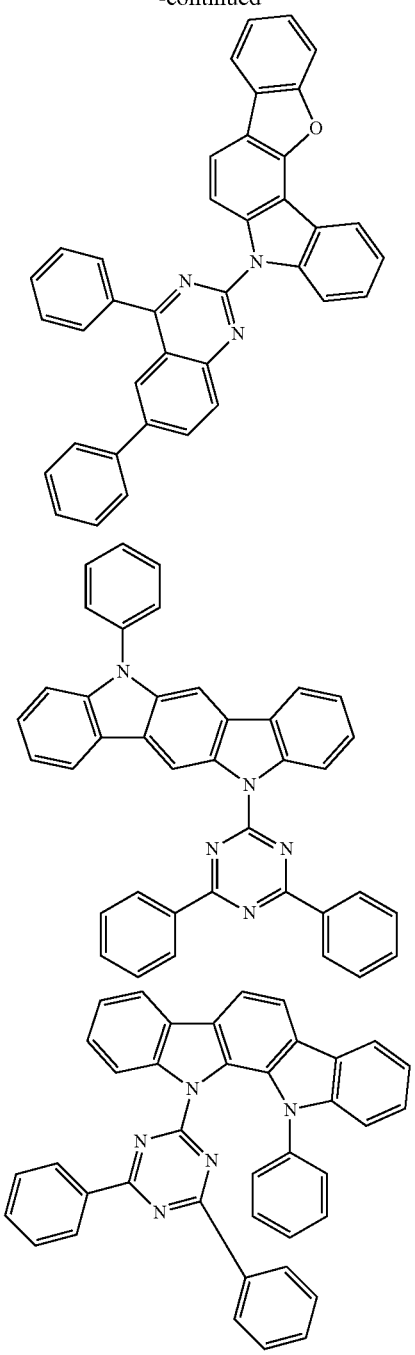
58
-continued
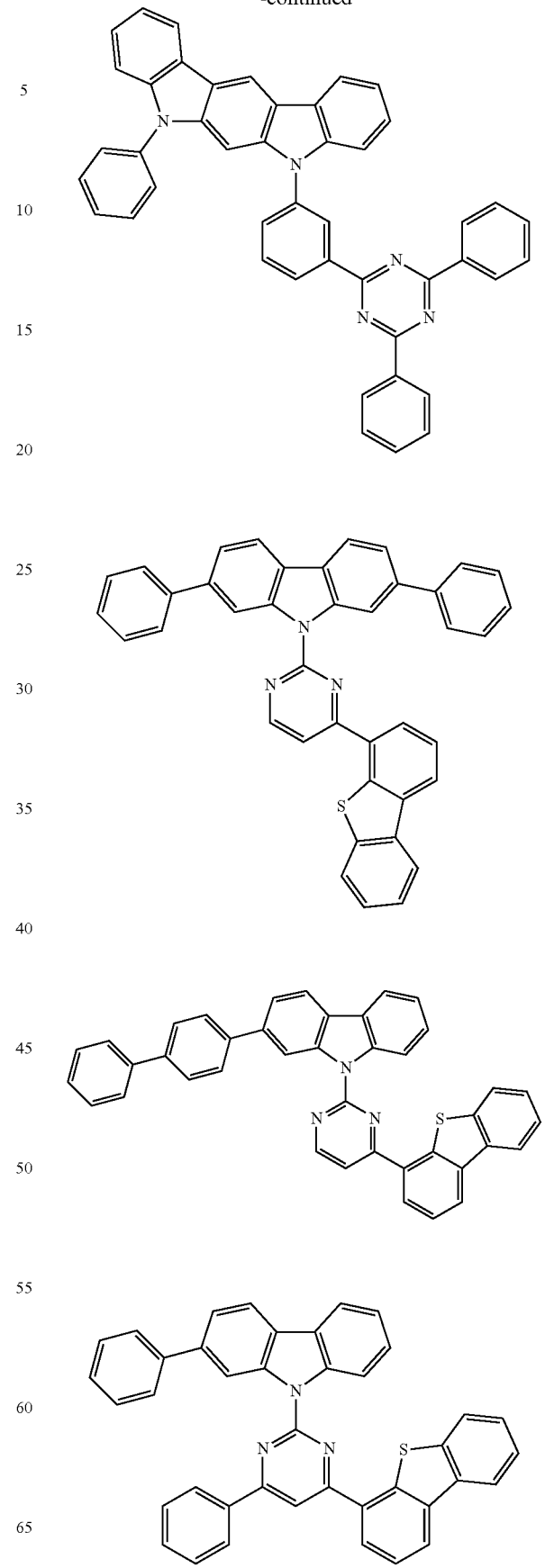

59
-continued
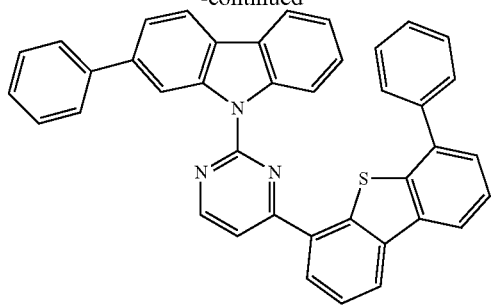
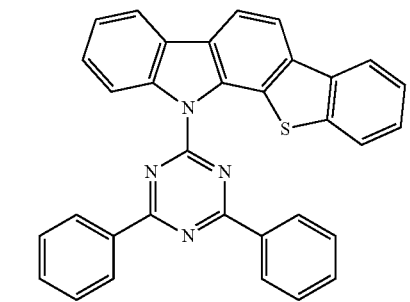
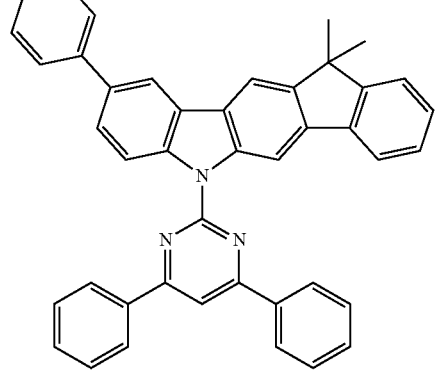
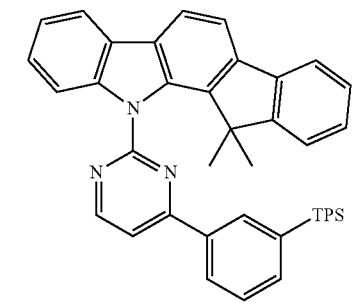
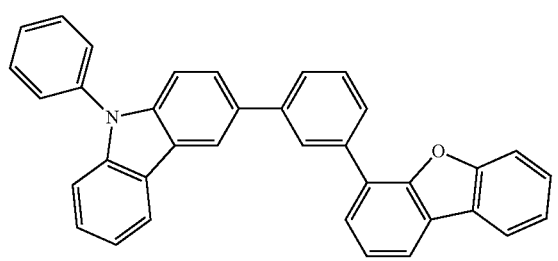
60
-continued
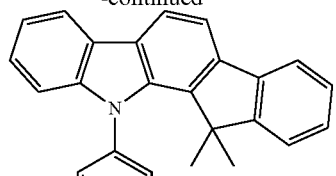
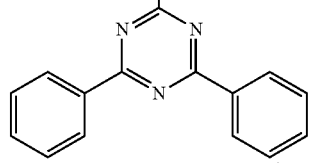
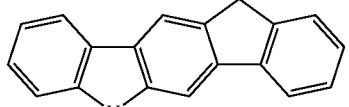
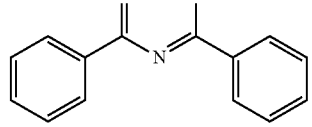
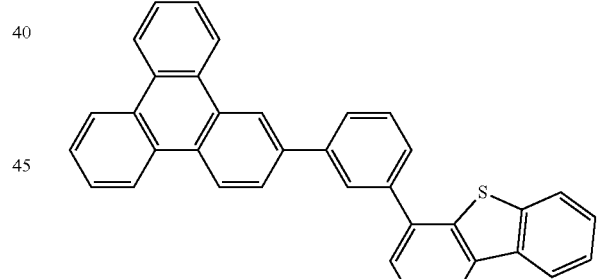
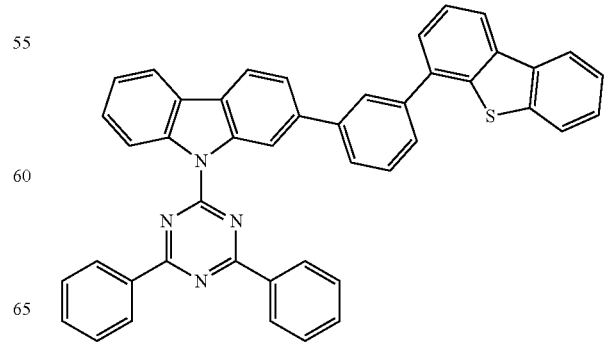

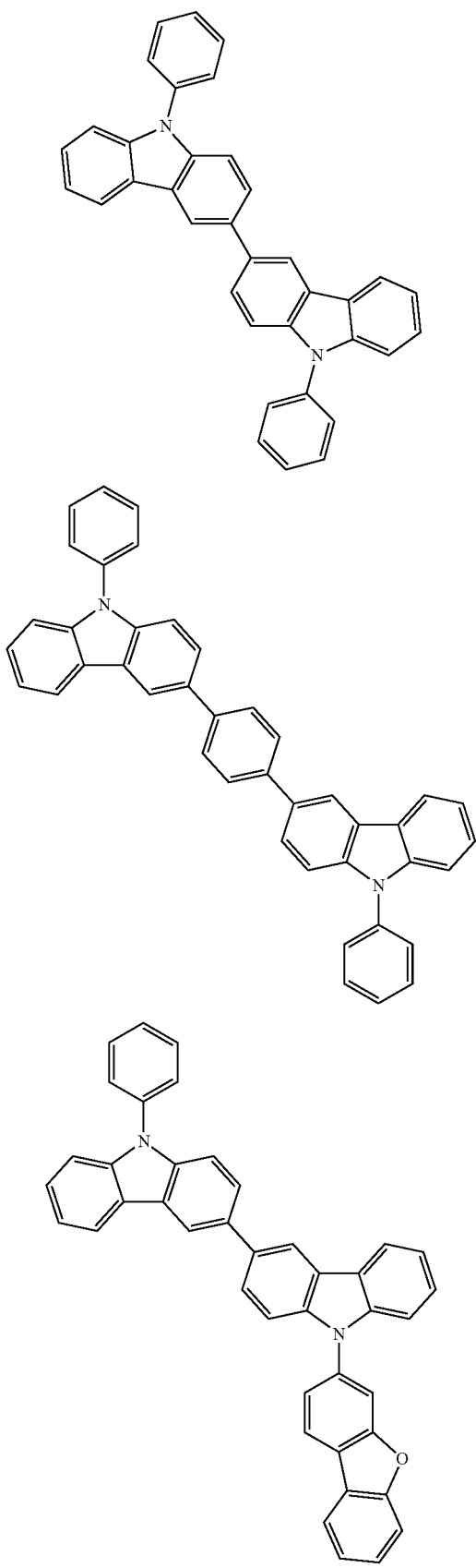

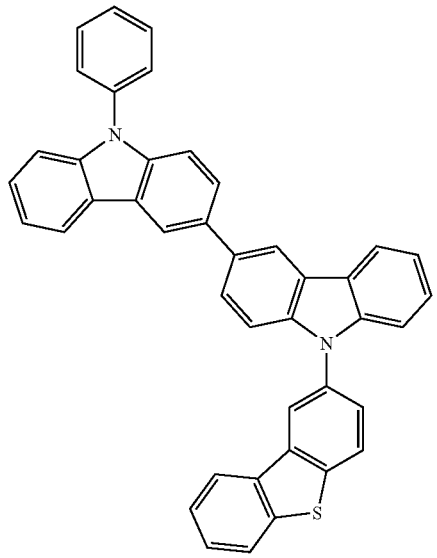

[wherein TPS represents a triphenylsilyl group]

The dopant comprised in the organic electroluminescent device according to the present disclosure is preferably at least one phosphorescent dopant. The dopant materials applied to the organic electroluminescent device according to the present disclosure are not limited, but may be preferably selected from metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The phosphorescent dopant is preferably selected from compounds represented by the following formulas 101 to 103.

(101)

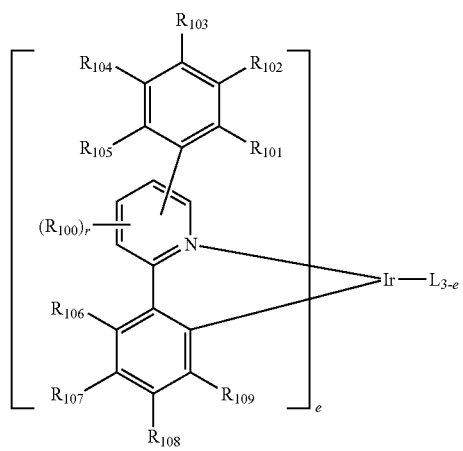

(102)

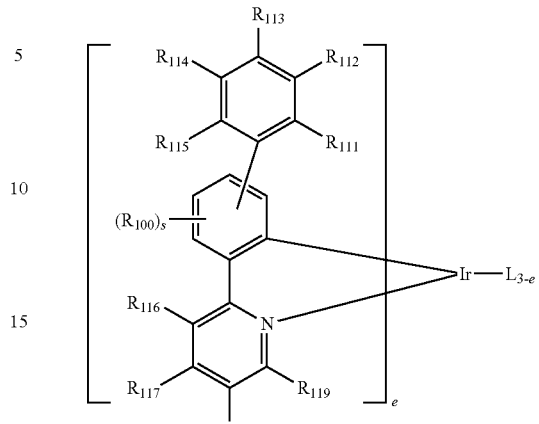

(103)

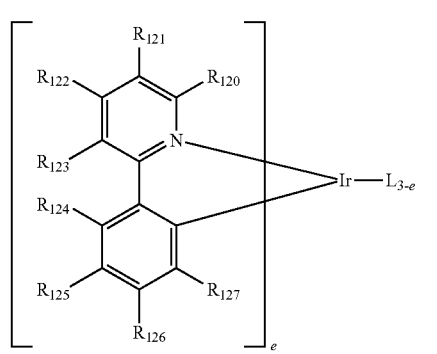

wherein L is selected from the following structures:

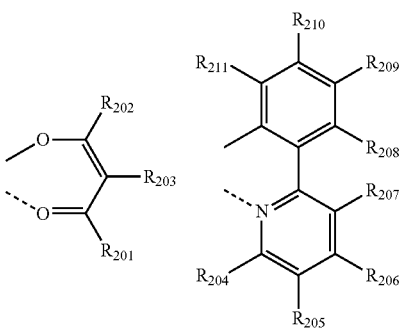

$R_{100}$ represents hydrogen, a substituted or unsubstituted (C1-C30)alkyl, or a substituted or unsubstituted (C3-C30)cycloalkyl;

$R_{101}$ to $R_{109}$, and $R_{111}$ to $R_{123}$, each independently, represent hydrogen, deuterium, a halogen, a (C1-C30)alkyl unsubstituted or substituted with a halogen(s), a cyano, a substituted or unsubstituted (C1-C30)alkoxy, a substituted or unsubstituted (C6-C30)aryl, or a substituted or unsubstituted (C3-C30)cycloalkyl; adjacent substituents of $R_{106}$ to $R_{109}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl; and adjacent substituents of $R_{120}$ to $R_{123}$ may be linked to each other to form a substituted or unsubstituted fused ring, e.g., quinoline unsubstituted or substituted with alkyl or aryl;

$R_{124}$ to $R_{127}$, each independently, represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

$R_{201}$ to $R_{211}$, each independently, represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30)aryl; and adjacent substituents of $R_{208}$ to $R_{211}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

r and s, each independently, represent an integer of 1 to 3; where r or s is an integer of 2 or more, each of $R_{100}$ may be the same or different; and e represents an integer of 1 to 3.

Specifically, the phosphorescent dopant materials include the following:

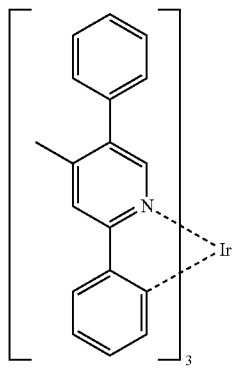

D-1

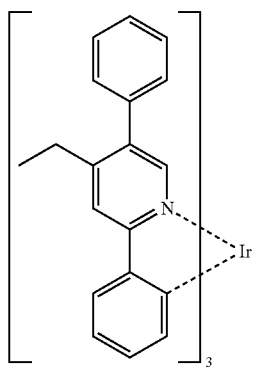

D-2

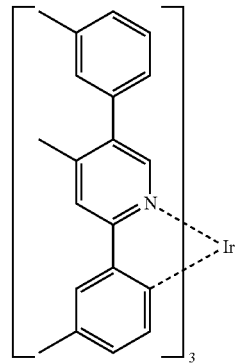

D-3

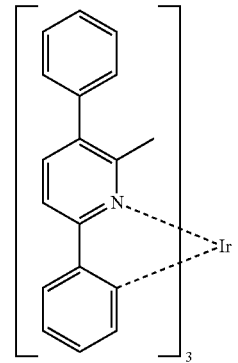

D-4

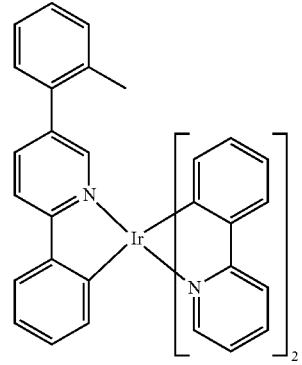

D-5

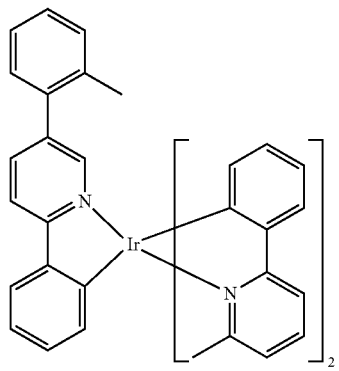

D-6

-continued
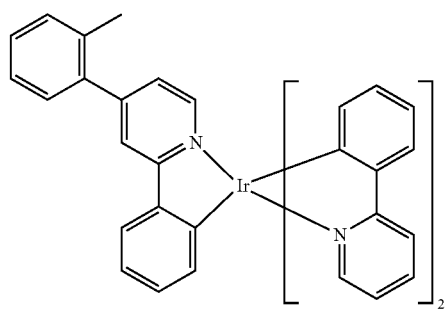
D-7
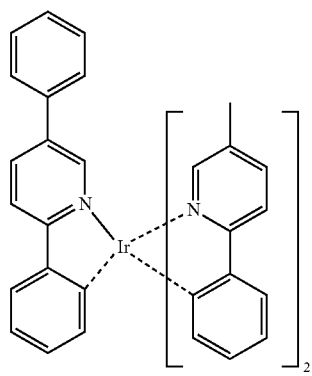
D-8
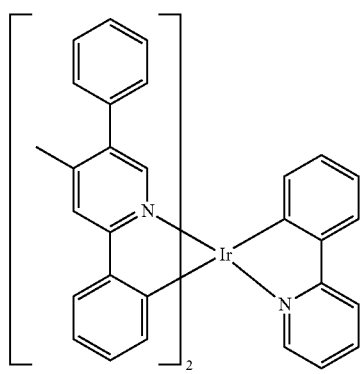
D-9
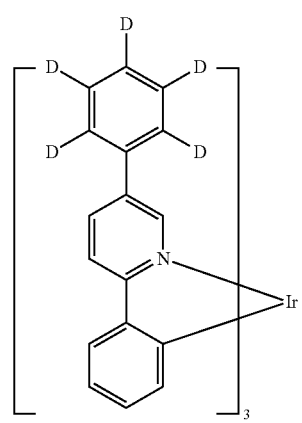
D-10
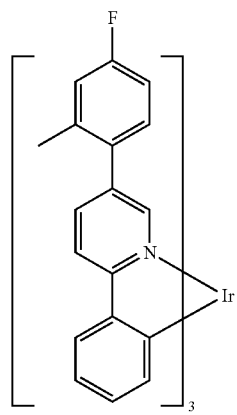
D-11
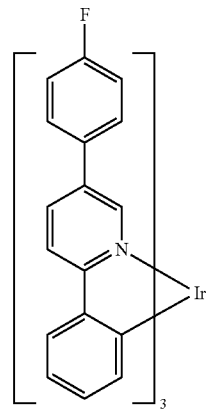
D-12
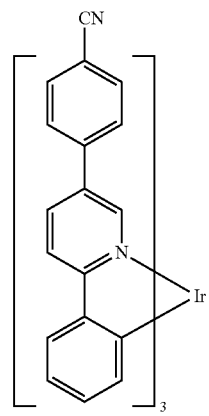
D-13
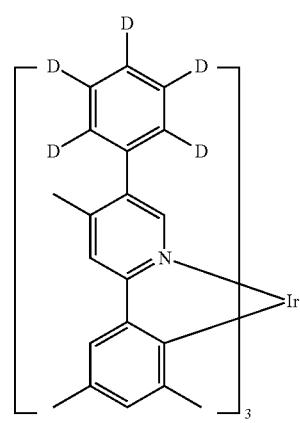
D-14

D-15
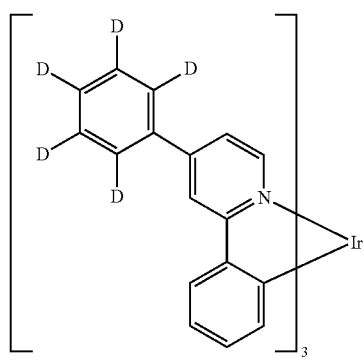
D-16
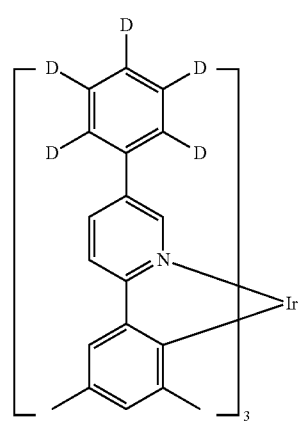
D-17
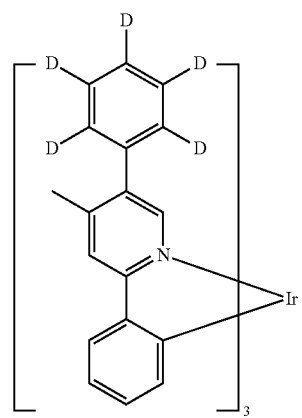
D-18
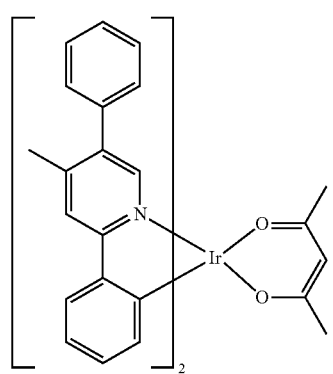
D-19
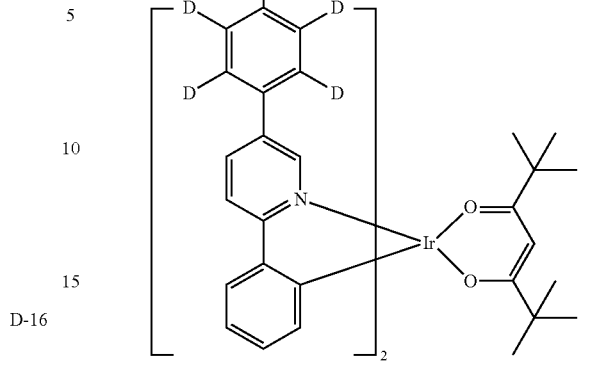
D-20
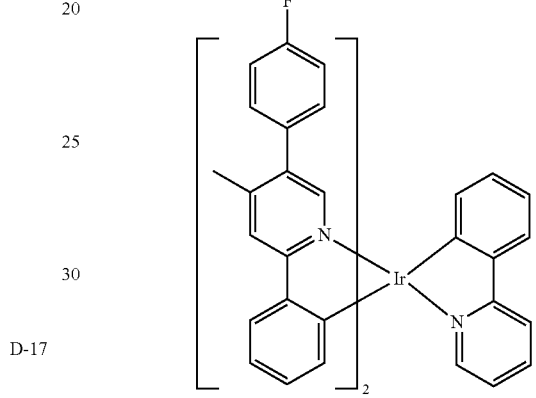
D-21
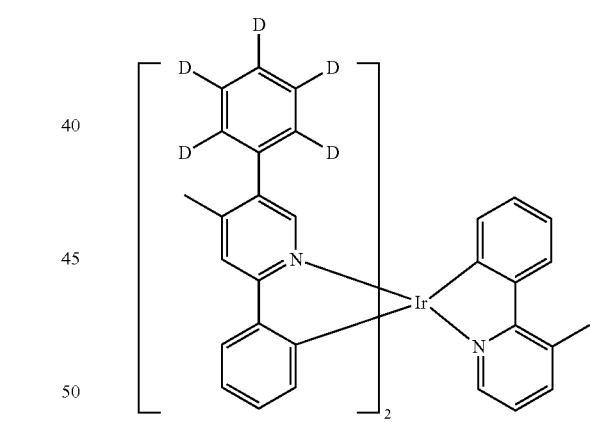
D-22
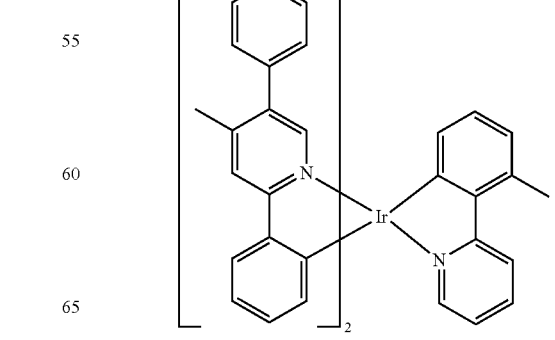

-continued
D-23
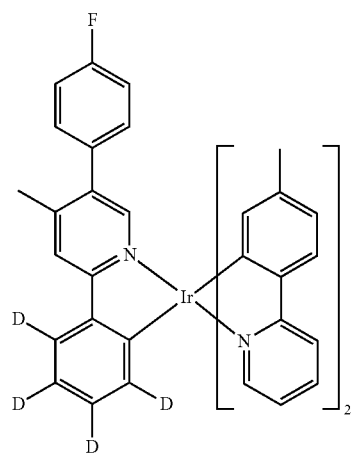
D-24
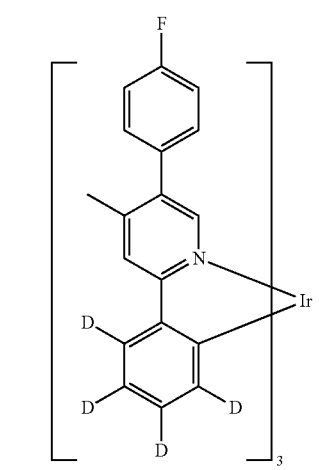
D-25
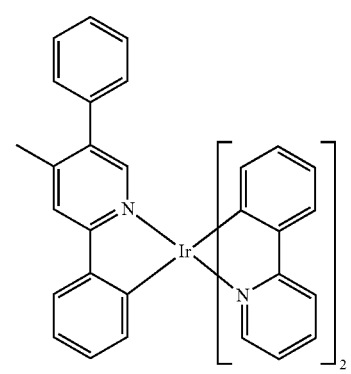
D-26
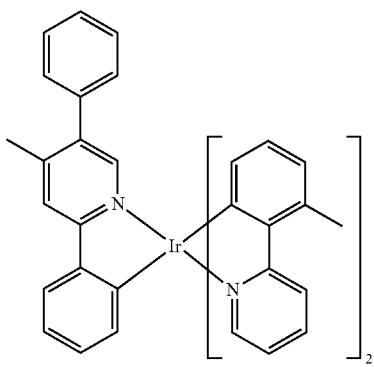
D-27
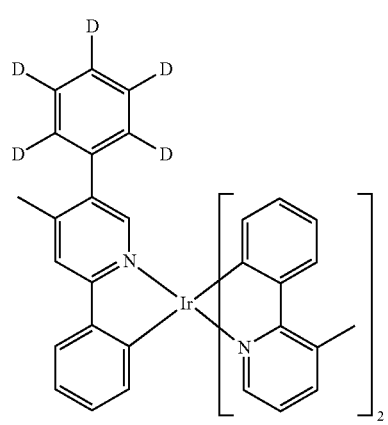
D-28
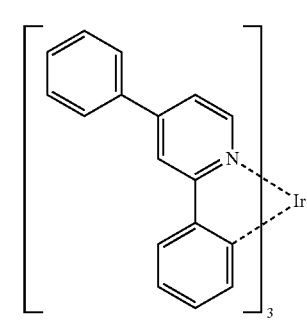
D-29
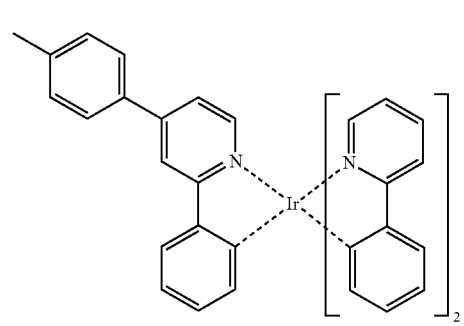
D-30
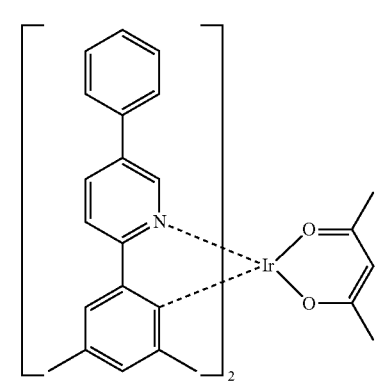

D-31 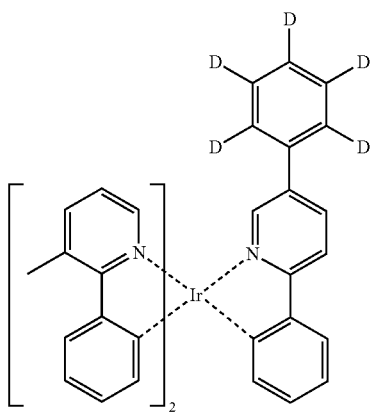
D-32 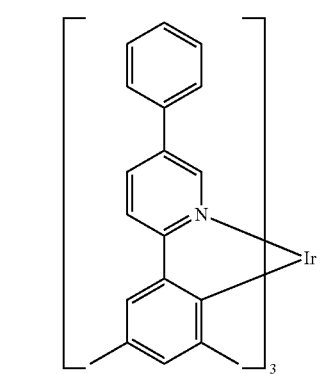
D-33 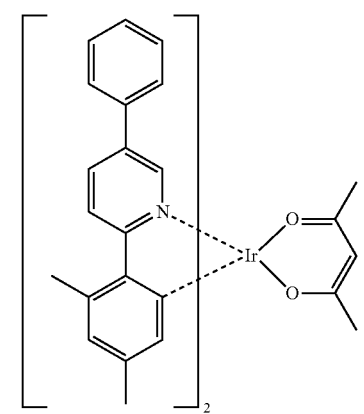
D-34 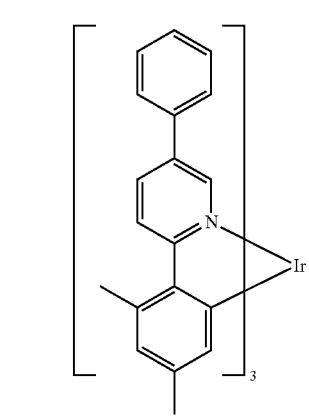
D-35 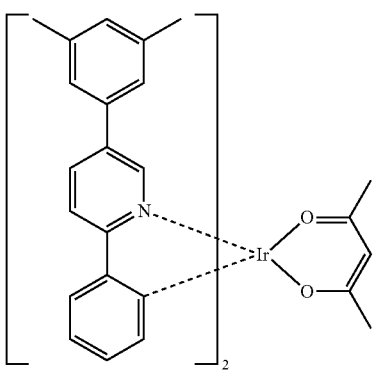
D-36 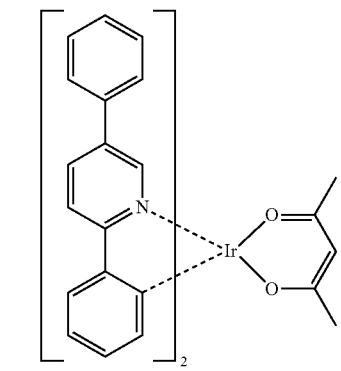
D-37 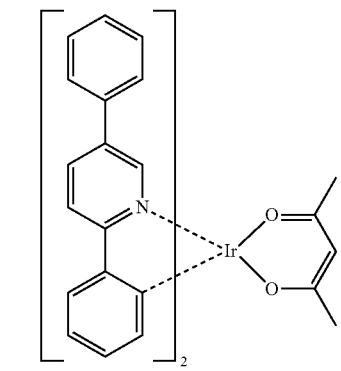
D-38 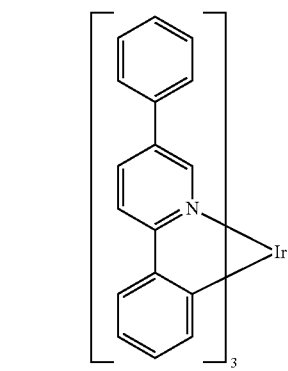

-continued
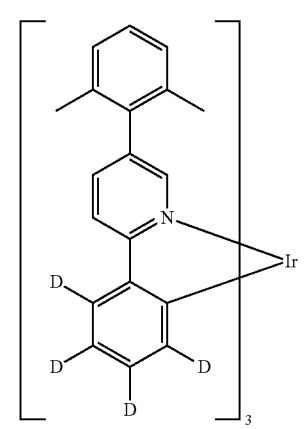
D-39
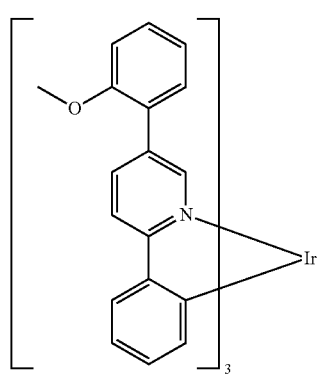
D-40
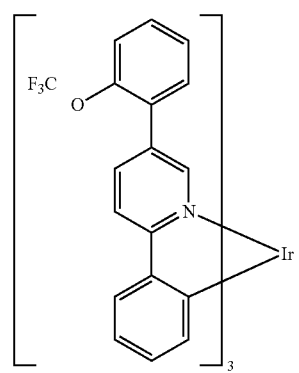
D-41
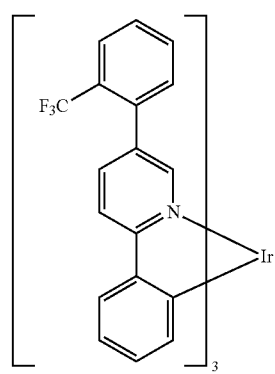
D-42
-continued
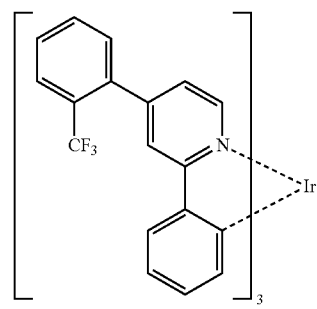
D-43
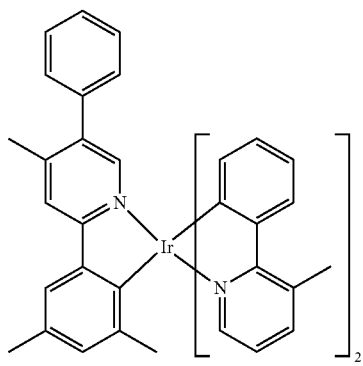
D-44
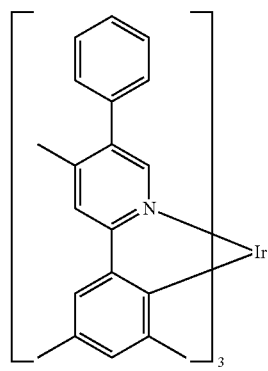
D-45
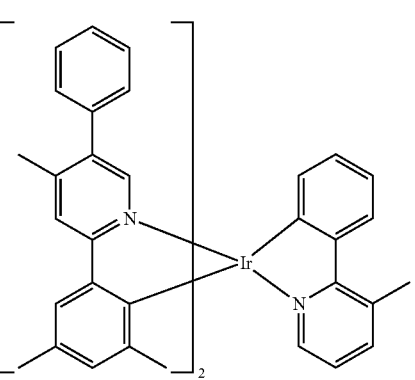
D-46

D-47
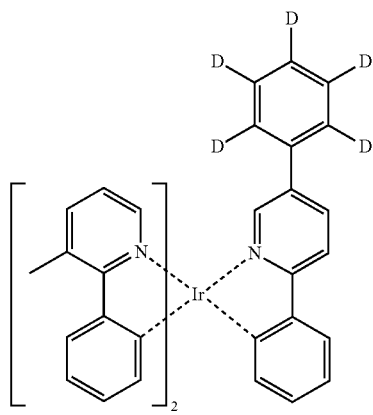
D-48
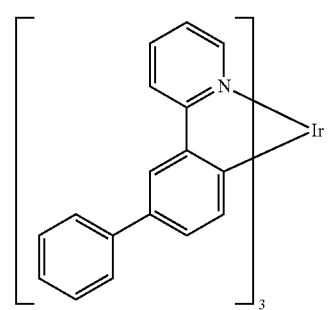
D-49
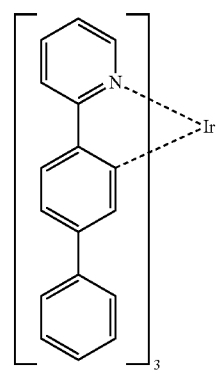
D-50
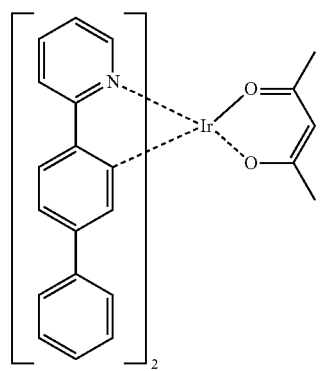
D-51
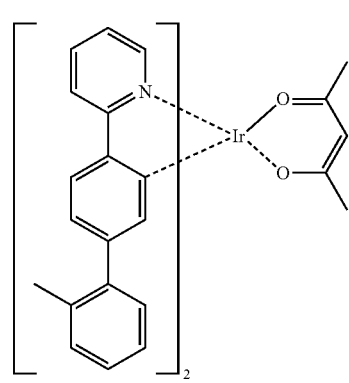
D-52
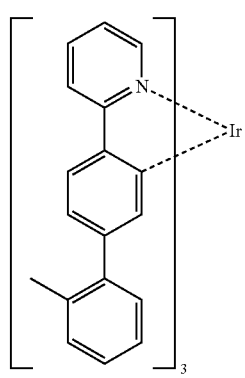
D-53
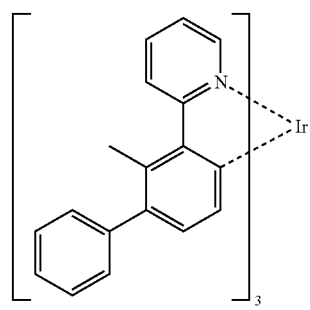
D-54
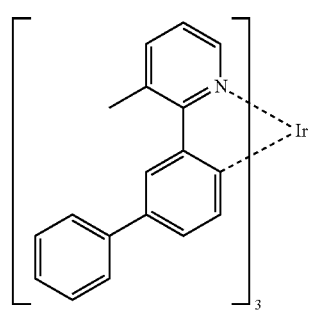

D-55 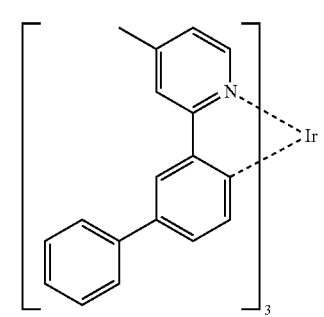
D-56 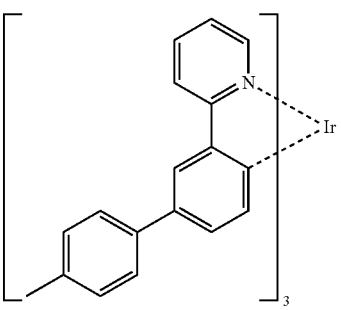
D-57 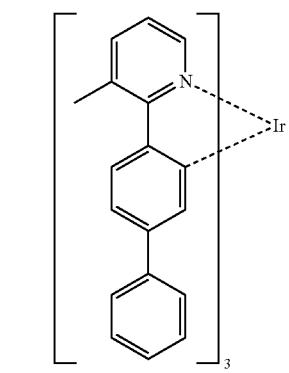
D-58 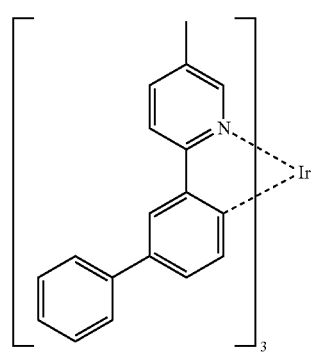
D-59 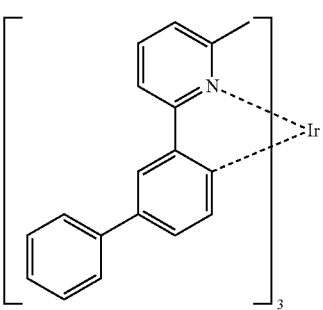
D-60 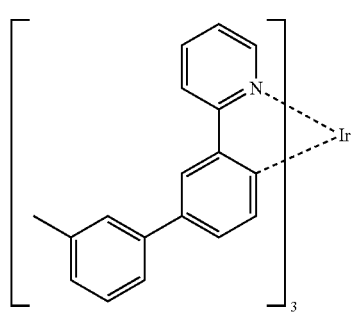
D-61 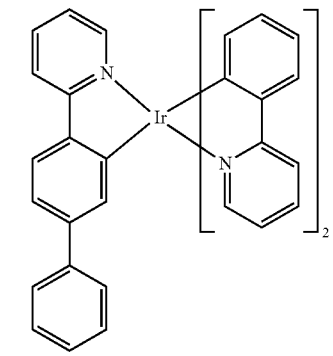
D-62 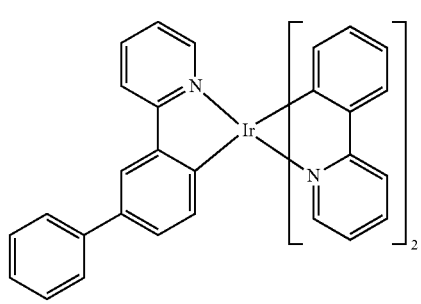
D-63 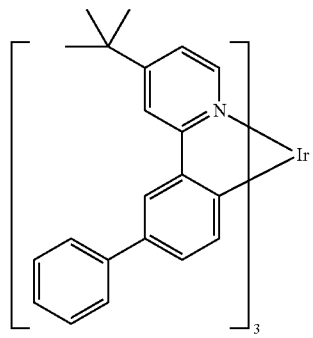
D-64 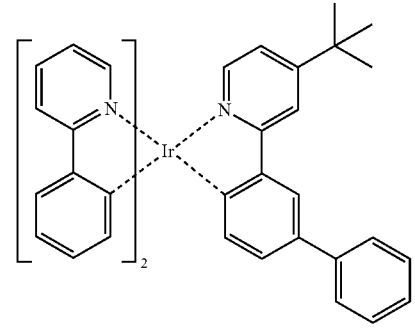

D-65
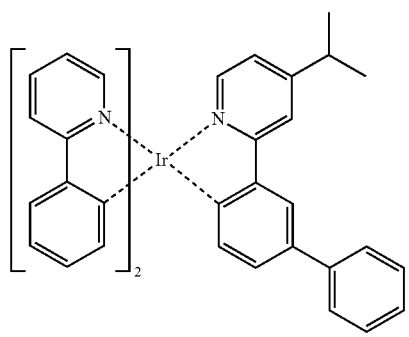
D-66
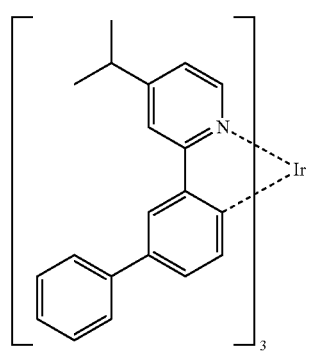
D-67
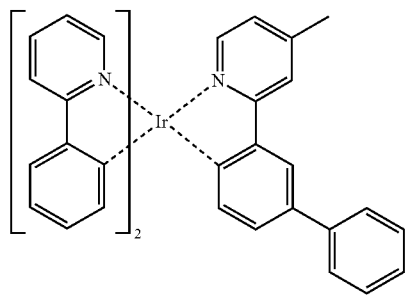
D-68
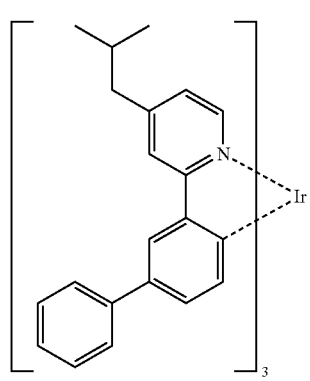
D-69
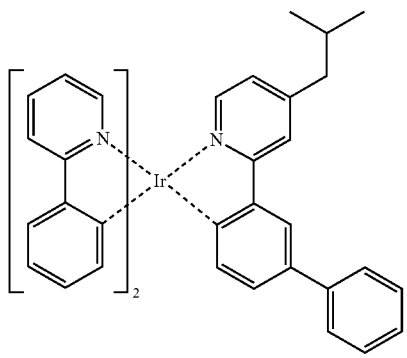
D-70
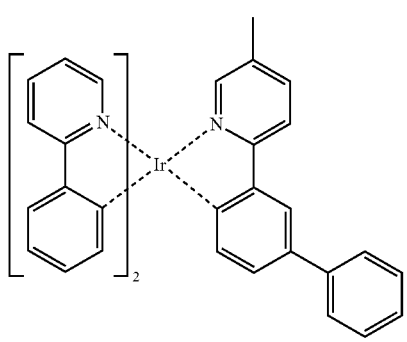
D-71
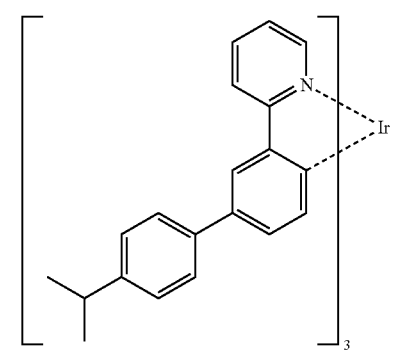
D-72
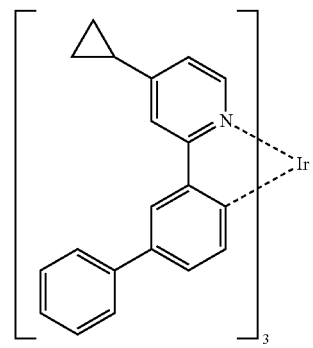

D-73 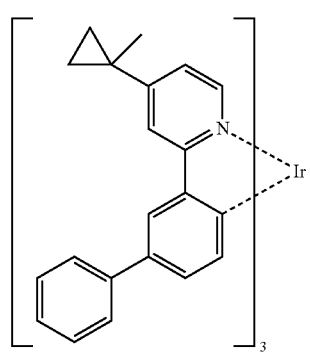
D-77 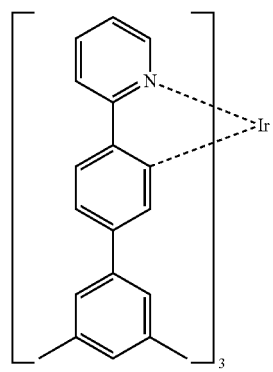
D-74 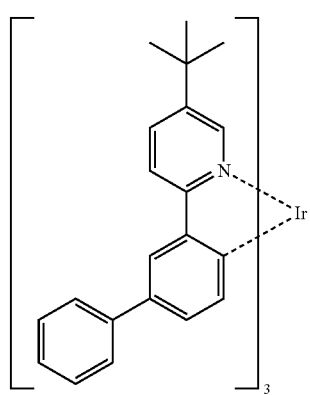
D-78 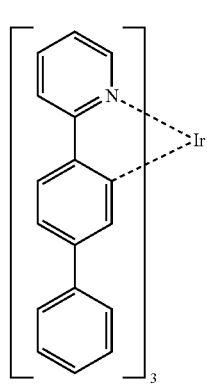
D-75 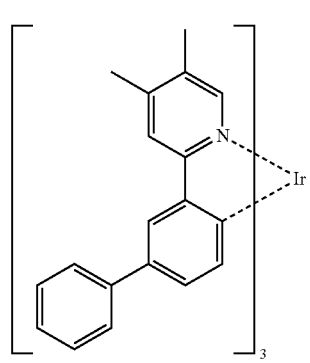
D-79 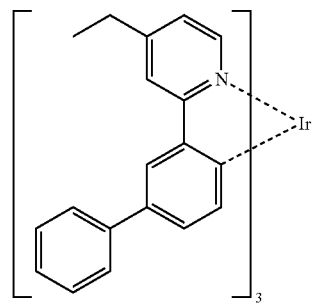
D-76 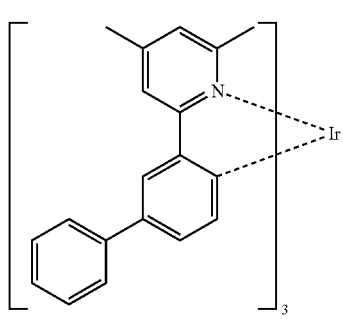
D-80 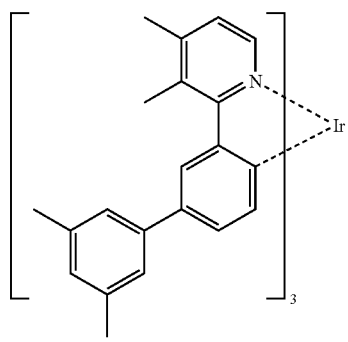

D-81
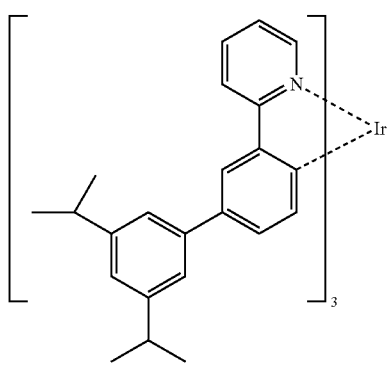
D-82
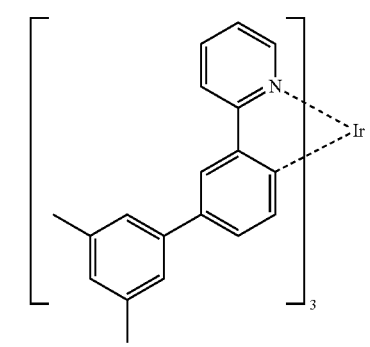
D-83
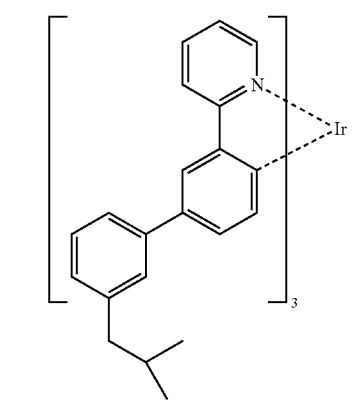
D-84
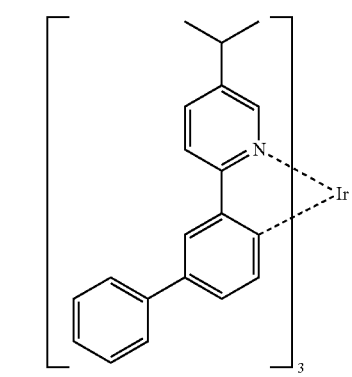
D-85
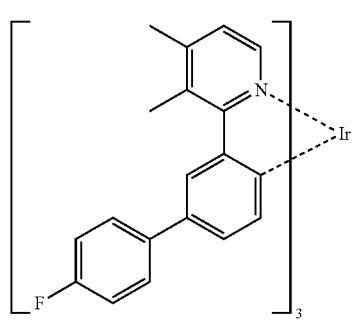
D-86
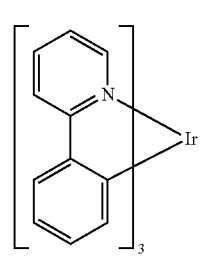
D-87
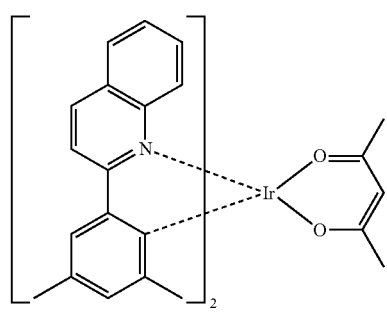
D-88
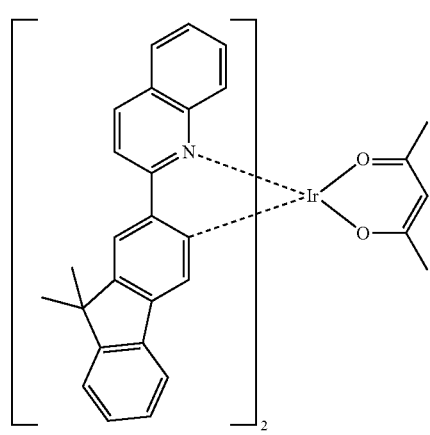
D-89
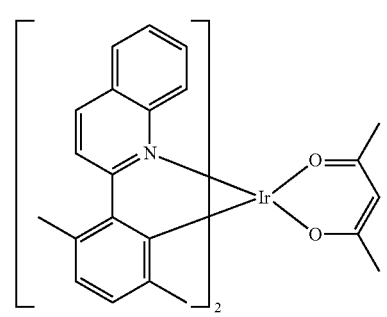

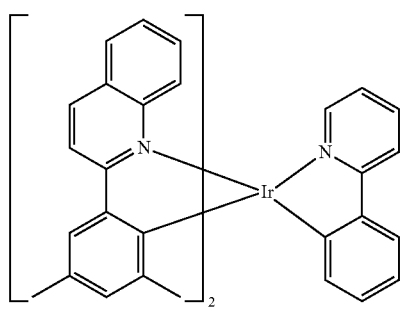
D-90
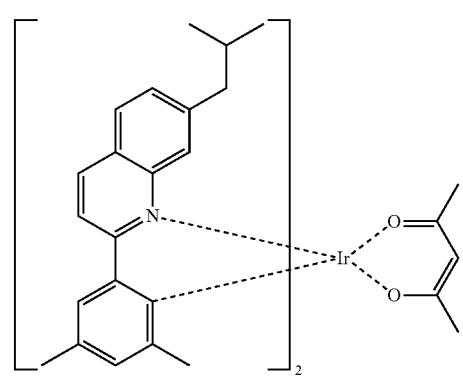
D-94
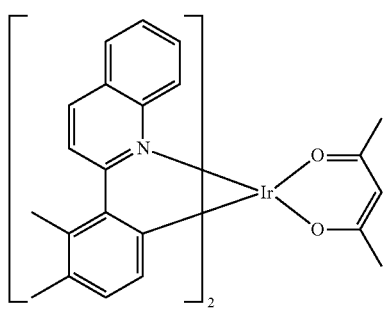
D-91
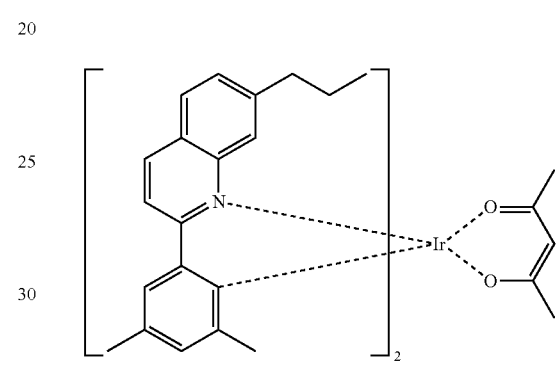
D-95
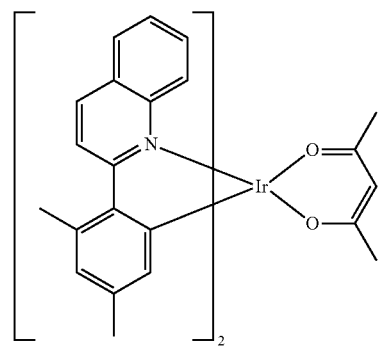
D-92
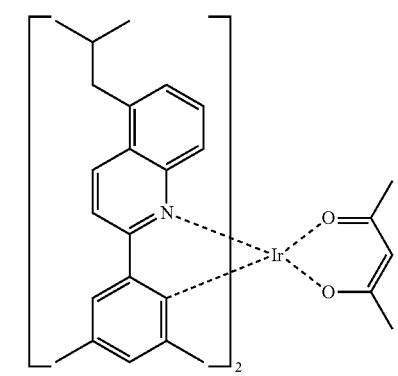
D-96
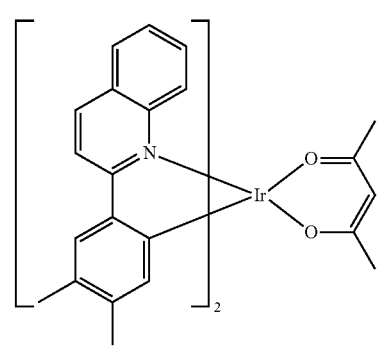
D-93
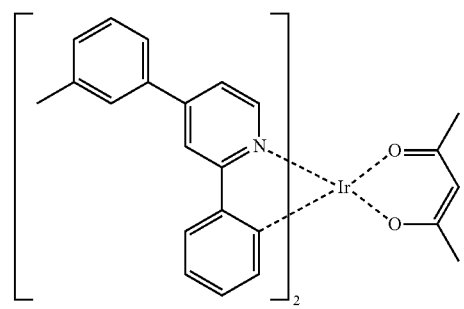
D-97

D-98
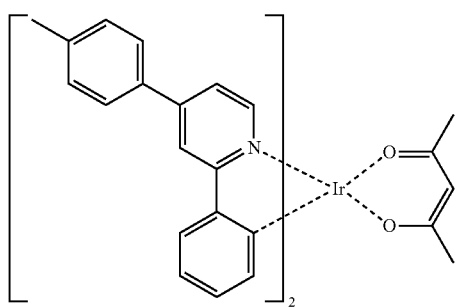
D-99
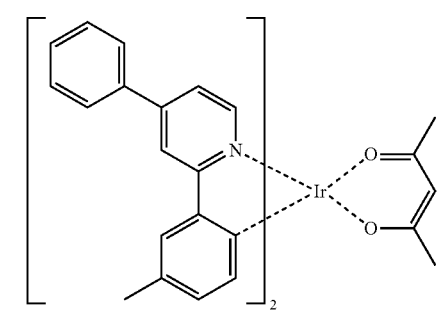
D-100
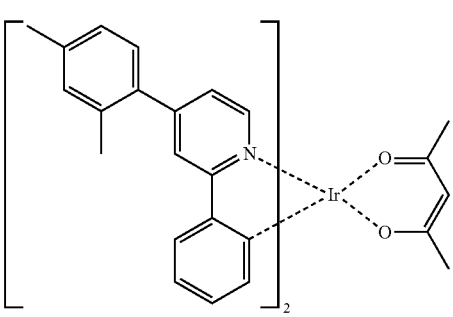
D-101
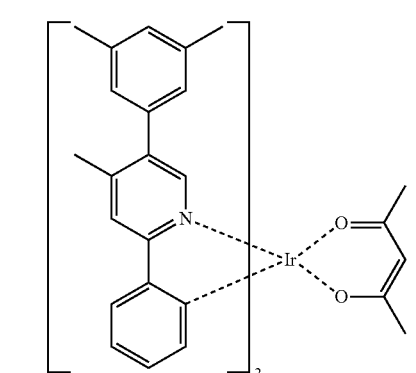
D-102
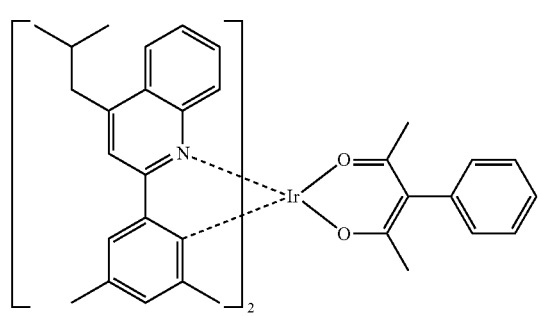
D-103
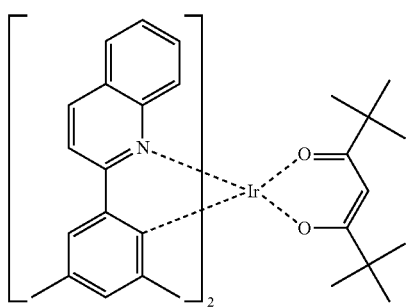
D-104
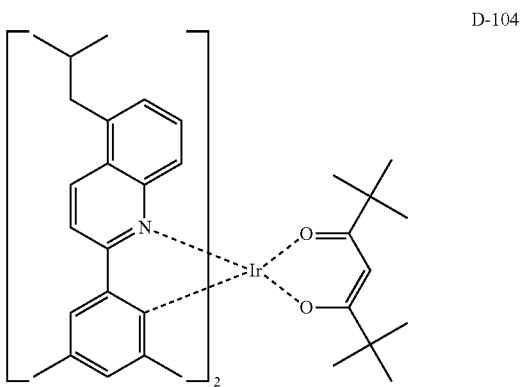
D-105
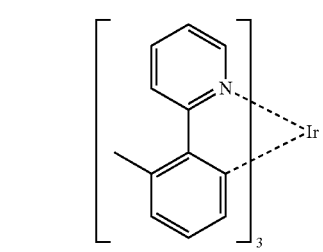
D-106
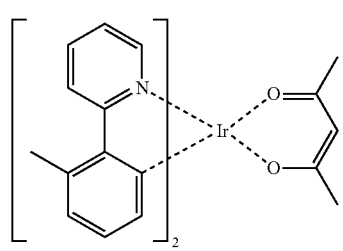
D-107
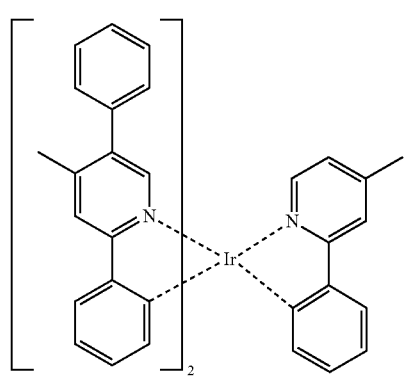

D-108 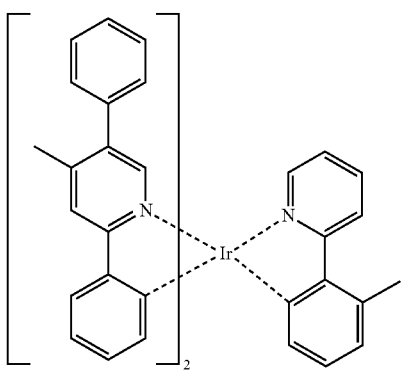
D-109 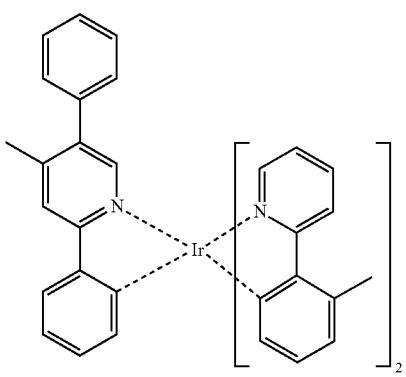
D-110 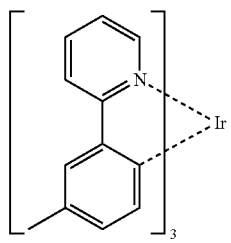
D-111 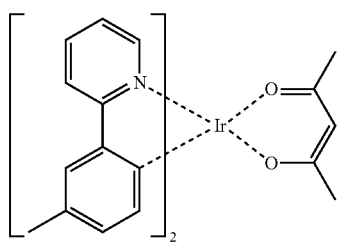
D-112 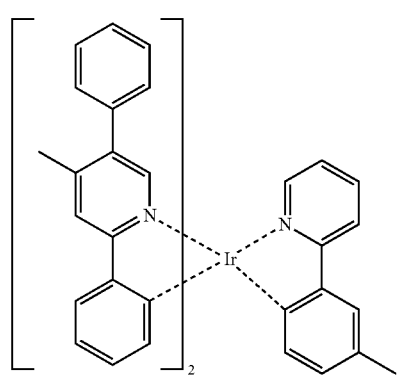
D-113 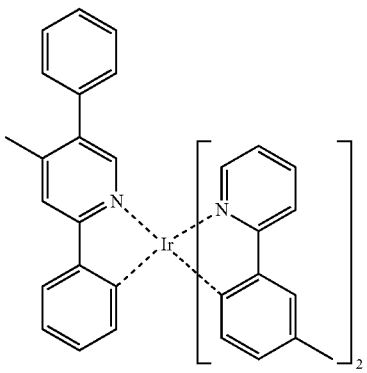
D-114 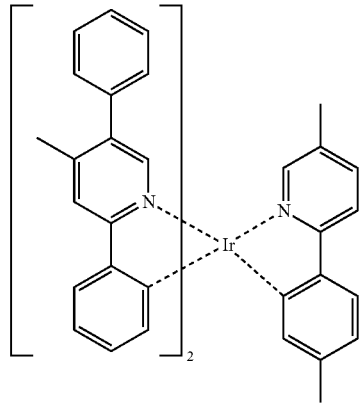
D-115 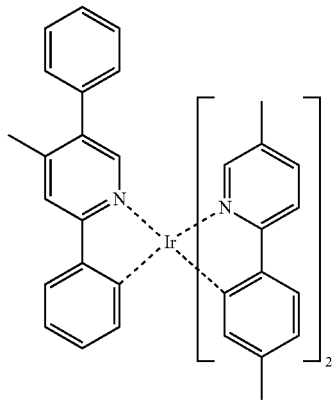
D-116 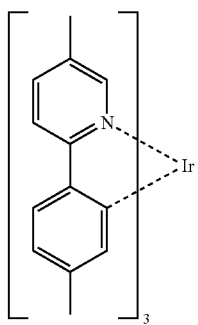

D-117
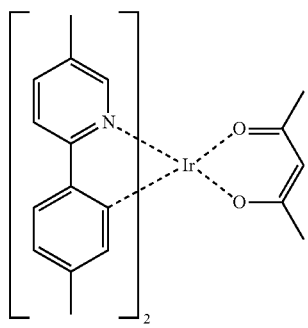
D-118
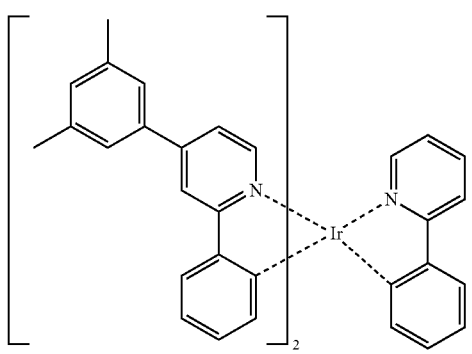
D-119
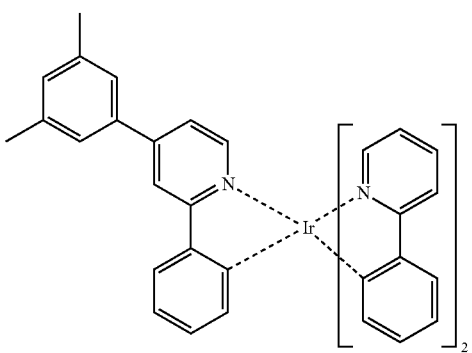
D-120
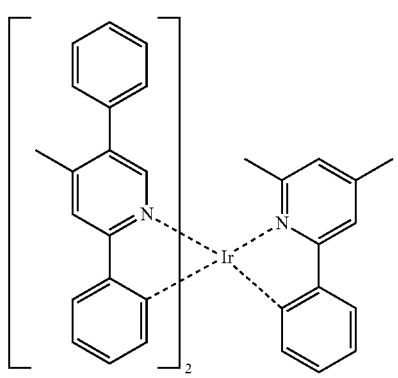
D-121
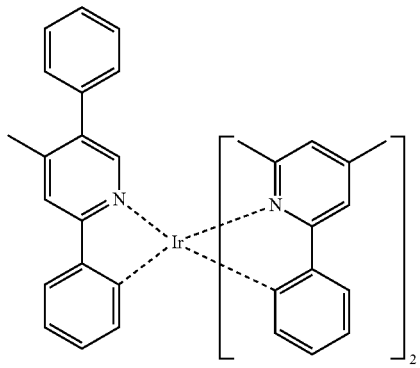
D-122
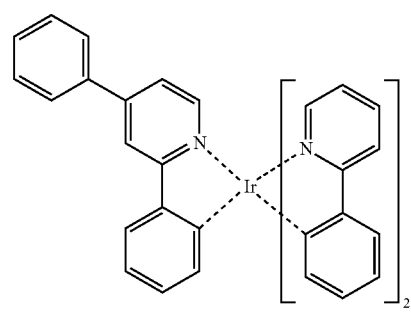
D-123
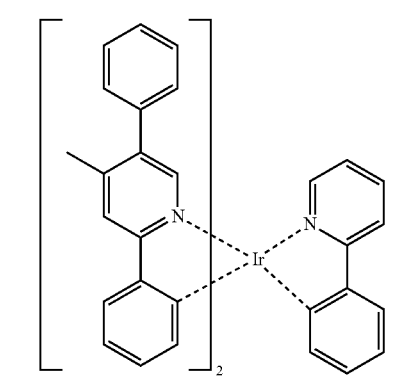
D-124
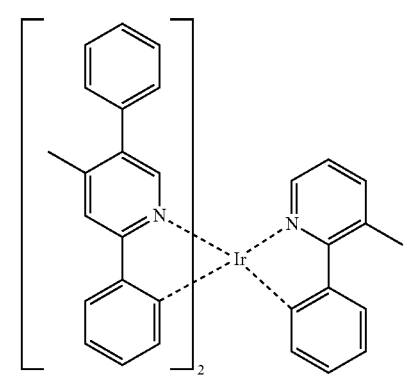

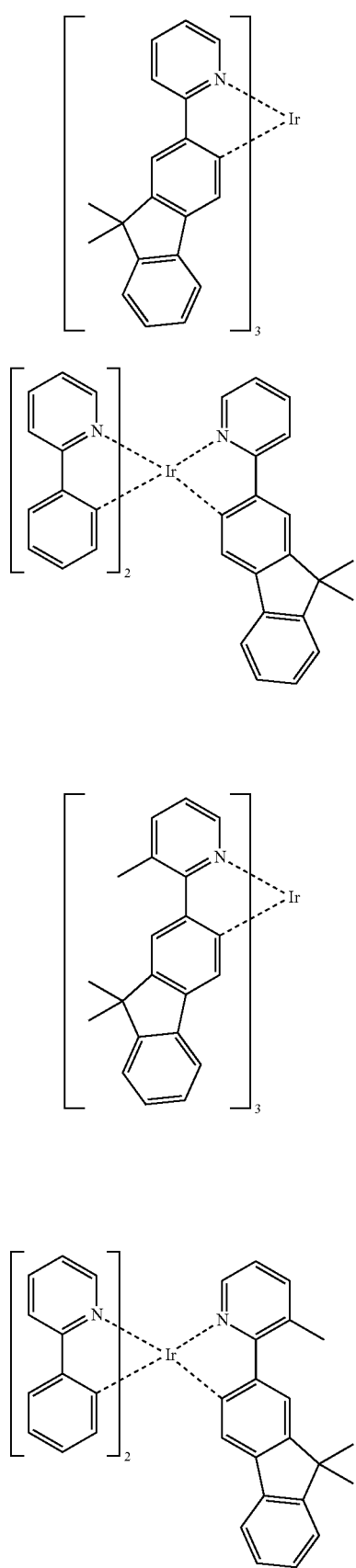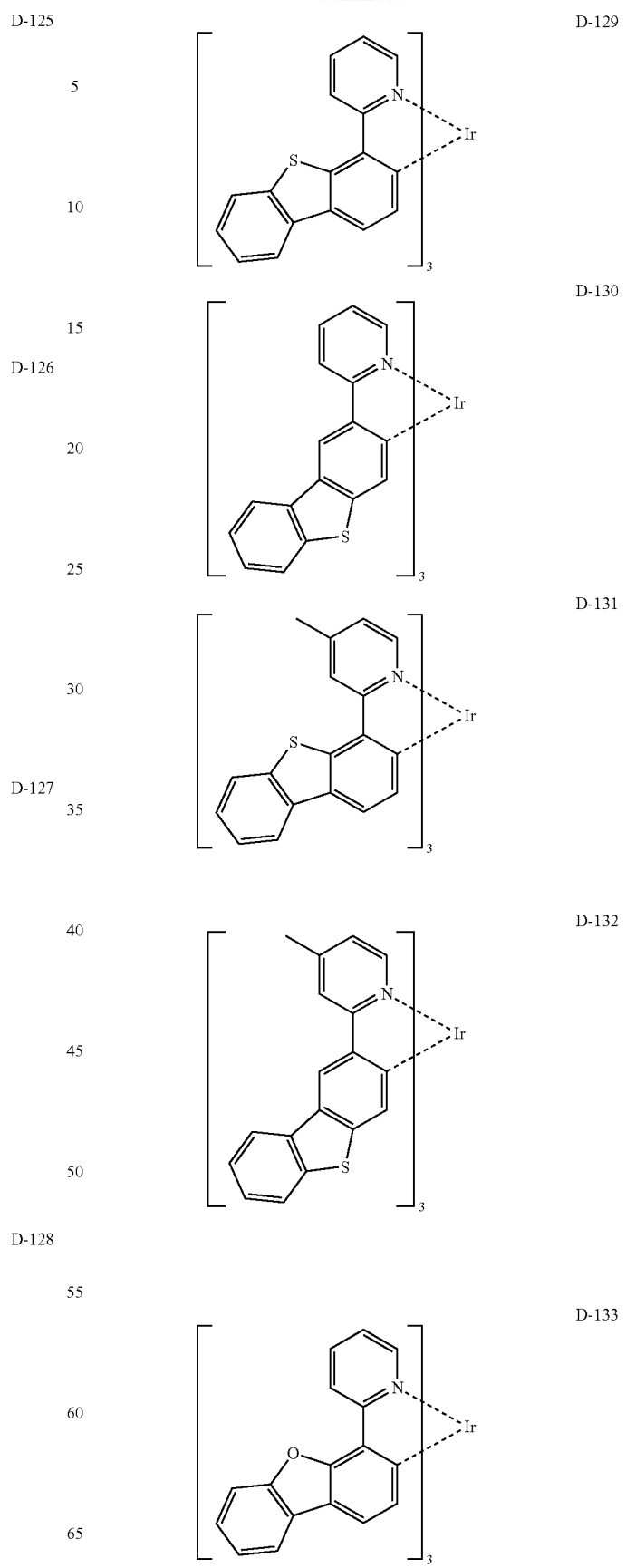

D-134
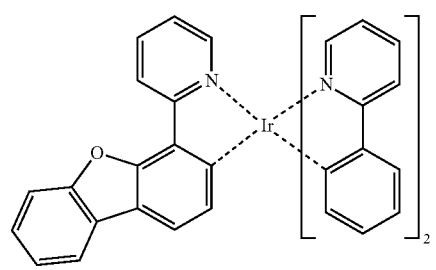
D-135
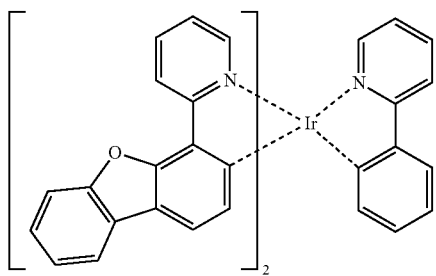
D-136
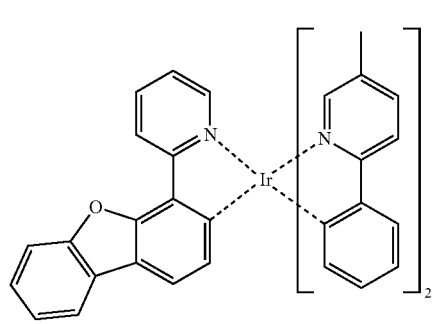
D-137
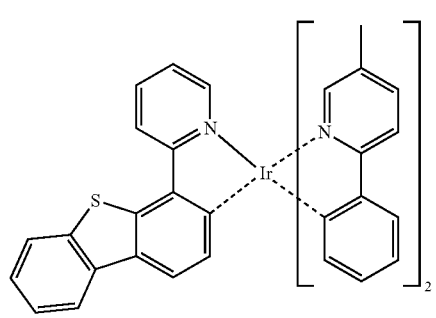
D-138
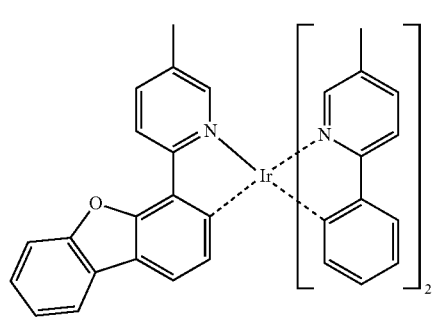
D-139
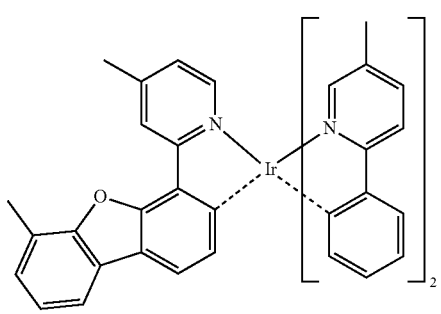
D-140
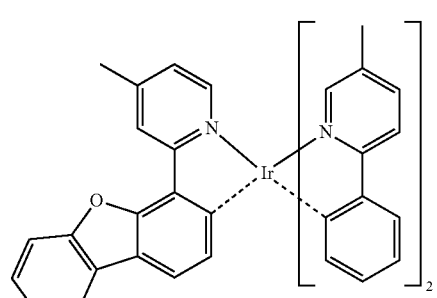
D-141
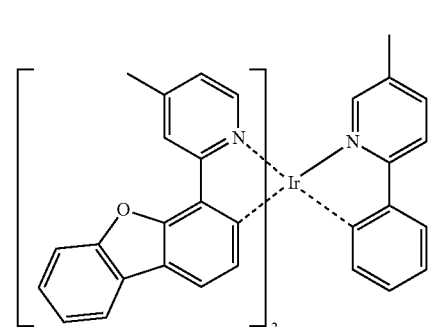
D-142
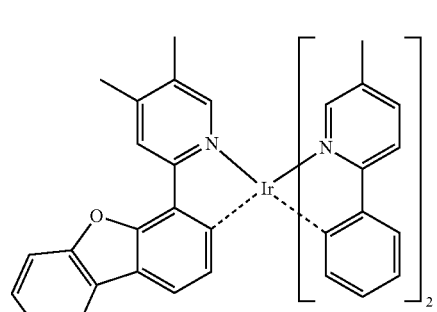
D-143
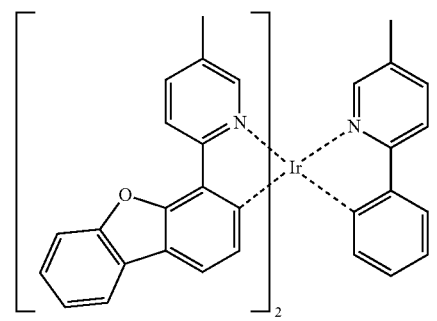

D-144
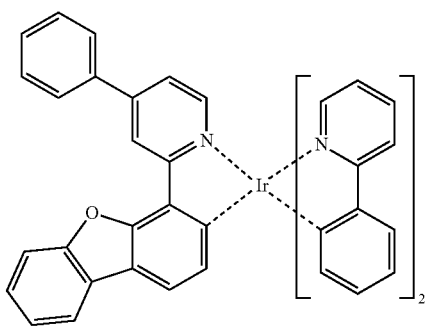
D-145
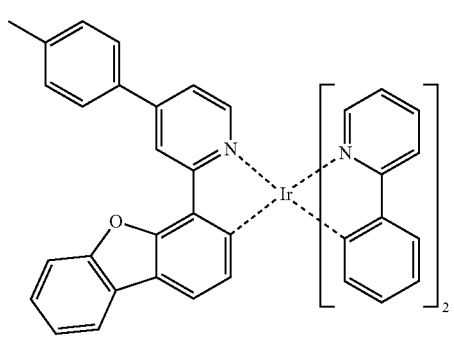
D-146
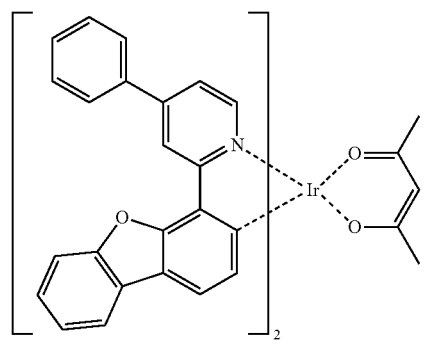
D-147
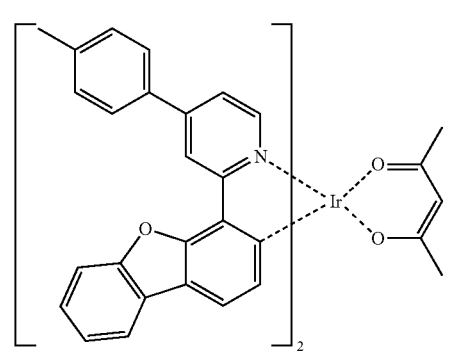
D-148
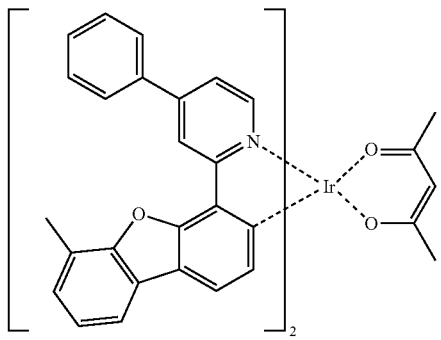
D-149
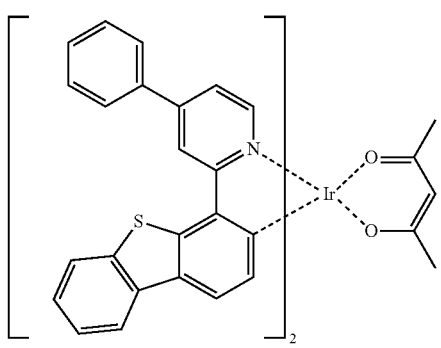
D-150
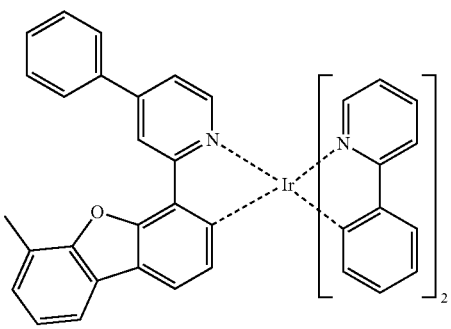
D-151
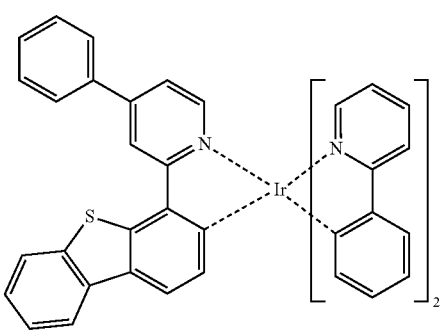
D-152
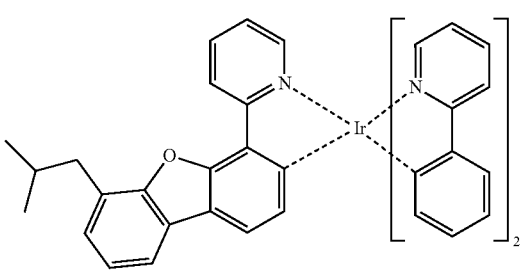

D-153
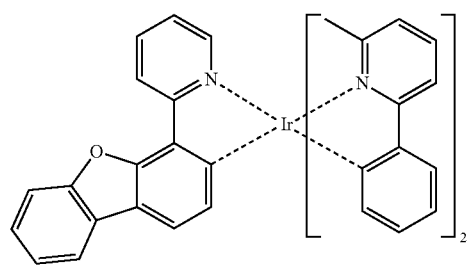
D-154
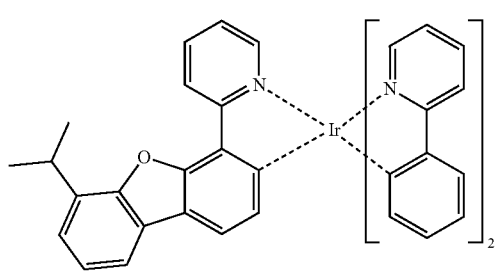
D-155
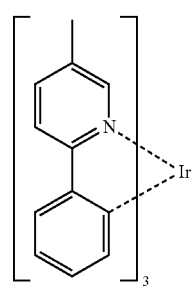
D-156
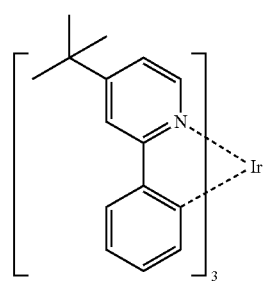
D-157
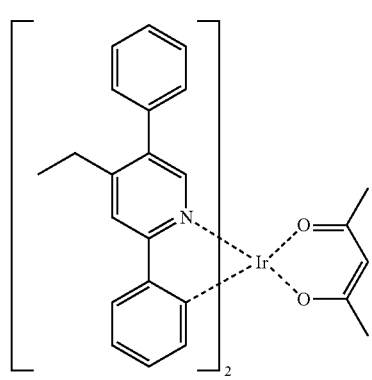
D-158
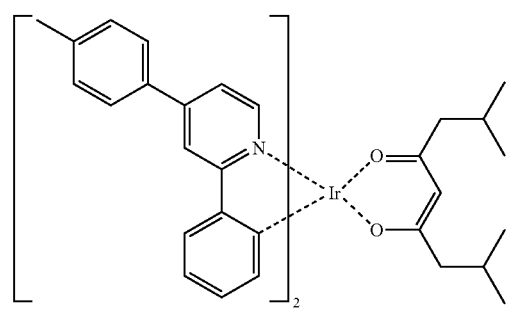
D-159
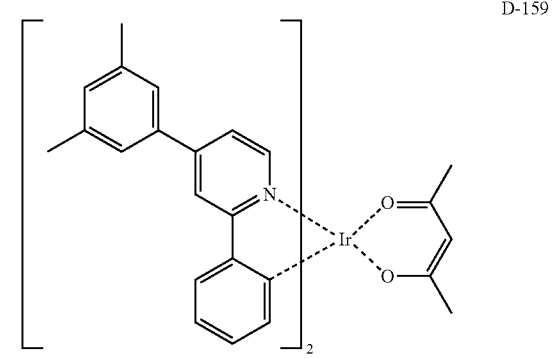
D-160
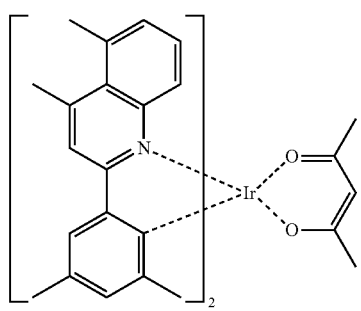
D-161
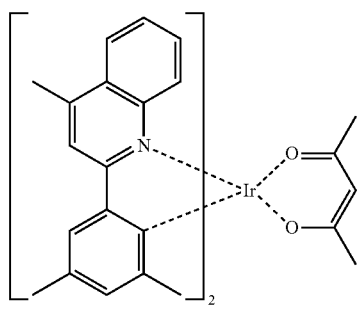
D-162
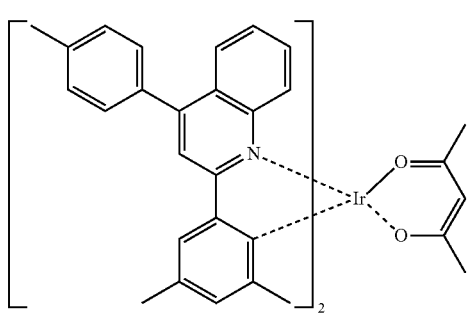

D-163 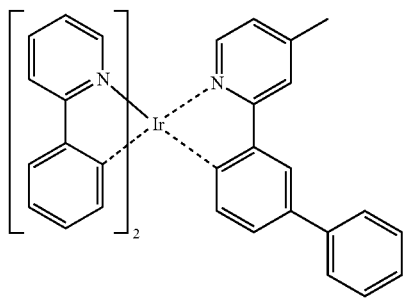
D-164 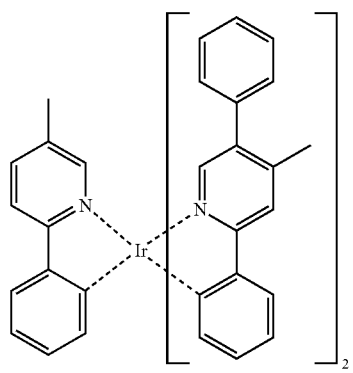
D-165 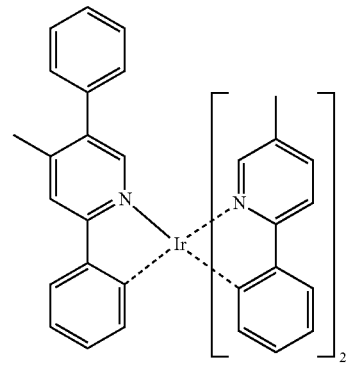
D-166 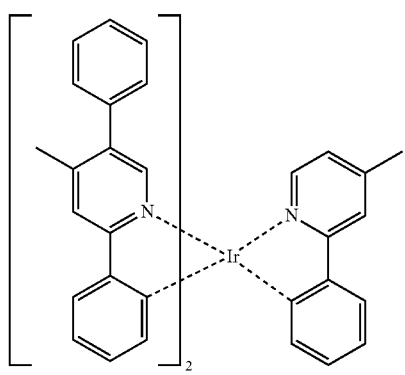
D-167 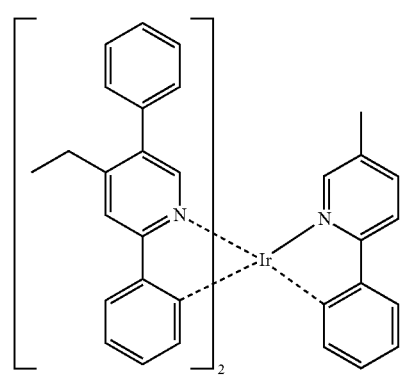
D-168 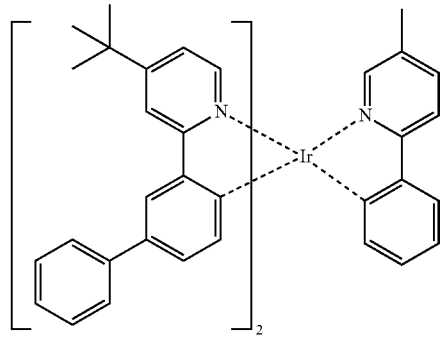
D-169 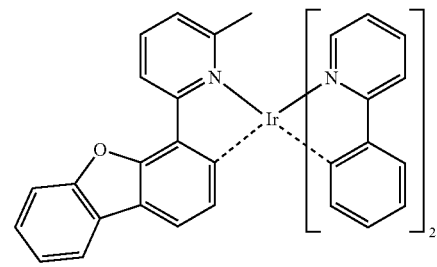
D-170
D-171 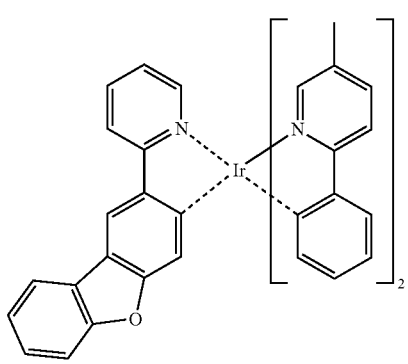

-continued
D-172
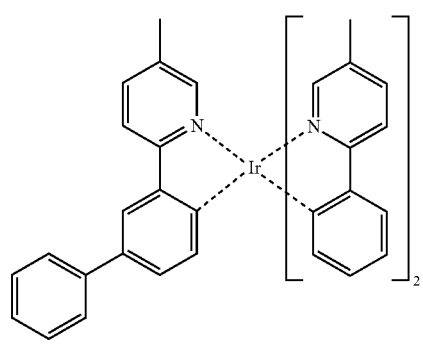
D-173
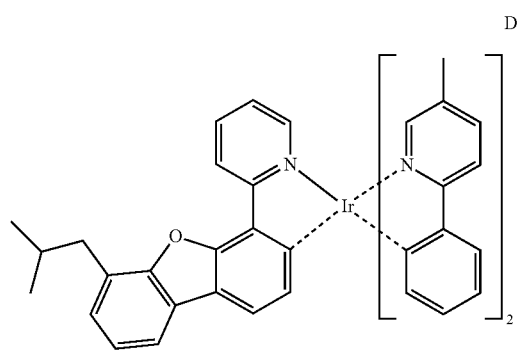
D-174
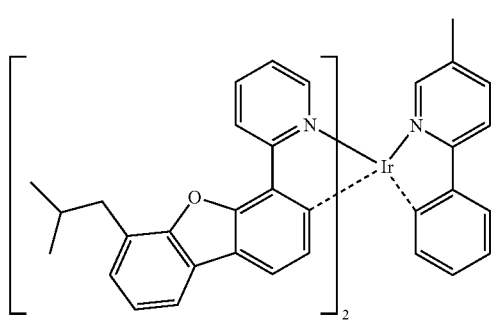
D-175
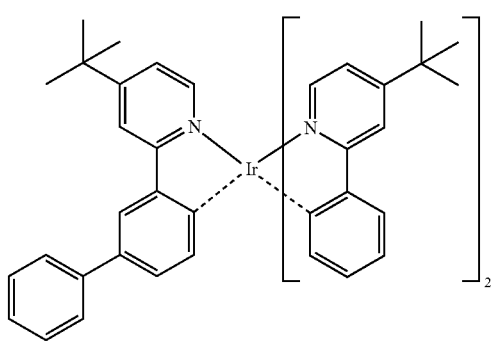
-continued
D-176
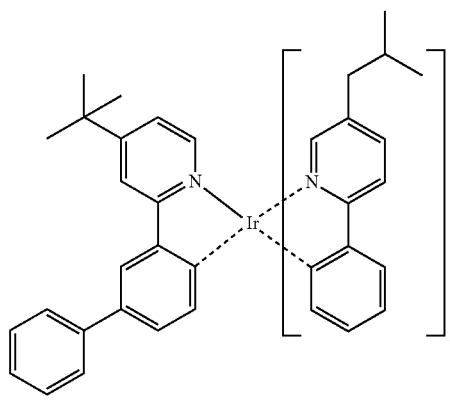
D-177
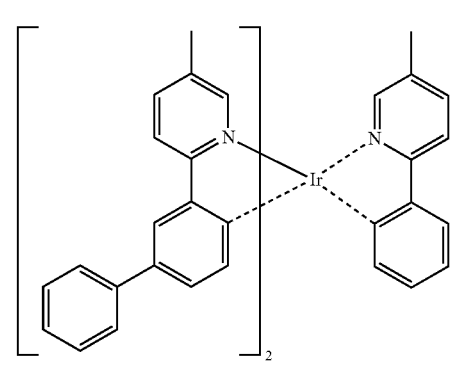
D-178
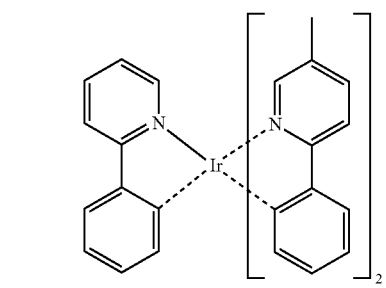
D-179
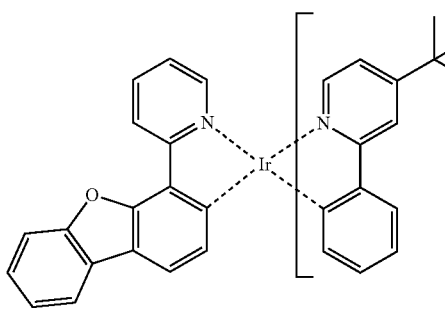

-continued
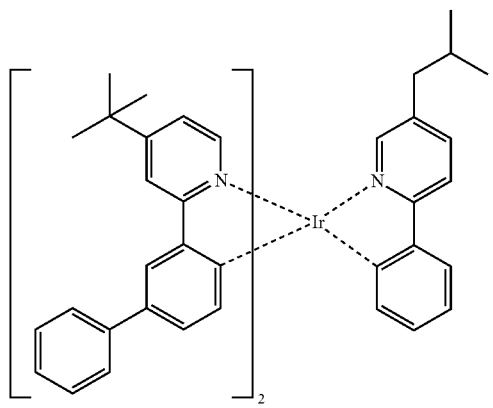
D-180
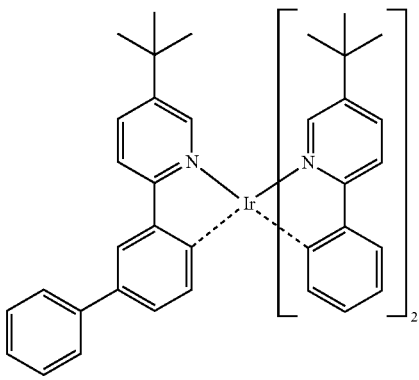
D-184
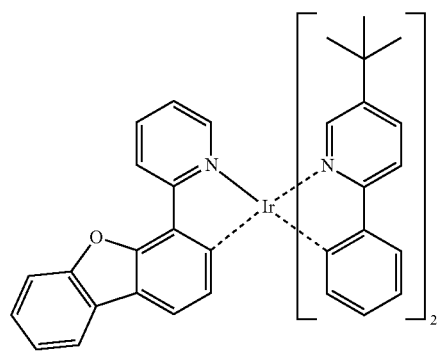
D-181
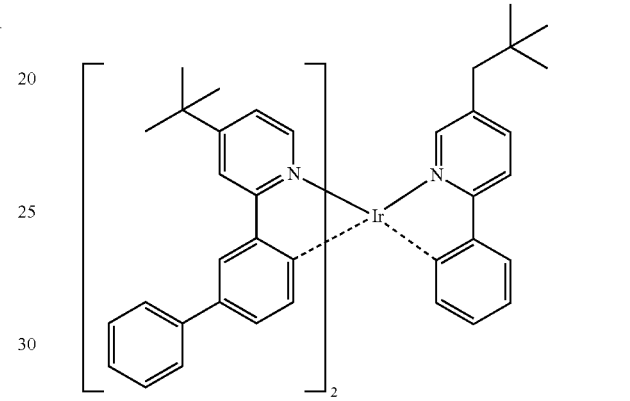
D-185
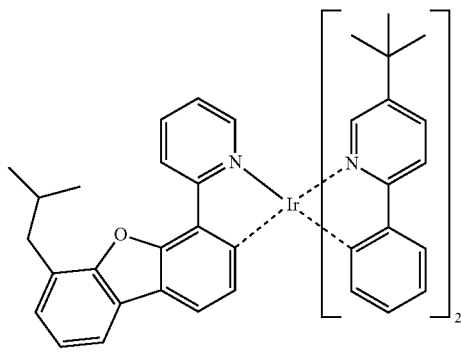
D-182
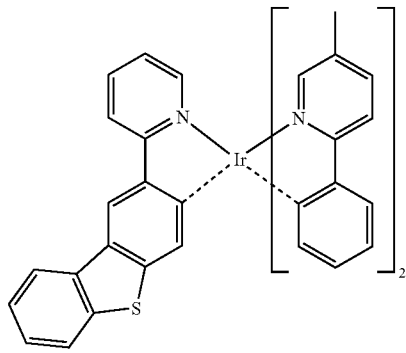
D-186
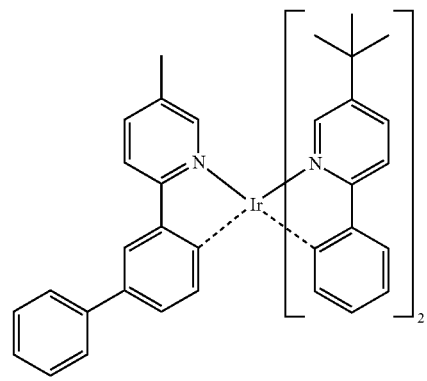
D-183
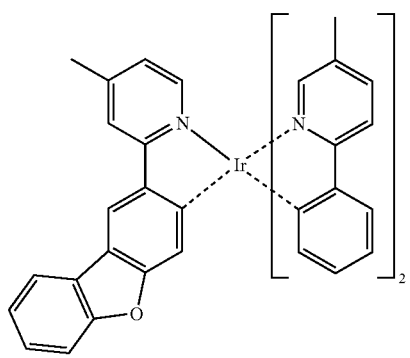
D-187

D-188 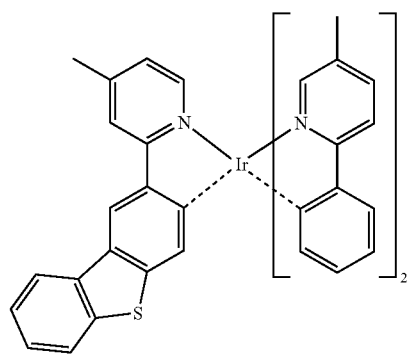
D-189 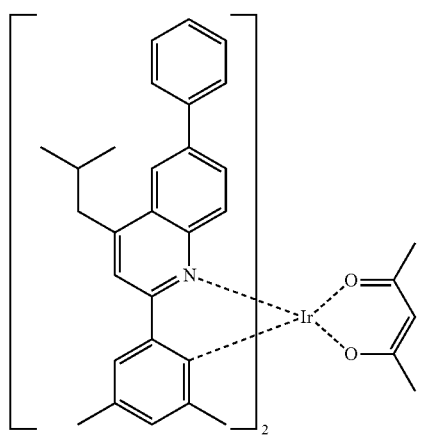
D-190 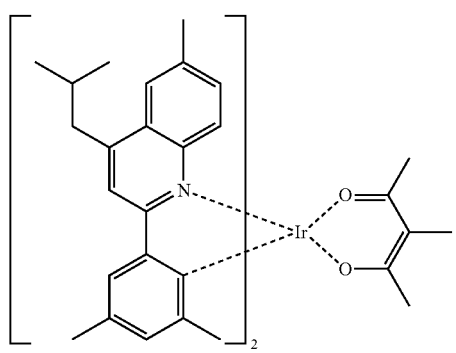
D-191 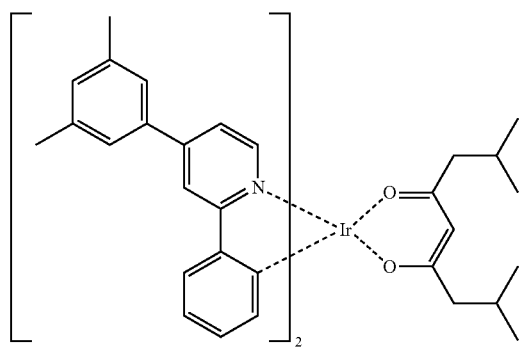
D-192 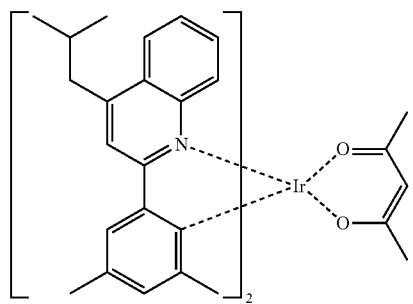
D-193 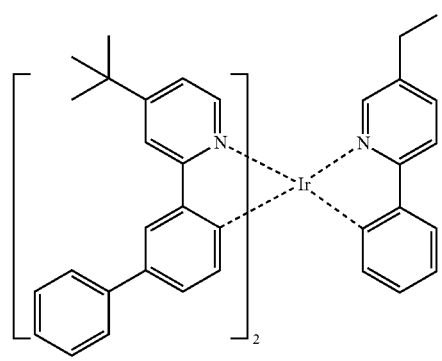
D-194 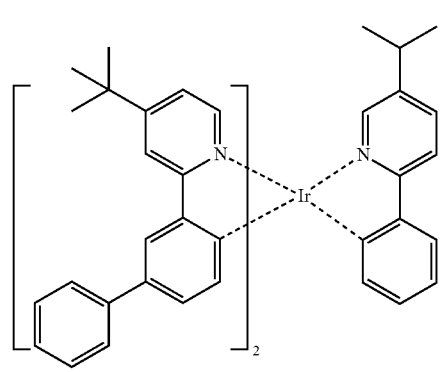
D-195 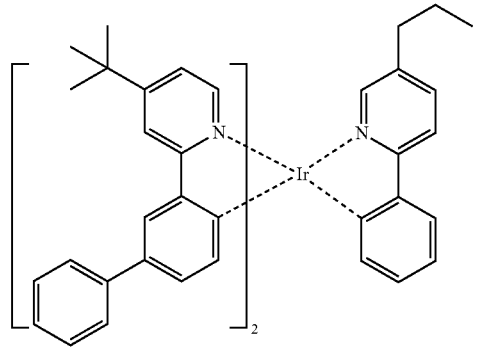

D-196
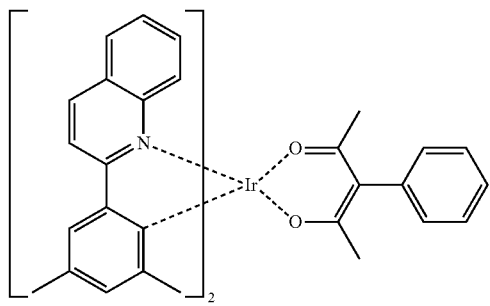
D-197
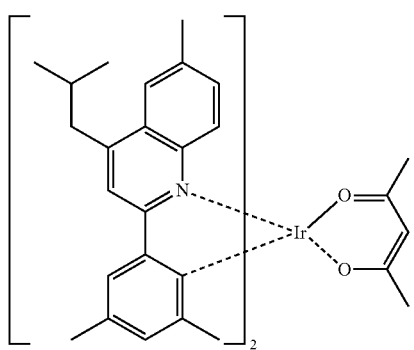
D-198
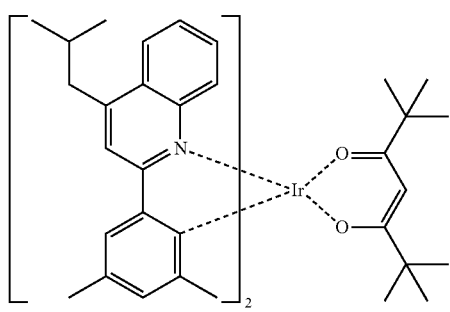
D-199
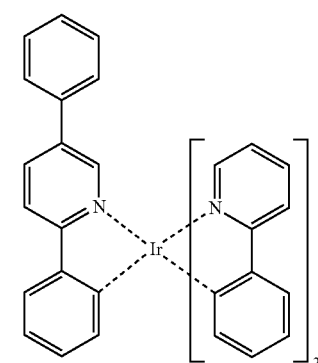
D-200
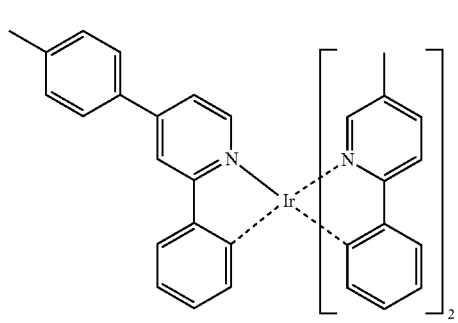
D-201
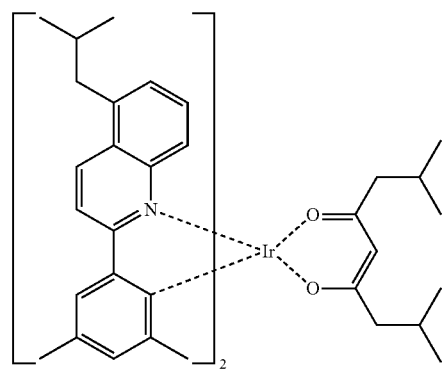
D-202
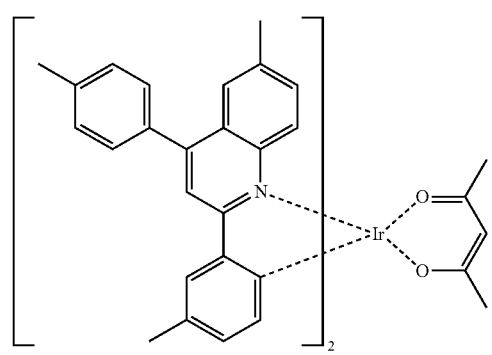
D-203
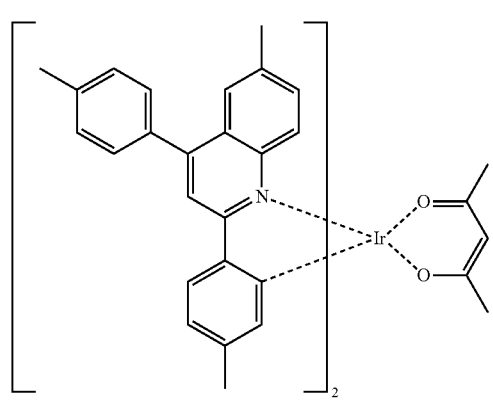
D-204
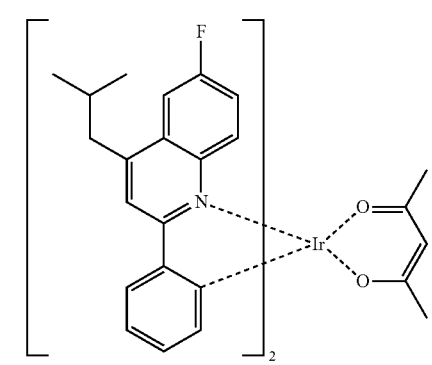

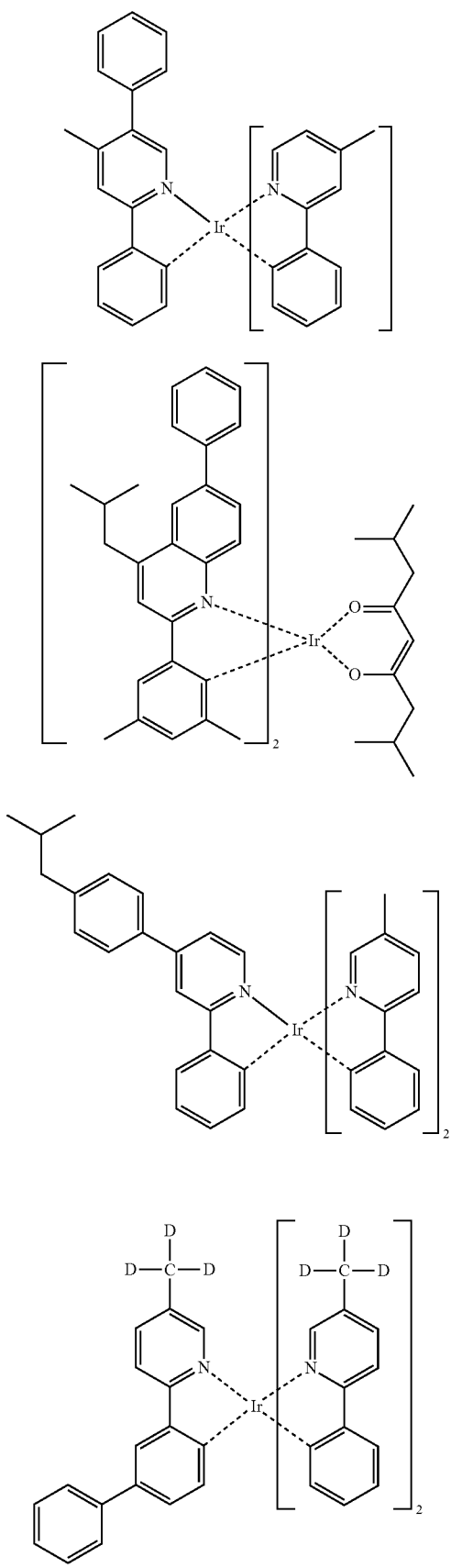

-continued

D-212

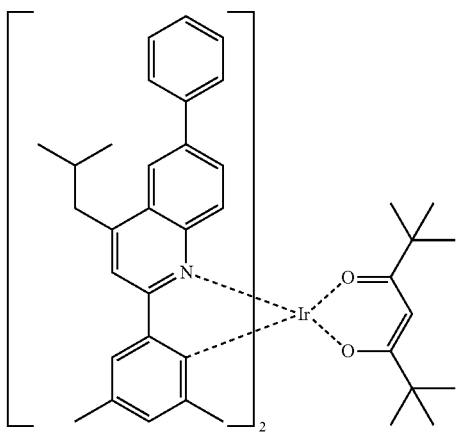

The organic electroluminescent device of the present disclosure may further comprise, in addition to the compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal. The organic layer may further comprise one or more additional light-emitting layers and a charge generating layer.

In addition, the organic electroluminescent device of the present disclosure may emit white light by further comprising at least one light-emitting layer, which comprises a blue electroluminescent compound, a red electroluminescent compound or a green electroluminescent compound known in the field, besides the compound of the present disclosure. If necessary, it may further comprise a yellow light-emitting layer or an orange light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

EXAMPLE 1: PREPARATION OF COMPOUND C-1

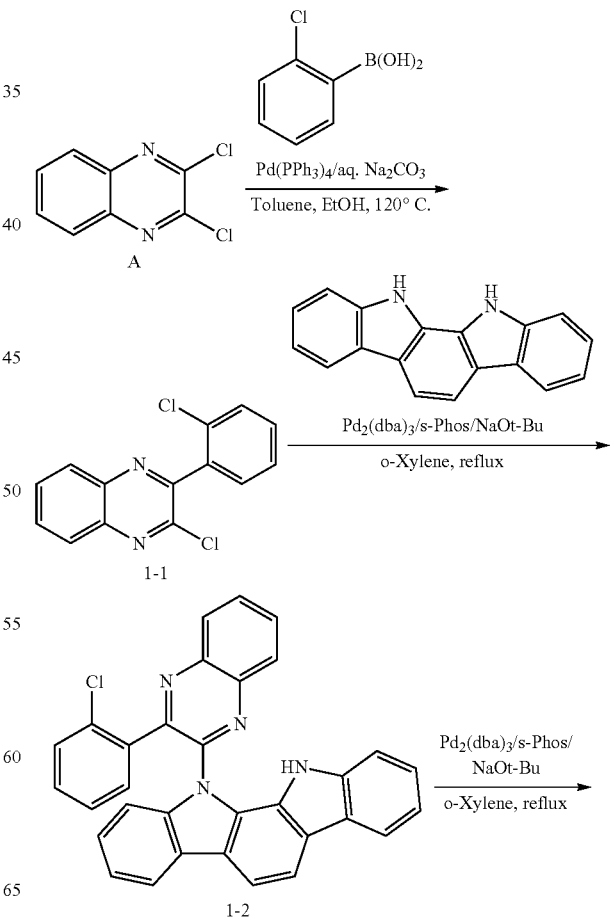

-continued

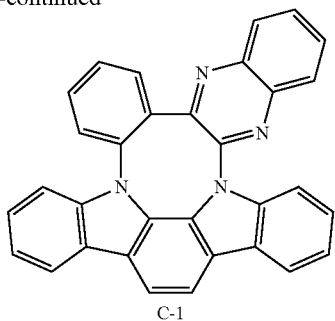

C-1

1) Preparation of Compound 1-1

After introducing compound A (20 g, 100.00 mmol), 2-chlorophenyl boronic acid (15.7 g, 100.00 mmol), tetrakis(triphenylphosphine)palladium (Pd(PPh$_3$)$_4$) (3.5 g, 3.00 mmol), sodium carbonate (26.5 g, 250.00 mmol), toluene (500 mL) and ethanol (125 mL) into a reaction vessel, distilled water (125 mL) was added thereto, and the mixture was then stirred for 4 hours at 120° C. After completing the reaction, the mixture was washed with distilled water and extracted with ethyl acetate. The obtained organic layer was dried with magnesium sulfate, the solvent was removed therefrom using a rotary evaporator, and the remaining product was purified by column chromatography to obtain compound 1-1 (20 g, yield: 73%).

2) Preparation of Compound 1-2

After introducing compound 1-1 (6.5 g, 23.41 mmol), 11,12-dihydroindolo[2,3-a]carbazole (3 g, 11.71 mmol), tris(dibenzylideneacetone)dipalladium (Pd$_2$(dba)$_3$) (3.2 g, 3.51 mmol), 2-dicyclohexylphosphino-2',6'-dimethoxybiphenyl (s-Phos) (2.9 g, 7.02 mmol), sodium tert-butoxide (NaOt-Bu) (3.4 g, 35.14 mmol) and o-xylene (60 mL) into a reaction vessel, the mixture was then stirred under reflux for 4 hours. After completing the reaction, the mixture was washed with distilled water and extracted with ethyl acetate. The obtained organic layer was dried with magnesium sulfate, the solvent was removed therefrom using a rotary evaporator, and the remaining product was purified by column chromatography to obtain compound 1-2 (3.6 g, yield: 62%).

3) Preparation of Compound C-1

After introducing compound 1-2 (3.6 g, 7.27 mmol), tris(dibenzylideneacetone)dipalladium (1.4 g, 1.45 mmol), 2-dicyclohexylphosphino-2',6'-dimethoxybiphenyl (1.2 g, 2.90 mmol), sodium tert-butoxide (2.1 g, 21.81 mmol) and o-xylene (48 mL) into a reaction vessel, the mixture was then stirred under reflux for 2 hours. After completing the reaction, the mixture was washed with distilled water and extracted with ethyl acetate. The obtained organic layer was dried with magnesium sulfate, the solvent was removed therefrom using a rotary evaporator, and the remaining product was purified by column chromatography to obtain compound C-1 (1.2 g, yield: 36%).

$^1$H-NMR (600 MHz, CDCl$_3$) δ 8.26-8.28 (m, 3H), 8.15-8.19 (m, 2H), 7.90-7.91 (m, 1H), 7.85-7.88 (m, 3H), 7.70-7.72 (d, 1H), 7.56-7.58 (m, 3H), 7.46-7.49 (m, 2H), 7.38-7.43 (m, 2H), 7.02-7.03 (t, 1H)

|     | MW     | UV     | PL     | M.P.    |
| --- | ------ | ------ | ------ | ------- |
| C-1 | 458.51 | 432 nm | 521 nm | 355° C. |

DEVICE EXAMPLE 1: PREPARATION OF AN OLED DEVICE COMPRISING THE ORGANIC ELECTROLUMINESCENT COMPOUNDS OF THE PRESENT DISCLOSURE AS A HOST

An OLED device was produced comprising the organic electroluminescent compound according to the present disclosure. A transparent electrode indium tin oxide (ITO) thin film (10 Ω/sq) on a glass substrate for an organic light-emitting diode (OLED) device (Geomatec) was subjected to an ultrasonic washing with trichloroethylene, acetone, ethanol, and distilled water, sequentially, and then was stored in isopropanol. The ITO substrate was then mounted on a substrate holder of a vacuum vapor depositing apparatus. $N^4,N^{4'}$-diphenyl-$N^4,N^{4'}$-bis(9-phenyl-9H-carbazol-3-yl)-[1,1'-biphenyl]-4,4'-diamine was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Next, dipyrazino[2,3-f:2',3'-h]quinoxaline-2,3,6,7,10,11-hexacarbonitrile was introduced into another cell of said vacuum vapor depositing apparatus, and was evaporated by applying an electric current to the cell, thereby forming a second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluorene-2-amine was then introduced into another cell of said vacuum vapor depositing apparatus, and was evaporated by applying an electric current to the cell, thereby forming a first hole transport layer having a thickness of 10 nm on the second hole injection layer. N-(4-(9,9-diphenyl-9H,9'H-[2,9'-bifluorene]-9'-yl)phenyl)-9,9-dimethyl-N-phenyl-9H-fluorene-2-amine was then introduced into another cell of said vacuum vapor depositing apparatus, and was evaporated by applying an electric current to the cell, thereby forming a second hole transport layer having a thickness of 60 nm on the first hole transport layer. After forming the hole injection layer and the hole transport layer, a light-emitting layer was formed thereon as follows: compound C-1 was introduced into one cell of said vacuum vapor depositing apparatus as a host, and compound D-96 was introduced into another cell as a dopant. The dopant was deposited in a doping amount of 3 wt % based on the total amount of the host and dopant to form a light-emitting layer having a thickness of 40 nm on the second hole transport layer. 2,4-bis(9,9-dimethyl-9H-fluoren-2-yl)-6-(naphthalen-2-yl)-1,3,5-triazine and lithium quinolate were then introduced into another two cells, evaporated at the same time to form an electron transport layer having a thickness of 30 nm on the light-emitting layer. After depositing lithium quinolate as an electron injection layer having a thickness of 2 nm on the electron transport layer, an Al cathode having a thickness of R$_0$ nm was deposited by another vacuum vapor deposition apparatus. Thus, an OLED device was produced.

The produced OLED device showed a red emission having a luminance of 1,000 cd/m$^2$, a luminous efficiency of 29.2 cd/A at 3.4 V, and a power efficiency of 27.3 lm/W. The time taken to be reduced to 90% of the luminance, where the early luminance is 100%, at 5,000 nits and a constant current was 15 hours or more.

COMPARATIVE DEVICE EXAMPLE 1: PREPARATION OF AN OLED DEVICE COMPRISING CONVENTIONAL ORGANIC ELECTROLUMINESCENT COMPOUNDS

An OLED device was produced in the same manner as in Device Example 1, except for using compound CBP (4,4'-N,N'-dicarbazole-biphenyl) as a host of the light-emitting material.

The produced OLED device showed a red emission having a luminance of 1,000 cd/m$^2$, a luminous efficiency of 14.3 cd/A at 10.0 V, and a power efficiency of 4.5 lm/W. The time taken to be reduced to 90% of the luminance, where the early luminance is 100%, at 5,000 nits and a constant current was less than 1 hour.

The invention claimed is:

1. An organic electroluminescent compound represented by the following formula 1:

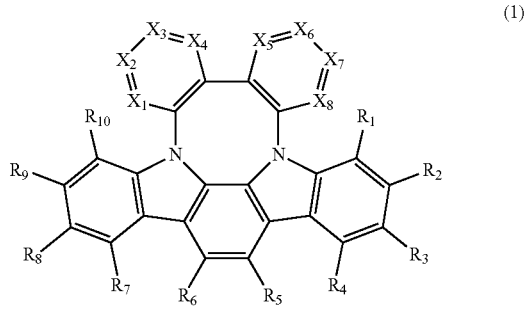

(1)

wherein $X_1$ to $X_8$ represent N or $CR_{11}$;

$R_1$ to $R_{11}$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$NR_{12}R_{13}$, or —$SiR_{14}R_{15}R_{16}$; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen, and sulfur;

$R_{12}$ to $R_{16}$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered) heteroaryl;

the heterocycloalkyl or the heteroaryl contains at least one hetero atom selected from B, N, O, S, Si, and P.

2. The organic electroluminescent compound according to claim 1, wherein the substituents of the substituted (C1-C30)alkyl, the substituted (C3-C30)cycloalkyl, the substituted (C3-C30)cycloalkenyl, the substituted (3- to 7-membered) heterocycloalkyl, the substituted (C6-C30)aryl, the substituted (3- to 30-membered)heteroaryl, and the substituted mono- or polycyclic, (C3-C30) alicyclic or aromatic ring, each independently, are at least one selected from the group consisting of deuterium, a halogen, a cyano, a carboxyl, a nitro, a hydroxyl, a (C1-C30)alkyl, a halo(C1-C30) alkyl, a (C2-C30) alkenyl, a (C2-C30) alkynyl, a (C1-C30) alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (5- to 30-membered)heteroaryl unsubstituted or substituted with a (C6-C30)aryl, a (C6-C30)aryl unsubstituted or substituted with a (5- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30) alkyl, and a (C1-C30)alkyl(C6-C30)aryl.

3. The organic electroluminescent compound according to claim 1, wherein $R_1$ to $R_{11}$, each independently, represent hydrogen, deuterium, a substituted or unsubstituted (C1-C20)alkyl, a substituted or unsubstituted (C3-C20)cycloalkyl, a substituted or unsubstituted (C3-C20)cycloalkenyl, a substituted or unsubstituted (C6-C20)aryl, a substituted or unsubstituted (3- to 20-membered)heteroaryl, or —$NR_{12}R_{13}$; or are linked to an adjacent substituent(s) to form a substituted or unsubstituted, mono- or polycyclic, (C3-C20) alicyclic or aromatic ring, whose carbon atom(s) may be replaced with at least one hetero atom selected from nitrogen, oxygen, and sulfur; and $R_{12}$ to $R_{16}$, each independently, represent a substituted or unsubstituted (C1-C20) alkyl, a substituted or unsubstituted (C3-C20)cycloalkyl, a substituted or unsubstituted (C3-C20)cycloalkenyl, a substituted or unsubstituted (C6-C20)aryl, or a substituted or unsubstituted (3- to 20-membered)heteroaryl.

4. The organic electroluminescent compound according to claim 1, wherein the compound represented by formula 1 is selected from the group consisting of:

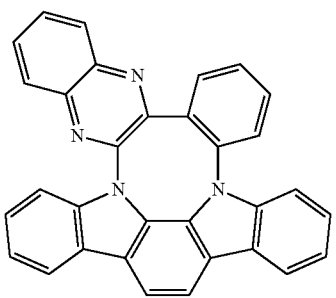

C-1

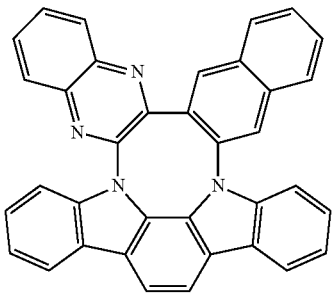

C-2

C-3
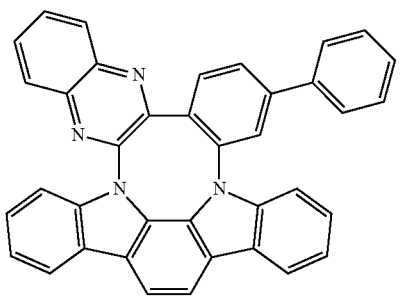
C-4
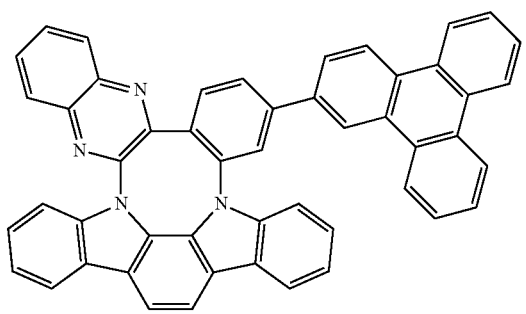
C-5
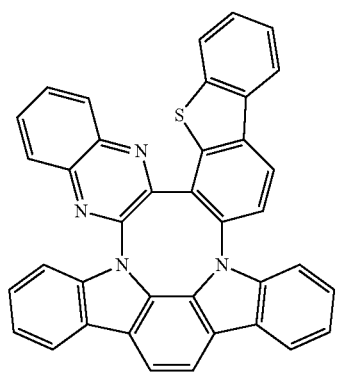
C-6
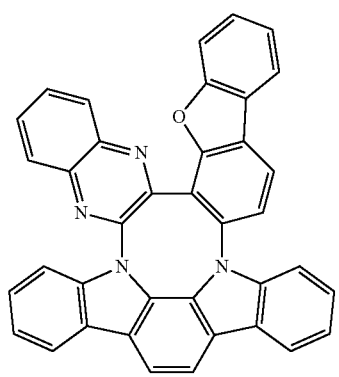
C-7
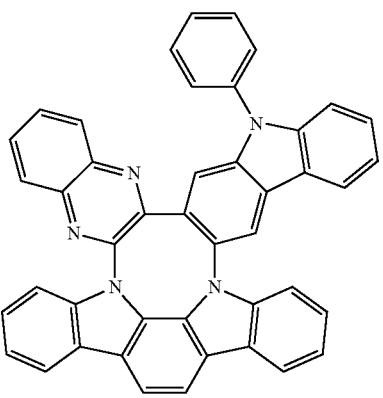
C-8
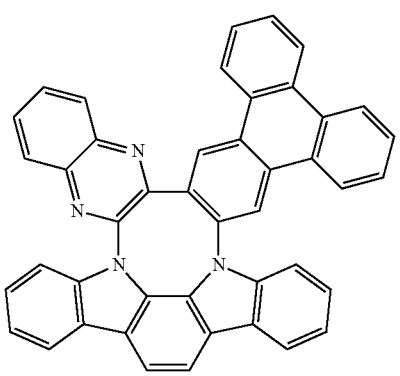
C-9
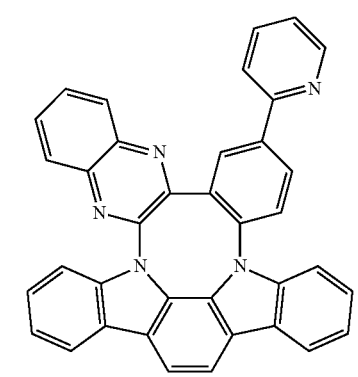
C-10
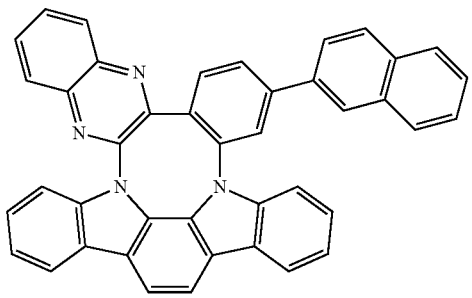

C-11
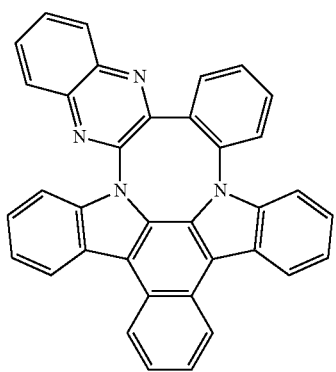
C-12
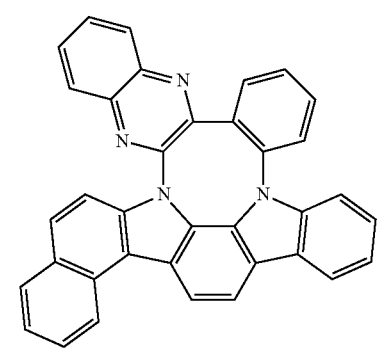
C-13
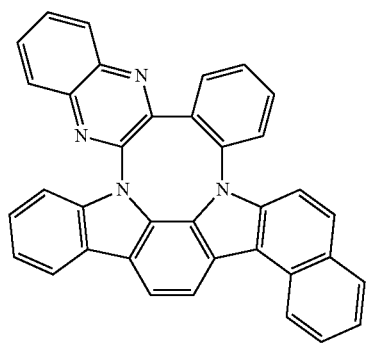
C-14
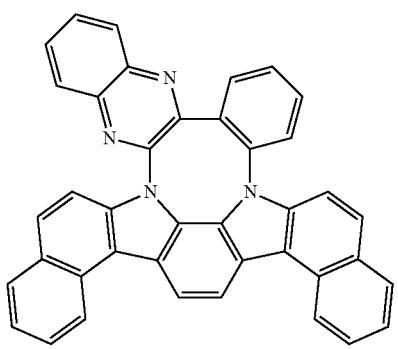
C-15
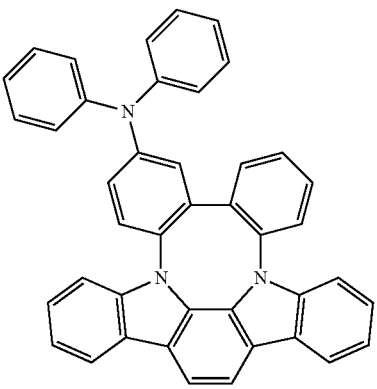
C-16
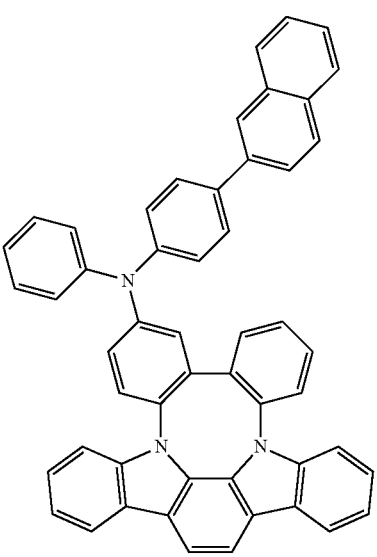
C-17
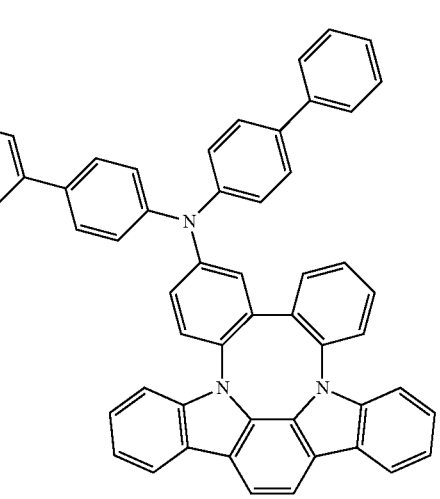

-continued
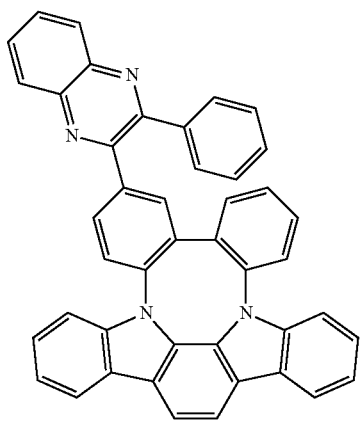
C-18
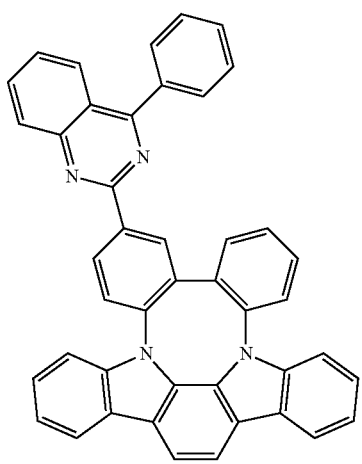
C-19
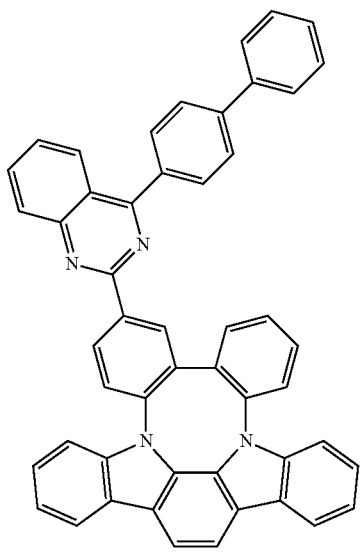
C-20
-continued
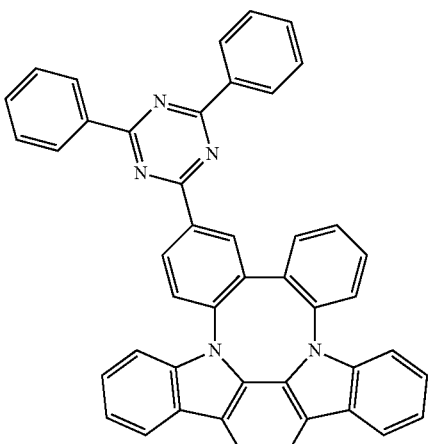
C-21
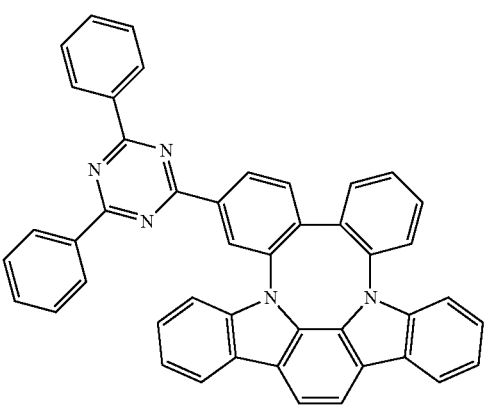
C-22
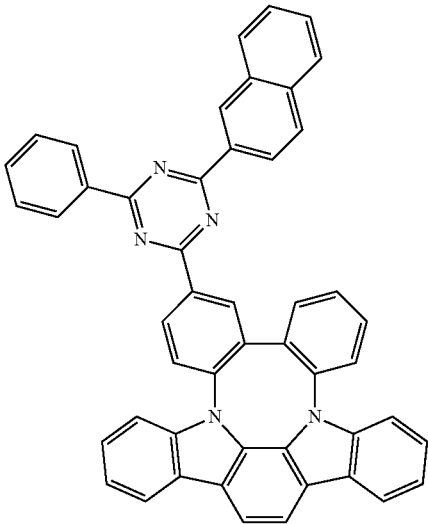
C-23

C-24
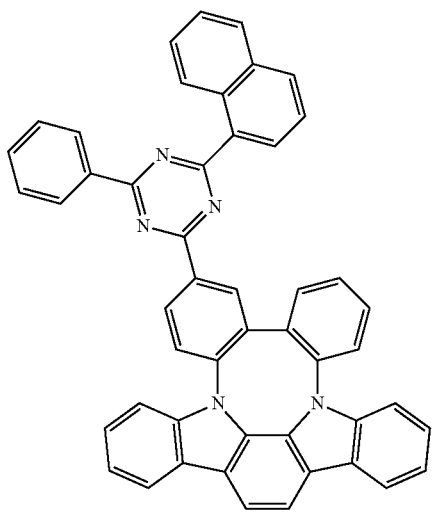
C-25
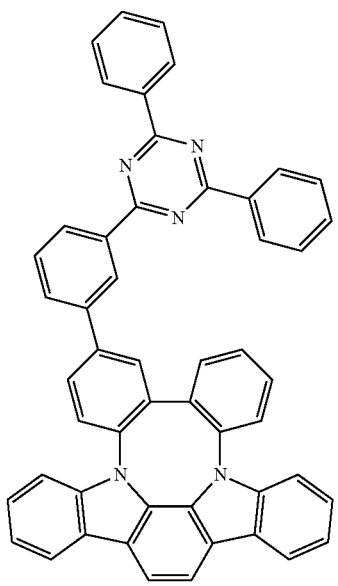
C-26
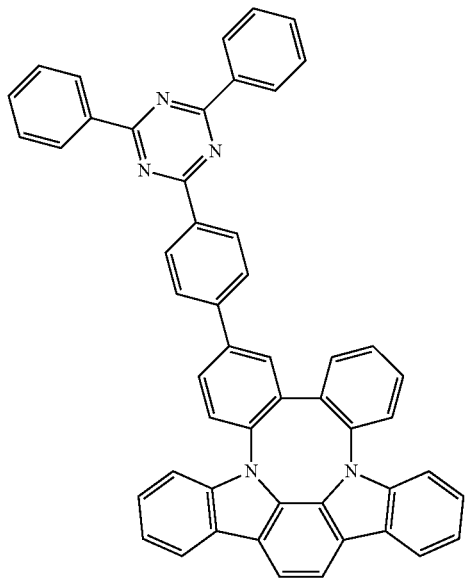
C-27
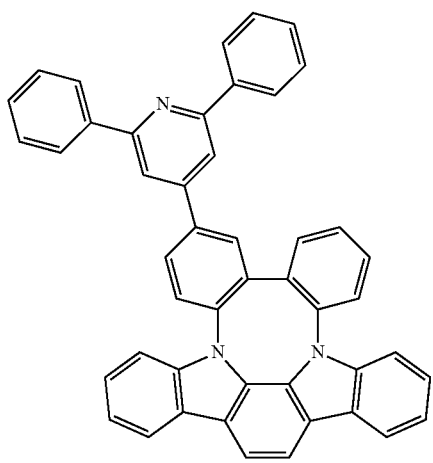
C-28
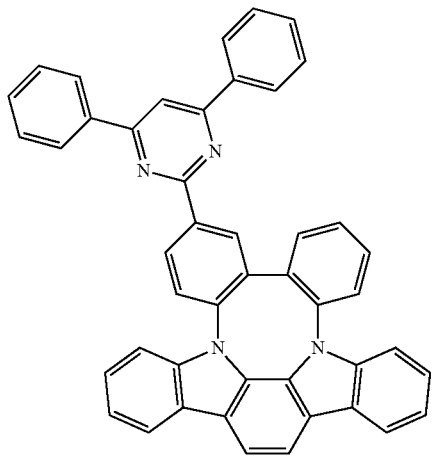
C-29
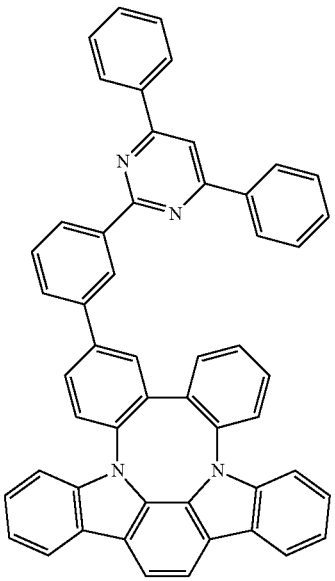

C-30
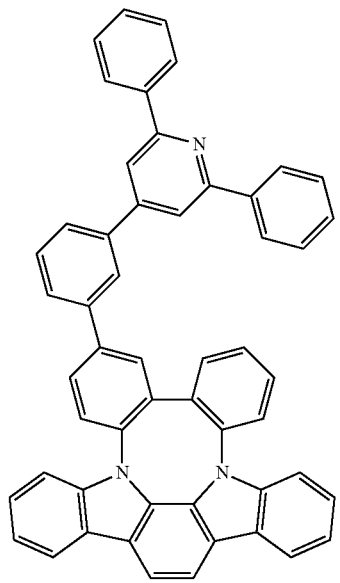
C-31
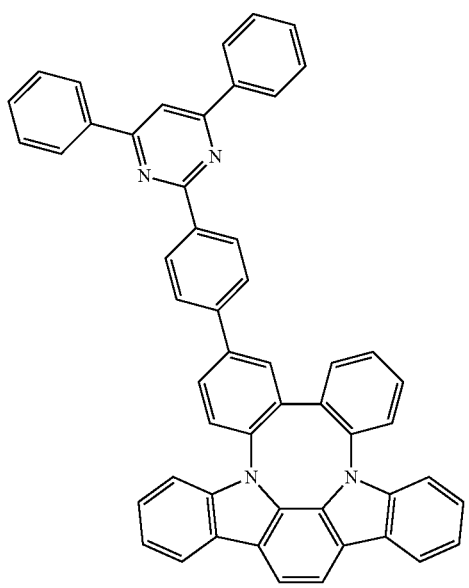
C-32
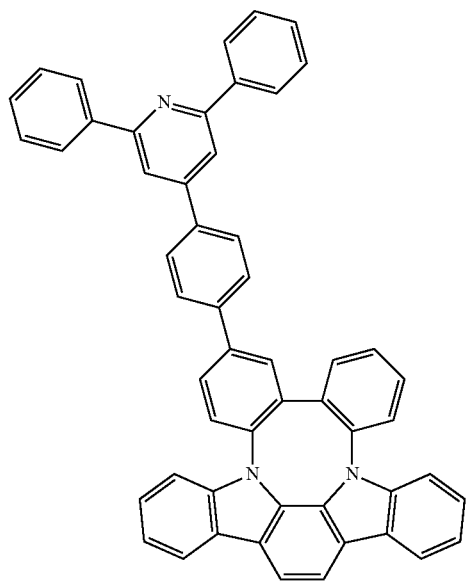
C-33
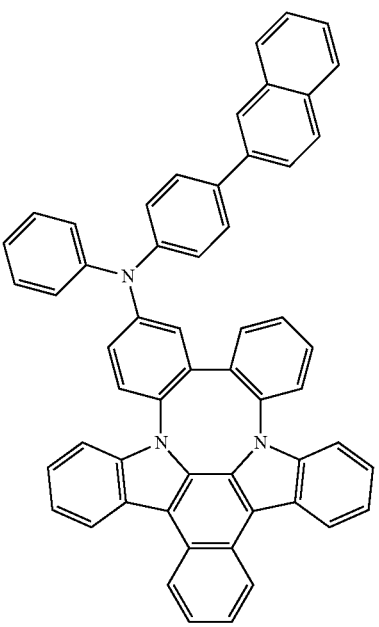

C-34
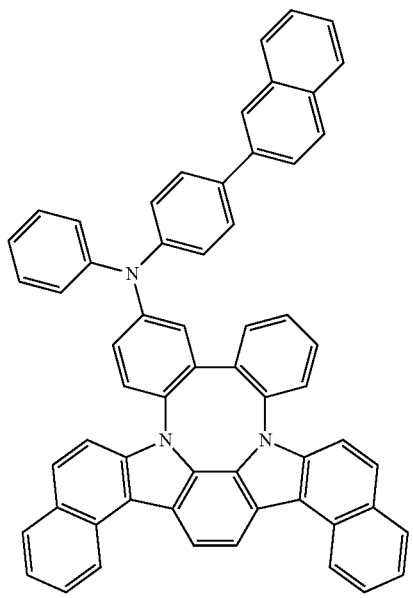
C-35
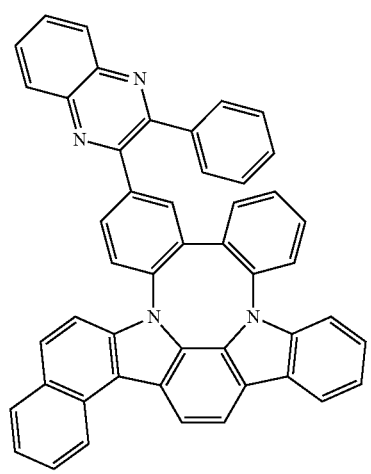
C-36
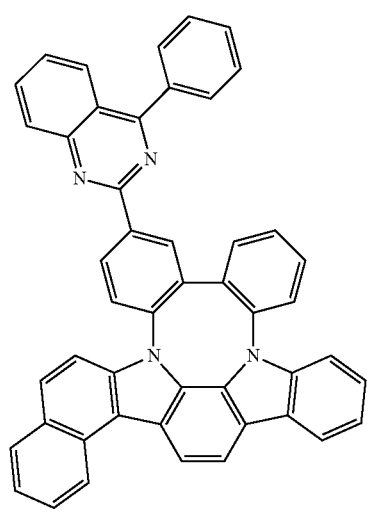
C-37
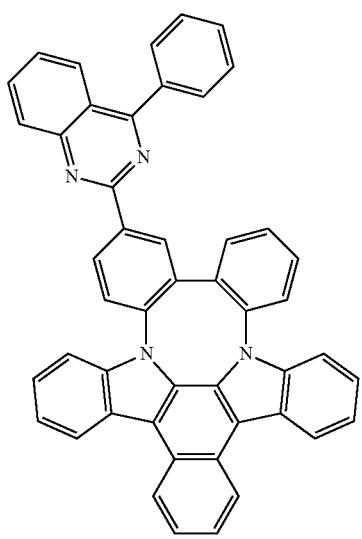
C-38
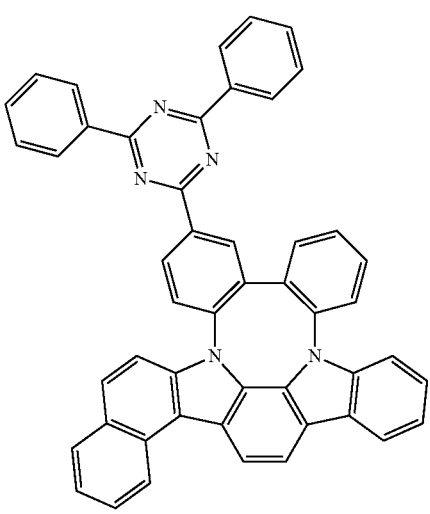
C-39
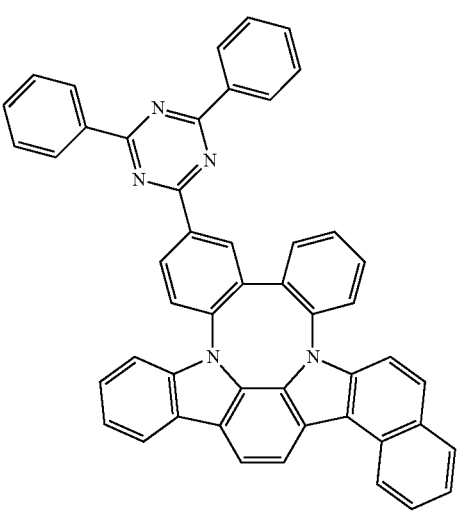

C-40
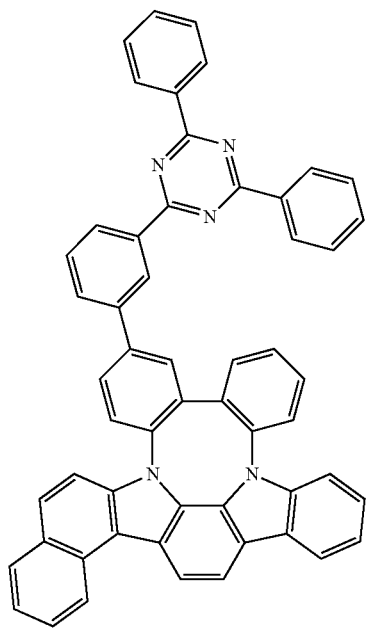
C-41
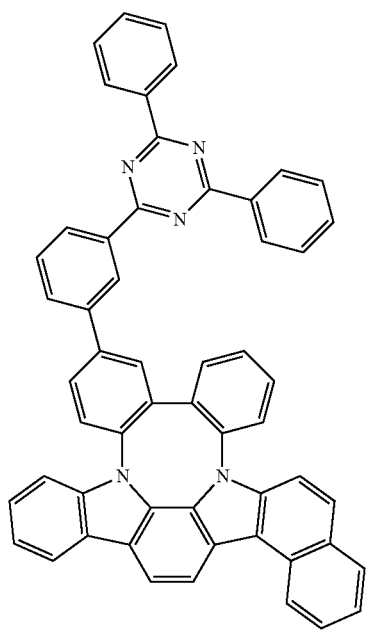
C-42
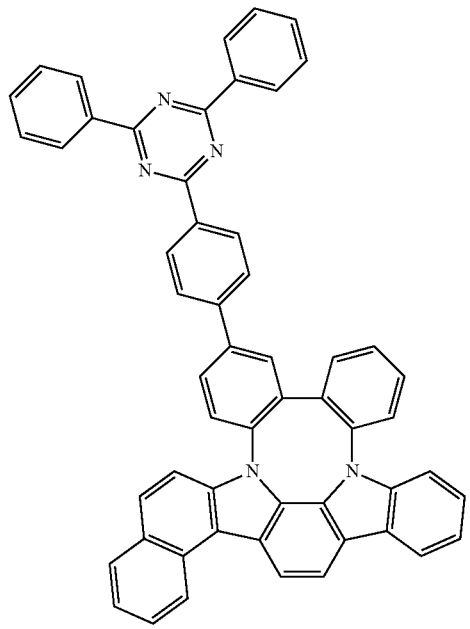
C-43
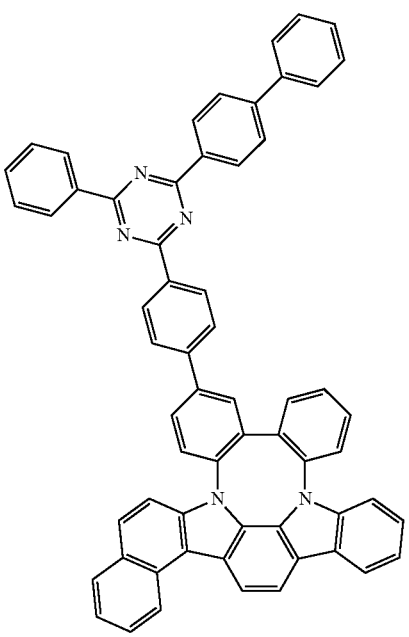

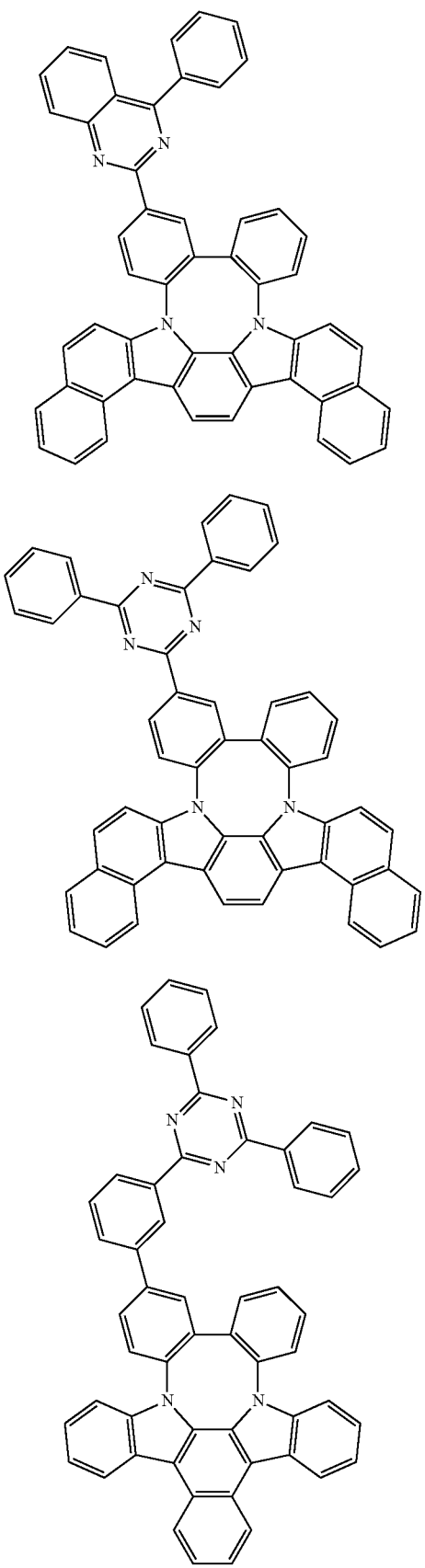
C-44
C-45
C-46
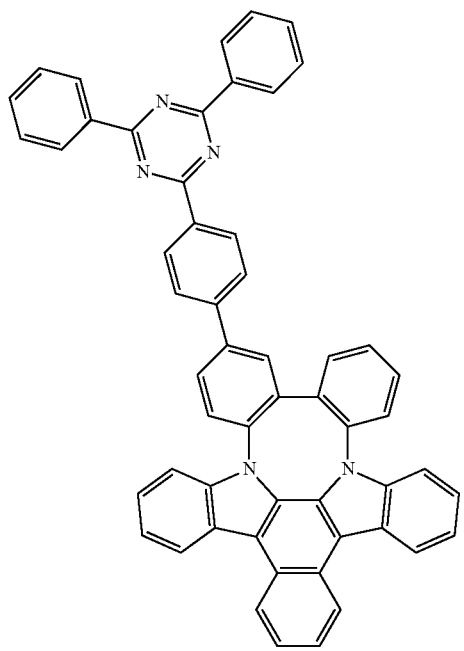
C-47
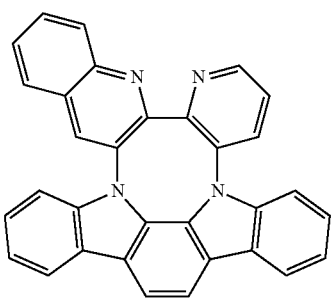
C-48
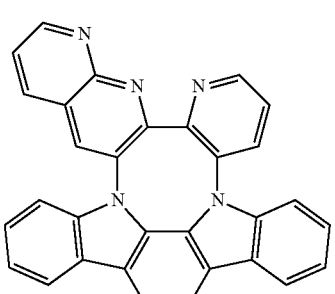
C-49
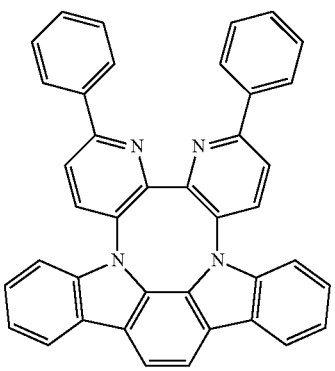
C-50

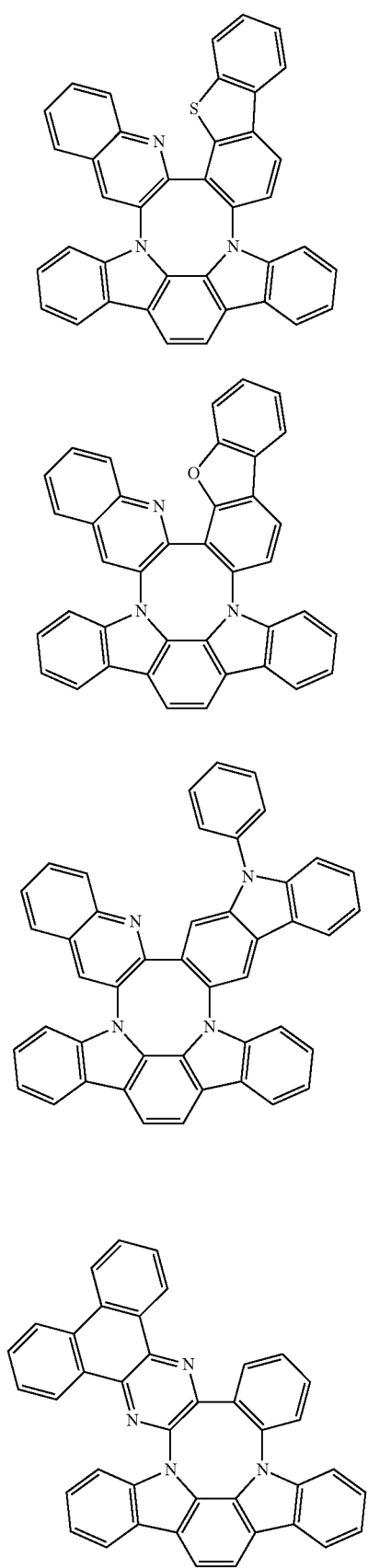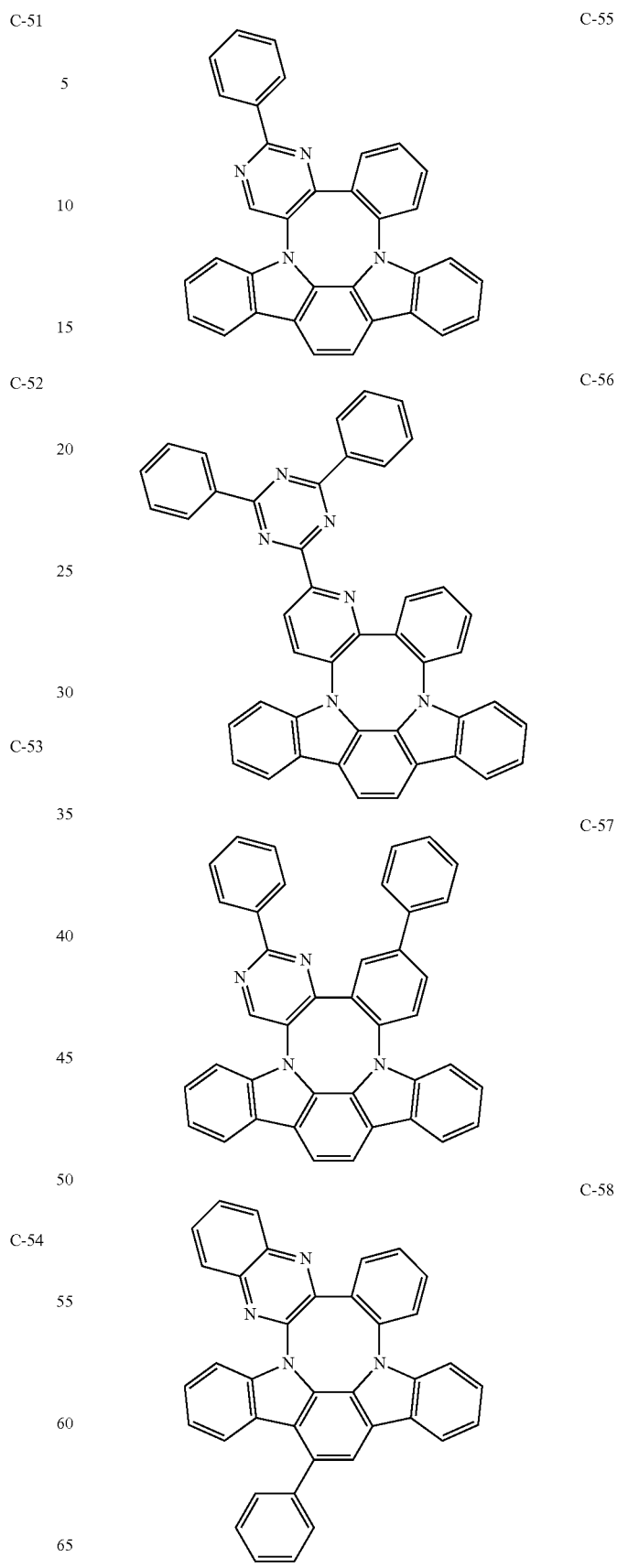

-continued
C-59
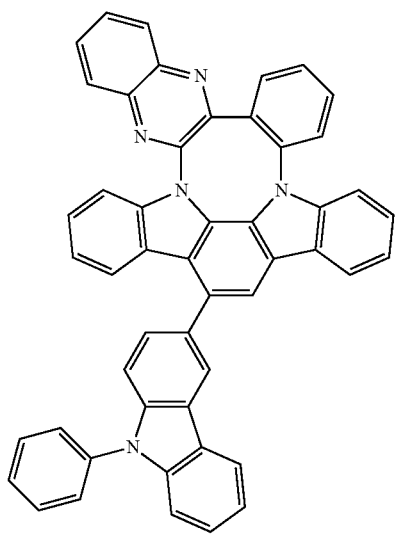
C-60
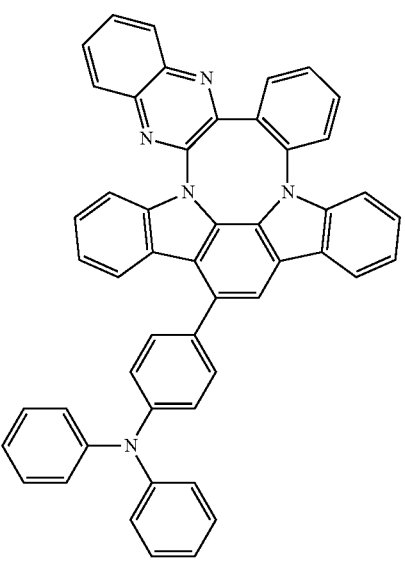
C-61
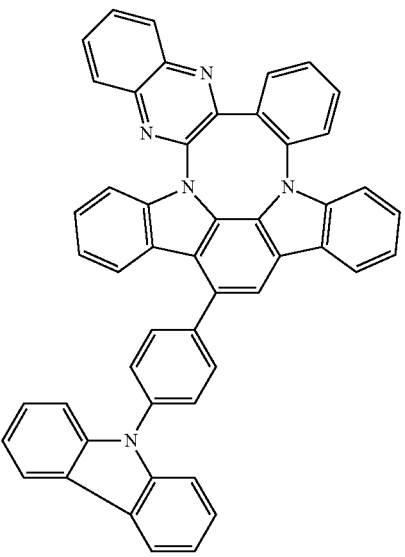
-continued
C-62
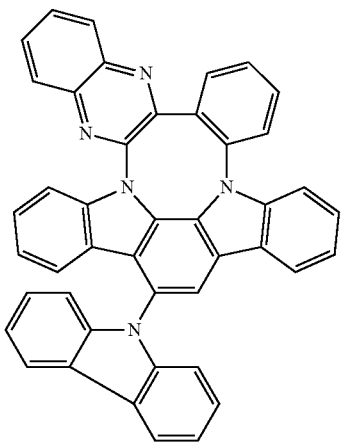
C-63
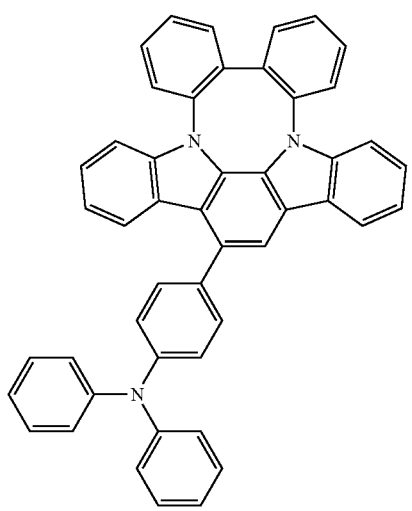
C-64
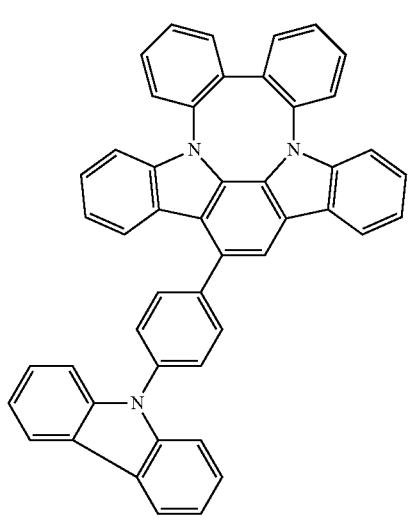

-continued
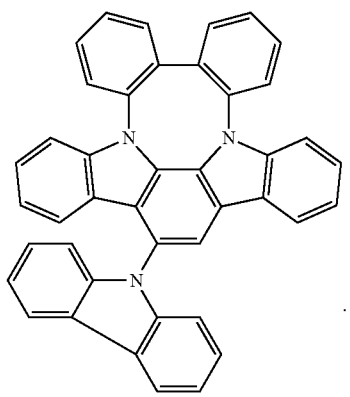
C-65
5. An organic electroluminescent device comprising the organic electroluminescent compound according to claim 1.